(12) United States Patent
Asada et al.

(10) Patent No.: US 7,576,129 B2
(45) Date of Patent: *Aug. 18, 2009

(54) CARBOXYLIC ACID COMPOUNDS

(75) Inventors: Masaki Asada, Mishima-gun (JP);
Kaoru Kobayashi, Mishima-gun (JP);
Masami Narita, Mishima-gun (JP);
Kazutoyo Sato, Mishima-gun (JP);
Atsushi Kinoshita, Mishima-gun (JP);
Toshihiko Nagase, Mishima-gun (JP);
Ken Yoshikawa, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 615 days.

This patent is subject to a terminal disclaimer.

(21) Appl. No.: 10/544,646

(22) PCT Filed: Feb. 6, 2004

(86) PCT No.: PCT/JP2004/001262

§ 371 (c)(1),
(2), (4) Date: Nov. 23, 1995

(87) PCT Pub. No.: WO2004/069788

PCT Pub. Date: Aug. 19, 2004

(65) Prior Publication Data

US 2007/0167498 A1    Jul. 19, 2007

(30) Foreign Application Priority Data

Feb. 7, 2003    (JP) .............................. 2003-031593

(51) Int. Cl.
*A61K 31/195*    (2006.01)
*A61K 31/34*    (2006.01)
*C07D 317/44*    (2006.01)
*C07D 335/00*    (2006.01)
*C07C 63/00*    (2006.01)

(52) U.S. Cl. ...................... 514/539; 514/563; 546/329; 549/13; 549/32; 549/59; 549/74; 549/426; 549/434; 549/445; 549/469; 560/21; 562/405

(58) Field of Classification Search ................ 502/409; 560/21; 549/445, 469, 426, 13, 32, 59, 74, 549/434; 546/329; 514/563, 539

See application file for complete search history.

(56) References Cited

U.S. PATENT DOCUMENTS 3,950,393 A * 4/1976 Keck et al. .................... 560/37
5,716,993 A * 2/1998 Ozaki et al. .................. 514/619
6,018,068 A * 1/2000 Nagao et al. .................. 560/10
6,043,275 A * 3/2000 Maruyama et al. ........... 514/530
6,462,081 B1 * 10/2002 Maruyama et al. .......... 514/530

FOREIGN PATENT DOCUMENTS

EP    1642594 A1    4/2006
WO    WO 02/16311 A1    2/2002
WO    WO 02/100403 A1    12/2002
WO    WO 03/016254 A1    2/2003

OTHER PUBLICATIONS

Minami, Toshiaki, et al.; Characterization of EP Receptor Subtypes Responsible for Prostaglandin E2-induced Pain Responses by Use of EP1 and EP3 Receptor Knockout Mice; British Journal of Pharmacology (2001) 133,438-444.

Schüßler, B. Comparison of the mode of action of prostaglandin E2 (PGE2) and sulprostone, a PGE2- derivative on the lower urinary tract in healthy women Urological Research vol. 18, No. 5 349-352, 1990.

Nakamura, K. et al., Prostaglandin EP3 Receptor Protein in Serotonin And Catecholamine Cell Groups: A Double Immunofluorescence Study In The Rat Brain, Neuroscience 2001;103 vol. (3)- pp. 763-775.

Nasushita, R. et al., A Comparative Study of Adrenocorticotropin-releasing activity of prostaglanding E1, E1, F2? and D2 In The Rat; The Japanese Journal of Pharmacology vol. 79 suppl. I p. 87 Prostaglandins Leukot Essent Fatty Acids Feb. 1997 56(2):165-8.

Nishigaki Nobuhiro, et al.; Characterization of the Prostaglandin E Receptor Expressed on a Cultured Mast Line, BNu-2cl3; CellBiochem Pharmacol. Sep. 1, 1993;46(5):863-9.

Fedyk Eric, R. ,et al., Prostaglandin E2 Receptors of the EP2 and EP4 Subtypes Regulate Activation and Differentiation of Mouse B Lymphocytes to IgE-secreting Cells; Proc Natl Acad Sci USA. Oct. 1, 1996;93(20):10978-83.

Gomi Kaede et al.; Prostaglandin E2 Selectively Enhances the IgE-Mediated Production of IL-6 and Granulocyte-Macrophage Colony-Stimulationg Factor by Mast Cells Trough an EP1/EP3-Dependent Mechanism; The Journal of Immunology, 2000, 165:6545-6552.

* cited by examiner

*Primary Examiner*—Janet L. Andres
(74) *Attorney, Agent, or Firm*—Sughrue Mion, PLLC

(57) ABSTRACT

The present invention relates to a carboxylic acid compound of formula (I):

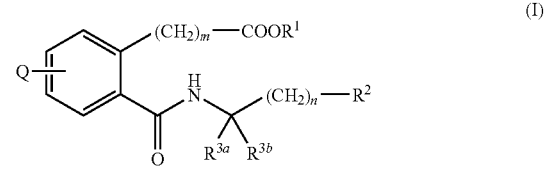

wherein $R^1$ is H, alkyl; m is 2, 3; n is 0-2; $R^2$ is phenyl, naphthyl, benzofuran, benzothiophene; Q is —$CH_2$—O—Cyc1, —$CH_2$-Cyc2, -L-Cyc3; $R^{3a}$ and $R^{3b}$ each independently is hydrogen, alkyl or taken together form tetrahydro-2H-pyran; a pharmaceutically acceptable salt thereof, a method for producing a process of the preparation thereof and a pharmaceutical agent comprising the same as an active ingredient. The compound of formula (I) have an antagonizing activity against $PGE_2$ receptor, specifically $EP_3$ receptor which is subtype thereof, and are useful for the prevention and/or treatment of itching, pain, urinary disturbance or stress disease.

10 Claims, No Drawings

CARBOXYLIC ACID COMPOUNDS

TECHNICAL FIELD

The present invention relates to carboxylic acid compounds. More specifically, the present invention relates to a carboxylic acid compound of formula (I):

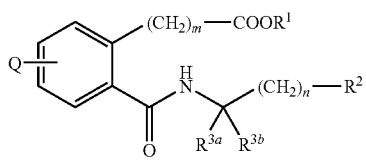

wherein all symbols have the same meanings as described below; a salt thereof, a solvate thereof or a prodrug thereof, a method for producing a process of the preparation thereof and a pharmaceutical agent comprising the same as an active ingredient.

BACKGROUND ART

Prostaglandin $E_2$ ($PGE_2$) has been known as a metabolite in the arachidonic acid cascade. It has been known that $PGE_2$ possesses cyto-protective activity, uterine contractile activity, a pain-inducing effect, a promoting effect on digestive peristalsis, an awaking effect, a suppressive effect on gastric acid secretion, hypotensive activity, and diuretic activity.

In the recent study, it was found that $PGE_2$ receptor was divided into some subtypes, which possesses different physical roles from each other. At present, four receptor subtypes are known and they are called $EP_1$, $EP_2$, $EP_3$ and $EP_4$ respectively [*J. Lipid Mediators Cell Signaling,* 12, 379-391 (1995)].

Among these subtypes, $EP_3$ receptor was believed to be involved in signal transduction of peripheral nerve, control of exothermal reaction in central nerve, formation of memory by expressing in cerebral neuron, vascularization, and reabsorption of urine by expressing in renal tubular, uterine contraction, production of ACTH, platelet aggregation. Besides, it was expressed in vascular smooth muscle, heart and gastrointestinal tract also.

Therefore, the compounds that can bind to $EP_3$ receptor strongly and show the antagonizing activity are useful for the prevention and/or treatment of diseases induced by excess activation of $EP_3$ receptor.

As a compound possessing $EP_3$ and/or $EP_4$ receptor antagonist activity, in a specification of WO 02/16311, a carboxylic acid compound of formula (IA):

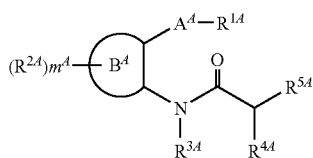

wherein $R^{1A}$ is COOH, $COOR^{6A}$; $R^{6A}$ is C1-6 alkyl etc.; $A^A$ is C1-6 alkylene etc.; $R^{2A}$ is C1-6 alkyl, C2-6 alkenyl, C2-6 alkynyl, C1-6 alkoxy, halogen atom, $CF_3$, cyano, nitro, hydroxyl, $NR^{11A}R^{12A}$, $CONR^{11A}R^{12A}$, $SO_2NR^{11A}R^{12A}$, or —$S(O)_{XA}$—(C1-6)alkyl; $m^A$ is 0, 1, or 2; $R^{11A}$ and $R^{12A}$ each independently, is hydrogen or C1-4 alkyl; $X^A$ is 0, 1 or 2; $B^A$ ring is C5-7 membered mono-carbocyclic ring; $R^{3A}$ is hydrogen or C1-4 alkyl; $R^{4A}$ is C1-8 alkyl, C2-8 alkenyl; $R^{5A}$ is C5-10 mono- or bi-carbocyclic ring or 5-10 membered mono- or bi-heterocyclic ring including at least of hetero atoms selected from nitrogen, oxygen or sulfur, which each ring was substituted with 1-2 of $R^{13A}$ or unsubstituted; $R^{13A}$ is C1-6 alkyl, C1-6 alkoxy, halogen atom, $CF_3$, cyano, C1-4 alkoxy (C1-4)alkyl, phenyl, phenyl(C1-6)alkyl, —(C1-4 alkylene)$_{yA}$-J-(C1-8 alkylene)$_{ZA}$-$R^{14A}$, benzoyl, or thiophenecarbonyl; or a non-toxic salt thereof, are described.

DISCLOSURE OF THE INVENTION

The present inventors have energetically studied to find the compound, which bind to $PGE_2$ receptor, $EP_3$ receptor specifically and show an antagonizing activity against it, to find out that the carboxylic acid compound of formula (I) achieve the purpose and completed the present invention.

The present invention is relates to the followings:

1) A carboxylic acid compound of formula (I):

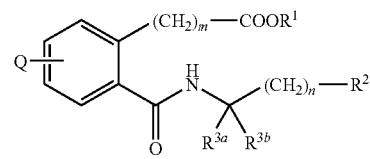

wherein $R^1$ is hydrogen or C1-4 alkyl;

$R^2$ is phenyl, naphthyl, benzofuranyl or benzothionyl, which is unsubstituted or substituted with 1-2 of C1-4 alkyl and/or halogen;

Q is (i) —$CH_2$—O-Cyc1, (ii) —$CH_2$-Cyc2 or (iii) -L-Cyc3;

Cyc1 is phenyl or pyridyl, which is unsubstituted or substituted with 1-2 of $R^4$;

Cyc2 is indolyl which is unsubstituted or substituted with 1-2 of $R^4$;

Cyc3 is phenyl substituted with 1-2 of $R^4$;

L is —O— or —NH—;

$R^{3a}$ and $R^{3b}$ each independently is hydrogen or C1-4 alkyl or $R^{3a}$ and $R^{3b}$, taken together with the carbon atom to which they are attached, form tetrahydro-2H-pyran;

m is 2 or 3;

n is 0, 1 or 2;

$R^4$ is C1-4 alkyl, C1-4 alkylthio, halogen or cyano, or when Cyc3 is phenyl substituted with two $R^4$, two $R^4$ taken together with phenyl may form

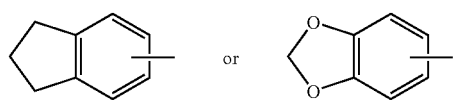

a salt thereof, a solvate thereof or a prodrug thereof

2) The carboxylic acid compound according to the above 1), which is (1) 3-(4-(2,5-difluorophenoxymethyl)-2-(((((1R)-1-(naphthalen-2-yl)ethyl)amino)carbonyl)phenyl)propanoic acid, (2) 3-(4-(2,5-dichlorophenoxymethyl)-2-(((4-(3-methylphenyl)tetrahydro-2H-pyran-4-yl)amino)carbonyl)phenyl)propanoic acid,
(3) 3-(4-(2-chloro-5-methylphenoxymethyl)-2-(((4-(3-methylphenyl)tetrahydro-2H -pyran-4-yl)amino)carbonyl)phenyl)propanoic acid,
(4) 3-(4-(2-chloro-5-fluorophenoxymethyl)-2-(((4-(3-methylphenyl)tetrahydro-2H -pyran-4-yl)amino)carbonyl)phenyl)propanoic acid,
(5) 3-(4-(2,5-difluorophenoxymethyl)-2-(((4-phenyltetrahydro-2H-pyran-4-yl)amino)carbonyl)phenyl)propanoic acid,
(6) 3-(4-(2,5-dichlorophenoxymethyl)-2-(((4-phenyltetrahydro-2H-pyran-4-yl)amino)carbonyl)phenyl)propanoic acid,
(7) 3-(4-(2-chloro-5-fluorophenoxymethyl)-2-(((4-phenyltetrahydro-2H-pyran-4-yl)amino)carbonyl)phenyl)propanoic acid,
(8) 3-(4-(2,5-difluorophenoxymethyl)-2-(((((1R)-3-methyl-1-(3-methylphenyl)butyl)amino)carbonyl)phenyl)propanoic acid,
(9) 3-(4-(3-cyanophenoxymethyl)-2-(((((1R)-3-methyl-1-(3-methylphenyl)butyl)amino)carbonyl)phenyl)propanoic acid,
(10) 3-(4-(2,5-dimethylphenoxymethyl)-2-(((((1R)-3-methyl-1-(3-methylphenyl)butyl)amino)carbonyl)phenyl)propanoic acid,
(11) 3-(4-(2,5-difluorophenoxymethyl)-2-(((4-(naphthalen-2-yl)tetrahydro-2H-pyran-4-yl)amino)carbonyl)phenyl)propanoic acid,
(12) 3-(4-(2,5-dimethylphenoxymethyl)-2-(((4-(3-methylphenyl)tetrahydro-2H-pyran-4-yl)amino)carbonyl)phenyl)propanoic acid,
(13) 3-(4-(3-cyanophenoxymethyl)-2-(((4-(naphthalen-2-yl)tetrahydro-2H-pyran-4-yl)amino)carbonyl)phenyl)propanoic acid,
(14) 3-(4-(2,5-dimethylphenoxymethyl)-2-(((4-(naphthalen-2-yl)tetrahydro-2H-pyran-4-yl)amino)carbonyl)phenyl)propanoic acid,
(15) 3-(4-(5-fluoroindol-1-ylmethyl)-2-(((((1R)-1-(3,5-dimethylphenyl)-3-methylbutyl)amino)carbonyl)phenyl)propanoic acid,
(16) 3-(4-(2,4-dimethylphenoxymethyl)-2-(((((1R)-1-(3,5-dimethylphenyl)-3-methylbutyl)amino)carbonyl)phenyl)propanoic acid,
(17) 3-(2-(((4-(naphthalen-2-yl)tetrahydro-2H-pyran-4-yl)amino)carbonyl)-4-phenoxymethylphenyl)propanoic acid,
(18) 3-(2-(((4-(naphthalen-2-yl)tetrahydro-2H-pyran-4-yl)amino)carbonyl)-4-(3-pyridyloxymethyl)phenyl)propanoic acid,
(19) 3-(4-(3-chlorophenoxymethyl)-2-(((4-(naphthalen-2-yl)tetrahydro-2H-pyran-4-yl)amino)carbonyl)phenyl)propanoic acid,
(20) 3-(4-(3,4-dimethyl phenoxymethyl)-2-(((((1R)-1-(3,5-dimethylphenyl)-3-methylbutyl)amino)carbonyl)phenyl)propanoic acid,
(21) 3-(4-(2-chloro-5-fluorophenoxymethyl)-2-(((((1R)-1-(3,5-dimethylphenyl)-3-methylbutyl)amino)carbonyl)phenyl)propanoic acid,
(22) 3-(2-(((((1R)-1-(3,5-dimethylphenyl)-3-methylbutyl)amino)carbonyl)-4-(3-methylindol-1-ylmethyl)phenyl)propanoic acid,
(23) 3-(4-(2,5-difluorophenoxymethyl)-2-(((((1R)-1-(naphthalen-1-yl)ethyl)amino)carbonyl)phenyl)propanoic acid,
(24) 3-(4-(2-fluoro-5-methylphenoxymethyl)-2-(((((1R)-1-(naphthalen-1-yl)ethyl)amino)carbonyl)phenyl)propanoic acid,
(25) 3-(2-(((4-(3,5-dimethylphenyl)tetrahydro-2H-pyran-4-yl)amino) carbonyl)-4-(2-fluoro-5-methylphenoxymethyl)phenyl)propanoic acid,
(26) 3-(4-(2-fluoro-5-methylphenoxymethyl)-2-(((4-(3-methylphenyl)tetrahydro-2H-pyran-4-yl)amino)carbonyl)phenyl)propanoic acid,
(27) 3-(2-(((4-(benzofuran-2-yl)tetrahydro-2H-pyran-4-yl)amino)carbonyl)-4-(2,5-difluorophenoxymethyl)phenyl)propanoic acid,
(28) 3-(2-(((((1R)-1-(3,5-dimethylphenyl)-3-methylbutyl)amino)carbonyl)-4-(4-fluoro-2-methylphenoxymethyl)phenyl)propanoic acid,
(29) 3-(2-(((((1R)-1-(3,5-dimethylphenyl)-3-methylbutyl)amino)carbonyl)-4-((2-methylpyridin-3-yl)oxymethyl)phenyl)propanoic acid,
(30) 3-(2-(((((1R)-1-(3,5-dimethylphenyl)-3-methylbutyl)amino)carbonyl)-4-((2-methylpyridin-5-yl)oxymethyl)phenyl)propanoic acid,
(31) 3-(4-(3-fluorophenoxymethyl)-2-(((4-(naphthalen-2-yl)tetrahydro-2H-pyran-4-yl)amino)carbonyl)phenyl)propanoic acid,
(32) 3-(4-(3-methylphenoxymethyl)-2-(((4-(naphthalen-2-yl)tetrahydro-2H-pyran-4-yl)amino)carbonyl)phenyl)propanoic acid,
(33) 3-(4-(2,5-dimethyl phenoxymethyl)-2-(((4-(2-phenylethyl)tetrahydro-2H-pyran-4-yl)amino)carbonyl)phenyl)propanoic acid,
(34) 3-(2-(((4-(benzofuran-2-yl)tetrahydro-2H-pyran-4-yl)amino)carbonyl)-4-(2,5-dimethylphenoxymethyl)phenyl)propanoic acid,
(35) 3-(2-(((4-(benzothiophen-2-yl)tetrahydro-2H-pyran-4-yl)amino)carbonyl)-4-(2,5-dimethylphenoxymetliyl)phenyl)propanoic acid,
(36) 3-(4-(2,5-difluorophenoxymethyl)-2-(((4-(2-(2-fluorophenyl)ethyl)tetrahydro-2H-pyran-4-yl)amino)carbonyl)phenyl)propanoic acid,
(37) 3-(4-(2,5-dimethylphenoxymethyl)-2-(((4-(2-(2-fluorophenyl)ethyl)tetrahydro-2H-pyran-4-yl)amino)carbonyl)phenyl)propanoic acid,
(38) 3-(4-(2,5-dimethylphenoxymethyl)-2-(((4-(2-(4-fluorophenyl)ethyl)tetrahydro-2H-pyran-4-yl)amino)carbonyl)phenyl)propanoic acid,
(39) 3-(4-(2,5-dimethylphenoxymethyl)-2-(((4-(2-(3-fluorophenyl)ethyl)tetrahydro-2H-pyran-4-yl)amino)carbonyl)phenyl)propanoic acid,
(40) 3-(4-(6-fluoroindol-1-ylmethyl)-2-(((4-(2-phenylethyl)tetrahydro-2H-pyran-4-yl)amino)carbonyl)phenyl)propanoic acid,
(41) 3-(4-(6-fluoroindol-3-ylmethyl)-2-(((4-(2-phenylethyl)tetrahydro-2H-pyran-4-yl)amino)carbonyl)phenyl)propanoic acid,
(42) 3-(4-(3-methylindol-1-ylmethyl)-2-(((4-(2-phenylethyl)tetrahydro-2H-pyran-4-yl)amino)carbonyl)phenyl)propanoic acid,
(43) 3-(4-(3-cyanophenoxymethyl)-2-(((4-(2-phenylethyl)tetrahydro-2H-pyran-4-yl)amino)carbonyl)phenyl)propanoic acid,
(44) 3-(4-(6-fluoroindol-1-ylmethyl)-2-(((4-(naphthalen-2-yl)tetrahydro-2H-pyran-4-yl)amino)carbonyl)phenyl)propanoic acid,
(45) 3-(4-(6-fluoroindol-3-ylmethyl)-2-(((4-(naphthalen-2-yl)tetrahydro-2H-pyran-4-yl)amino)carbonyl)phenyl)propanoic acid,

(46) 3-(4-(3-methyl indol-1-ylmethyl)-2-(((4-(naphthalen-2-yl)tetrahydro-2H-pyran-4-yl)amino)carbonyl)phenyl)propanoic acid,
(47) 3-(4-(6-fluoroindol-1-ylmethyl)-2-(((4-(2-(3-fluorophenyl)ethyl)tetrahydro-2H-pyran-4-yl)amino)carbonyl)phenyl)propanoic acid,
(48) 3-(2-(((4-(2-(3-fluorophenyl)ethyl)tetrahydro-2H-pyran-4-yl)amino)carbonyl)-4-(3-methylindol-1-ylmethyl)phenyl)propanoic acid,
(49) 3-(4-(3-cyanophenoxymethyl)-2-(((4-(2-(3-fluorophenyl)ethyl)tetrahydro-2H -pyran-4-yl)amino)carbonyl)phenyl)propanoic acid,
(50) 4-(4-(1,3-dioxaindan-5-yloxy)-2-((((1R)-1-(naphthalen-1-yl)ethyl)amino)carbonyl)phenyl)butanoic acid,
(51) 4-(4-(3-methylphenoxy)-2-((((1R)-1-(naphthalen-1-yl)ethyl)amino)carbonyl)phenyl)butanoic acid,
(52) 4-(4-(3-cyanophenoxy)-2-((((1R)-1-(naphthalen-1-yl)ethyl)amino)carbonyl)phenyl)butanoic acid,
(53) 4-(4-(3,4-dimethylphenoxy)-2-((((1R)-1-(naphthalen-1-yl)ethyl)amino)carbonyl)phenyl)butanoic acid,
(54) 4-(4-(indan-5-yloxy)-2-((((1R)-1-(naphthalen-1-yl)ethyl)amino)carbonyl)phenyl)butanoic acid,
(55) 4-(4-(3,5-dimethylphenoxy)-2-((((1R)-1-(naphthalen-1-yl)ethyl)amino)carbonyl)phenyl)butanoic acid,
(56) 4-(4-(3-methylthiophenoxy)-2-((((1R)-1-(naphthalen-1-yl)ethyl)amino)carbonyl)phenyl)butanoic acid,
(57) 3-(2-((((1R)-1-(3,5-dimethylphenyl)-3-methylbutyl)amino)carbonyl)-4-(3-fluorophenylamino)phenyl)propanoic acid,
(58) 3-(2-((((1R)-1-(3,5-dimethylphenyl)-3-methylbutyl)amino)carbonyl)-4-(3-methylphenylamino)phenyl)propanoic acid,
(59) 3-(4-(3-cyanophenylamino)-2-((((1R)-1-(3,5-dimethylphenyl)-3-methylbutyl)amino)carbonyl)phenyl)propanoic acid,
(60) 3-(4-(3,5-difluorophenylamino)-2-((((1R)-1-(3,5-dimethylphenyl)-3-methylbutyl)amino)carbonyl)phenyl)propanoic acid,
(61) 3-(2-((((1R)-1-(3,5-dimethylphenyl)-3-methylbutyl)amino)carbonyl)-4-(1,3-dioxaindan-5-ylamino)phenyl)propanoic acid,
(62) 3-(4-(3,5-difluorophenoxy)-2-((((1R)-1-(3,5-dimetliylphenyl)-3-methylbutyl)amino)carbonyl)phenyl)propanoic acid,
(63) 3-(4-(3-cyanophenoxy)-2-((((1R)-1-(3,5-dimethylphenyl)-3-methylbutyl)amino)carbonyl)phenyl)propanoic acid,
(64) 4-(4-(3,5-dimethyl phenoxy)-2-((((1R)-1-(naphthalen-2-yl)ethyl)amino)carbonyl)phenyl)butanoic acid,
(65) 3-(4-(3,5-dimethylphenoxy)-2-((((1R)-1-(naphthalen-1-yl)ethyl)amino)carbonyl)phenyl)propanoic acid,
(66) 3-(4-(3,5-dimethylphenoxy)-2-((((1R)-1-(naphthalen-2-yl)ethyl)amino)carbonyl)phenyl)propanoic acid,
(67) 3-(4-(3,5-dimethylphenoxy)-2-((((1R)-1-(3-methylphenyl)-3-methylbutyl)amino)carbonyl)phenyl)propanoic acid,
(68) 3-(4-(3-methylphenylamino)-2-(((4-(naphthalen-2-yl)tetrahydro-2H-pyran-4-yl)amino)carbonyl)phenyl)propanoic acid,
(69) 4-(4-(3-fluorophenylamino)-2-((((1R)-1-(naphthalen-1-yl)ethyl)amino)carbonyl)phenyl)butanoic acid,
(70) 4-(4-(3-methylphenylamino)-2-((((1R)-1-(naphthalen-1-yl)ethyl)amino)carbonyl)phenyl)butanoic acid,
(71) 4-(4-(3,5-difluorophenylamino)-2-((((1R)-1-(naphthalen-1-yl)ethyl)amino)carbonyl)phenyl)butanoic acid,
(72) 4-(4-(1,3-dioxaindan-5-ylamino)-2-((((1R)-1-(naphthalen-1-yl)ethyl)amino)carbonyl)phenyl)butanoic acid,
(73) 4-(4-(3-cyanophenylamino)-2-((((1R)-1-(naphthalen-1-yl)ethyl)amino)carbonyl)phenyl)butanoic acid,
(74) 3-(4-(3,5-dimethylphenylamino)-2-((((1R)-1-(naphthalen-1-yl)ethyl)amino)carbonyl)phenyl)propanoic acid,
(75) 3-(4-(3,5-dimethylphenylamino)-2-((((1R)-1-(naphthalen-2-yl)ethyl)amino)carbonyl)phenyl)propanoic acid,
(76) 3-(4-(3,5-dimethylphenylamino)-2-(((4-(3,5-dimethylphenyl)tetrahydro-2H-pyran-4-yl)amino)carbonyl)phenyl)propanoic acid,
(77) 3-(4-(3,5-dimethylphenylamino)-2-(((4-(3-methylphenyl)tetrahydro-2H-pyran-4-yl)amino)carbonyl)phenyl)propanoic acid,
(78) 3-(4-(3,5-dimethyl phenoxy)-2-(((4-(3-methylphenyl)tetrahydro-2H-pyran-4-yl)amino)carbonyl)phenyl)propanoic acid,
(79) 3-(2-(((4-(benzofuran-2-yl)tetrahydro-2H-pyran-4-yl)amino)carbonyl)-4-(3,5-dimethylphenoxy)phenyl)propanoic acid,
(80) 3-(2-(((4-(benzofuran-2-yl)tetrahydro-2H-pyran-4-yl)amino)carbonyl)-4-(3,5-dimethylphenylamino)phenyl)propanoic acid,
(81) 3-(4-(3,5-dimethylphenoxy)-2-(((4-(2-phenylethyl)tetrahydro-2H-pyran-4-yl)amino)carbonyl)phenyl)propanoic acid,
(82) 3-(4-(3,5-dimethylphenoxy)-2-(((4-(3,5-dimethylphenyl)tetrahydro-2H-pyran-4-yl)amino)carbonyl)phenyl)propanoic acid,
(83) 3-(4-(3,5-dimethylphenylamino)-2-(((4-(2-phenylethyl)tetrahydro-2H-pyran-4-yl)amino)carbonyl)phenyl)propanoic acid,
(84) 3-(2-(((4-(3,5-dimethylphenyl)tetrahydro-2H-pyran-4-yl)amino)carbonyl)-4-(3-methylphenylamino)phenyl)propanoic acid,
(85) 3-(2-(((4-(benzothiophen-2-yl)tetrahydro-2H-pyran-4-yl)amino)carbonyl)-4-(3,5-dimethylphenylamino)phenyl)propanoic acid,
(86) 3-(4-(3,5-dimethylphenoxy)-2-(((4-(2-(4-fluorophenyl)ethyl)tetrahydro-2H-pyran-4-yl)amino)carbonyl)phenyl)propanoic acid,
(87) 3-(4-(3,5-dimethylphenylamino)-2-(((4-(2-(4-fluorophenyl)ethyl)tetrahydro-2H -pyran-4-yl)amino)carbonyl)phenyl)propanoic acid,
(88) 3 (4-(3,5-dimethylphenylamino)-2-(((4-(2-(2-fluorophenyl)ethyl)tetrahydro-2H -pyran-4-yl)amino)carbonyl)phenyl)propanoic acid,
(89) 3-(4-(3,5-dimethylphenoxy)-2-(((4-(2-(2-fluorophenyl)ethyl)tetrahydro-2H-pyran-4-yl)amino)carbonyl)phenyl)propanoic acid or
(90) 3-(4-(3,5-dimethylphenoxy)-2-(((4-(2-(3-fluorophenyl)ethyl)tetrahydro-2H-pyran-4-yl)amino)carbonyl)phenyl)propanoic acid,
a salt thereof, a solvate thereof or a prodrug thereof 3) The carboxylic acid compound according to the above 1), which is
(1) 3-(2-((((1R)-1-(3,5-dimethylphenyl)-3-methylbutyl)amino)carbonyl)-4-(5-fluoro-2-methylphenoxymethyl)phenyl)propanoic acid,
(2) 3-(2-(((4-(benzothiophen-2-yl)tetrahydro-2H-pyran-4-yl)amino)carbonyl)-4-(2,5-difluorophenoxymethyl)phenyl)propanoic acid,
(3) 3-(4-(2-fluoro-5-methylphenoxymethyl)-2-((((1R)-3-methyl-1-(3-methyl phenyl)butyl)amino)carbonyl)phenyl)propanoic acid,
(4) 3-(4-(2,5-difluorophenoxymethyl)-2-(((4-(2-(3-fluorophenyl)ethyl)tetrahydro-2H-pyran-4-yl)amino)carbonyl)phenyl)propanoic acid, (5) 3-(4-(3,5-dimethylphenylamino)-2-(((4-(naphthalen-2-yl)tetrahydro-2H-pyran-4-yl)amino)carbonyl)phenyl)propanoic acid,
(6) 3-(2-(((4-(benzothiophen-2-yl)tetrahydro-2H-pyran-4-yl)amino)carbonyl)-4-(3,5-dimethylphenoxy)phenyl)propanoic acid,
(7) 3-(4-(2,5-difluorophenoxymethyl)-2-(((4-(2-phenylethyl)tetrahydro-2H-pyran-4-yl)amino)carbonyl)phenyl)propanoic acid,
(8) 3-(2-((((1R)-1-(3,5-dimethylphenyl)-3-methylbutyl)amino)carbonyl)-4-(3-pyridyloxymethyl)phenyl)propanoic acid,
(9) 3-(4-(2-fluoro-5-methylphenoxymethyl)-2-((((1R)-1-(3,5-dimethylphenyl)-3-methylbutyl)amino)carbonyl)phenyl)propanoic acid,
(10) 3-(4-(3,5-dimethylphenylamino)-2-((((1R)-1-(3,5-dimethylphenyl)-3-methylbutyl)amino)carbonyl)phenyl)propanoic acid,
(11) 3-(4-(6-fluoroindol-1-ylmethyl)-2-((((1R)-1-(3,5-dimethylphenyl)-3-methylbutyl)amino)carbonyl)phenyl)propanoic acid,
(12) 3-(4-(3,5-dimethylphenoxy)-2-(((4-(naphthalen-2-yl)tetrahydro-2H-pyran-4-yl)amino)carbonyl)phenyl)propanoic acid,
(13) 4-(4-(3,5-dimethylphenylamino)-2-((((1R)-1-(naphthalen-1-yl)ethyl)amino)carbonyl)phenyl)butanoic acid,
(14) 3-(4-(2-chloro-5-methylphenoxymethyl)-2-((((1R)-3-methyl-1-(3-methylphenyl)butyl)amino)carbonyl)phenyl)propanoic acid,
(15) 3-(4-(2,5-difluorophenoxymethyl)-2-(((4-(2-(4-fluorophenyl)ethyl)tetrahydro-2H-pyran-4-yl)amino)carbonyl)phenyl)propanoic acid,
(16) 3-(4-(3,5-dimethylphenylamino)-2-((((1R)-1-(3-methylphenyl)-3-methylbutyl)amino)carbonyl)phenyl)propanoic acid,
(17) 3-(4-(2-fluoro-5-methylphenoxymethyl)-2-(((4-(naphthalen-2-yl)tetrahydro-2H-pyran-4-yl)amino)carbonyl)phenyl)propanoic acid,
(18) 3-(4-(3,5-dimethylphenoxy)-2-((((1R)-1-(3,5-dimethylphenyl)-3-methylbutyl)amino)carbonyl)phenyl)propanoic acid or
(19) 3-(4-(3,5-dimethylphenylamino)-2-(((4-(2-(3-fluorophenyl) ethyl)tetrahydro-2H-pyran-4-yl)amino)carbonyl)phenyl)propanoic acid, a salt thereof, a solvate thereof or a prodrug thereof
4) A pharmaceutical composition, which comprises the carboxylic acid compound according to the above 1), a salt thereof, a solvate thereof or a prodrug thereof
5) The pharmaceutical composition according to the above 4), which is $EP_3$ receptor antagonist.
6) The pharmaceutical composition according to the above 5), which is a preventive and/or therapeutic agent for diseases induced by excess activation of $EP_3$ receptor.
7) The pharmaceutical composition according to the above 6), wherein the diseases induced by excess activation of $EP_3$ receptor are one or more selected from pruritis, pain, urinary disturbance and stress-related disease.
8) The pharmaceutical composition according to the above 7), wherein the pain is arthritis pain or neuropathic pain.
9) The pharmaceutical composition according to the above 7), wherein the urinary disturbance is urinary frequency.
10) A pharmaceutical composition, which comprises the carboxylic acid compound according to the above 1), a salt thereof, a solvates thereof or a prodrug thereof, and one or more medicaments selected from steroid drugs, non-steroidal antiinflammatory drugs, immunosuppressants, anti-allergic drugs, mediator-release inhibitors, leukotriene receptor antagonists, antihistamine drugs, forskolin preparations, phosphodiesterase inhibitors, nitric oxide synthase inhibitors, cannabinoid-2 receptor stimulators, nonopioid analgesics, nonsteroidal analgesics, cyclooxygenase inhibitors, opioid analgesics, prostaglandins, N-type calcium channel blockers, α1 adrenaline receptor blockers, progesterone preparations, anticholinergic agents, muscarine receptor antagonists, $5-HT_{1A}$ receptor agonists, σ1 receptor agonists, serotonin nervous system agonists, corticotropin releasing factor receptor antagonists, proton pump inhibitors, M1 receptor antagonists, cytoprotective agents, tricyclic antidepressants and tetracyclic antidepressants.

11) A method for preventing and/or treating diseases induced by excess activation of $EP_3$ receptor in a mammal, which comprises administering to a mammal an effective amount of the carboxylic acid compound according to the above 1), or a salt thereof, a solvate thereof or a prodrug thereof 12) Use of the carboxylic acid compound according to the above 1), or a salt thereof, a solvate thereof or a prodrug thereof in the manufacture of a medicament for prevention and/or treatment of diseases induced by excess activation of $EP_3$ receptor.

In the present invention, C1-4 alkyl includes methyl, ethyl, propyl, butyl and isomers thereof.

In the present invention, C1-4 alkylthio includes methylthio, ethylthio, propylthio, butylthio and isomers thereof.

In the present invention, the halogen includes fluoride, chloride, bromide and iodide.

In the present invention, preferable $R^1$ is hydrogen, methyl or ethyl.

In the present invention, preferable n is 0 or 2.

In the present invention, a preferable substituent of ring represented by $R^2$ is methyl or fluoride.

In the present invention, preferable $R^{3a}$ and $R^{3b}$ each independently is hydrogen, methyl, isobutyl, or tetrahydro-2H-pyran which represented by $R^{3a}$ and $R^{3b}$ with the carbon atom to which they are attached. More specifically, as a group

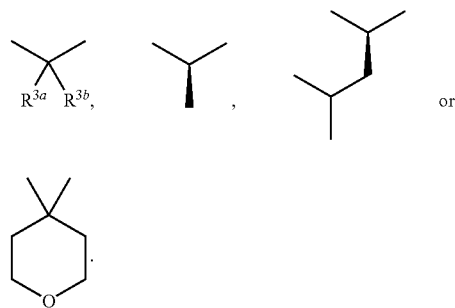

is a preferable group.

In the present invention, preferable $R^4$ is methyl, thiomethyl, fluoride, chloride or cyano.

Unless otherwise specified, the present invention includes all isomers. For example, alkyl includes straight or branched ones. In addition, the present invention also include isomers on double bond, ring, fused ring (E-, Z-, cis-, trans-), isomers generated from asymmetric carbon atoms (R-, S-, α-, β-configuration, enantiomer, diastereomer), optically active isomers (D-, L-, d-, l-), polar compounds generated by chromatographic separation (more polar compound, less polar compound), equilibrium compounds, rotational isomers, mixtures thereof at any ratios and racemic mixtures.

In the present invention, concrete compounds are the compounds described in examples and a pharmaceutically acceptable salt.

Salt:

The compound of the present invention may be converted into a corresponding a pharmaceutically acceptable salt by known methods. Non-toxic and water-soluble salts are preferable. In the present invention, salts are salts of alkali metals, such as potassium, sodium, etc.; salts of alkaline-earth metals, such as calcium, magnesium, etc.; ammonium salts, pharmaceutically acceptable organic amines, such as tetramethylammonium, triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.

In the present invention, preferable acid addition salts are non-toxic and water-soluble salts. In the present invention, acid addition salts are salts of inorganic acids such as hydrochloride, hydrobromide, sulfate, phosphate, nitrate; salts of organic acids e.g., acetate, lactate, tartrate, oxalate, fumarate, maleate, citrate, benzoate, methanesulphonate, ethanesulphonate, benzenesulphonate, toluenesulphonate, isethionate, glucuronate, gluconate.

The compound of the present invention and a pharmaceutically acceptable salt thereof may be converted into the corresponding hydrates by conventional means.

Preparation of the Compound of the Present Invention:

The present compound of formula (I) may be prepared, for example, by the following method.

(1) In the compound of formula (I), wherein $R^1$ is hydrogen, that is, the compound of formula (Ia):

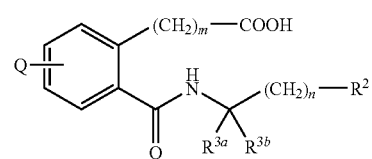

wherein all symbols have the same meanings as described above;

may be prepared by subjecting to deprotection under alkaline conditions the compound of formula (Ib):

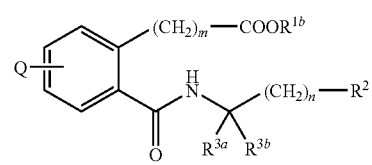

wherein $R^{1b}$ is C1-4 alkyl and the other symbols have the same meanings as described above.

Deprotection under alkaline conditions is known, for example it may be carried out in water-miscible organic solvent (e.g., methanol, ethanol, tetrahydrofuran, dioxane or a mixture thereof), using an aqueous solution of alkali (e.g., sodium hydroxide, potassium hydroxide or potassium carbonate) at form −10 to 90° C.

The compound represented by formulae (Ib) may be prepared, for example, by methods in accordance with the following reaction schemes A-D.

Scheme A

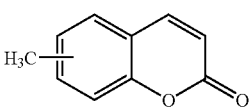

(VIII)

halogenation ↓

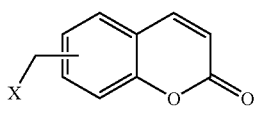

(VII)

Cyc1-OH
or
Cyc2-H

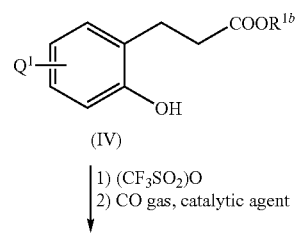

(IV)

1) $(CF_3SO_2)_2O$
2) CO gas, catalytic agent

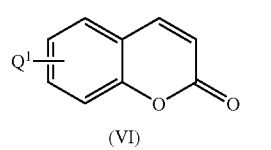
(VI)
↓ NaOR$^{1b}$
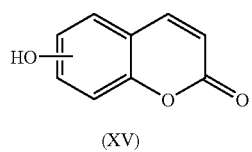
(V)
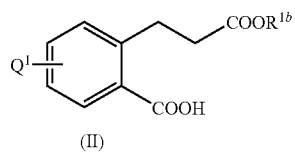
(II)
↓ 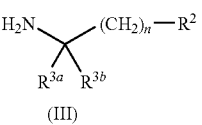
(III)
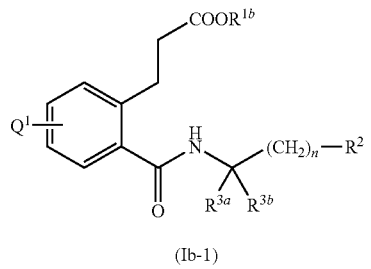
(Ib-1)
Scheme B
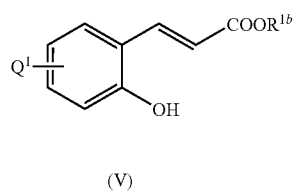
(XV)
↓ introduction of a protecting group
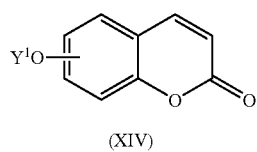
(XIV)
↓ NaOR$^{1b}$
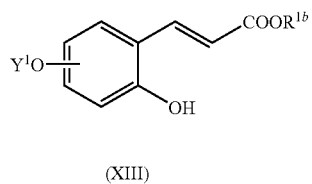
(XIII)
↓ reduction
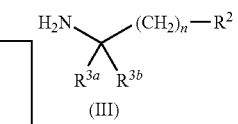
(III)
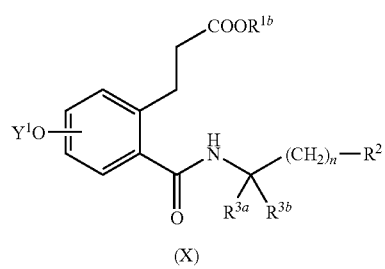
(X)
↓ deprotection

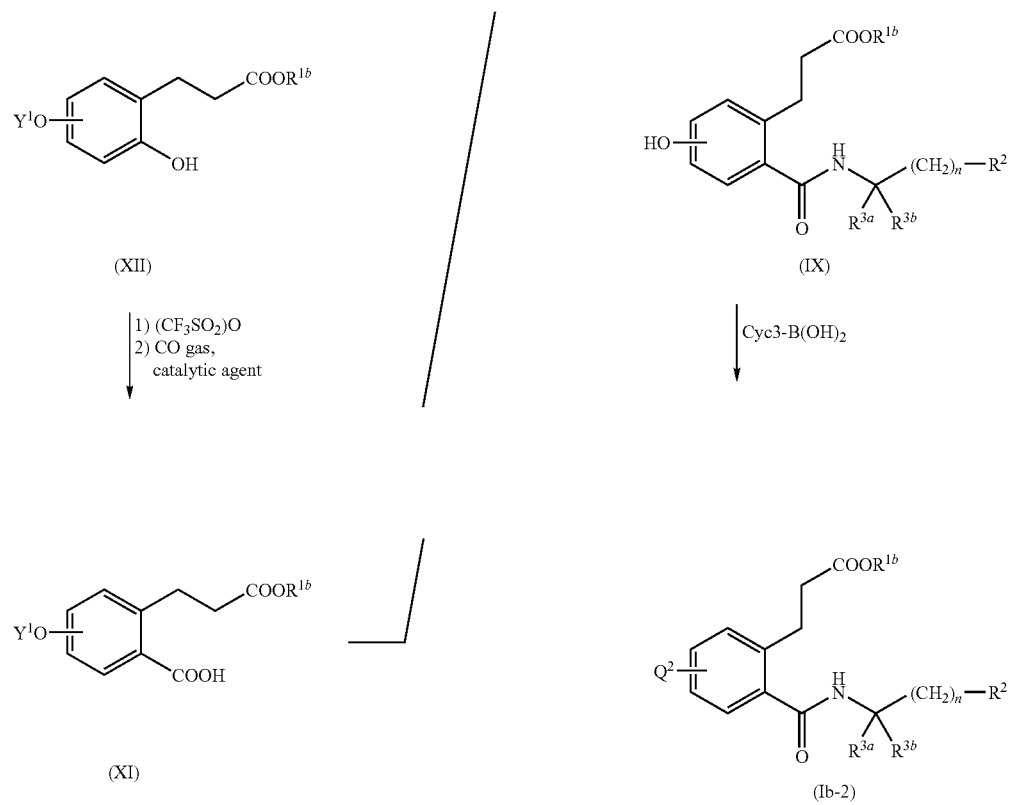
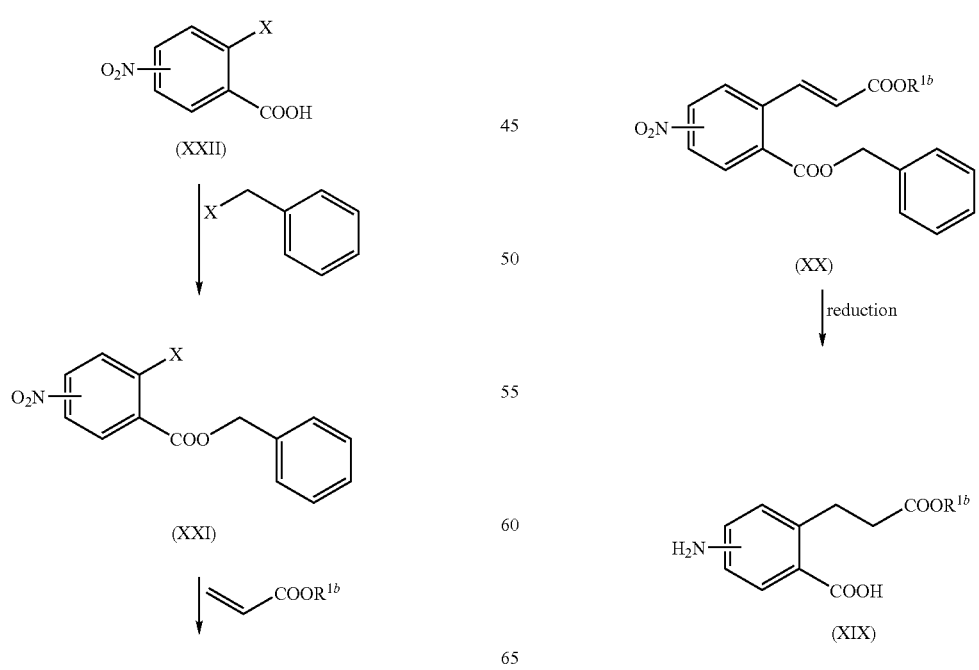

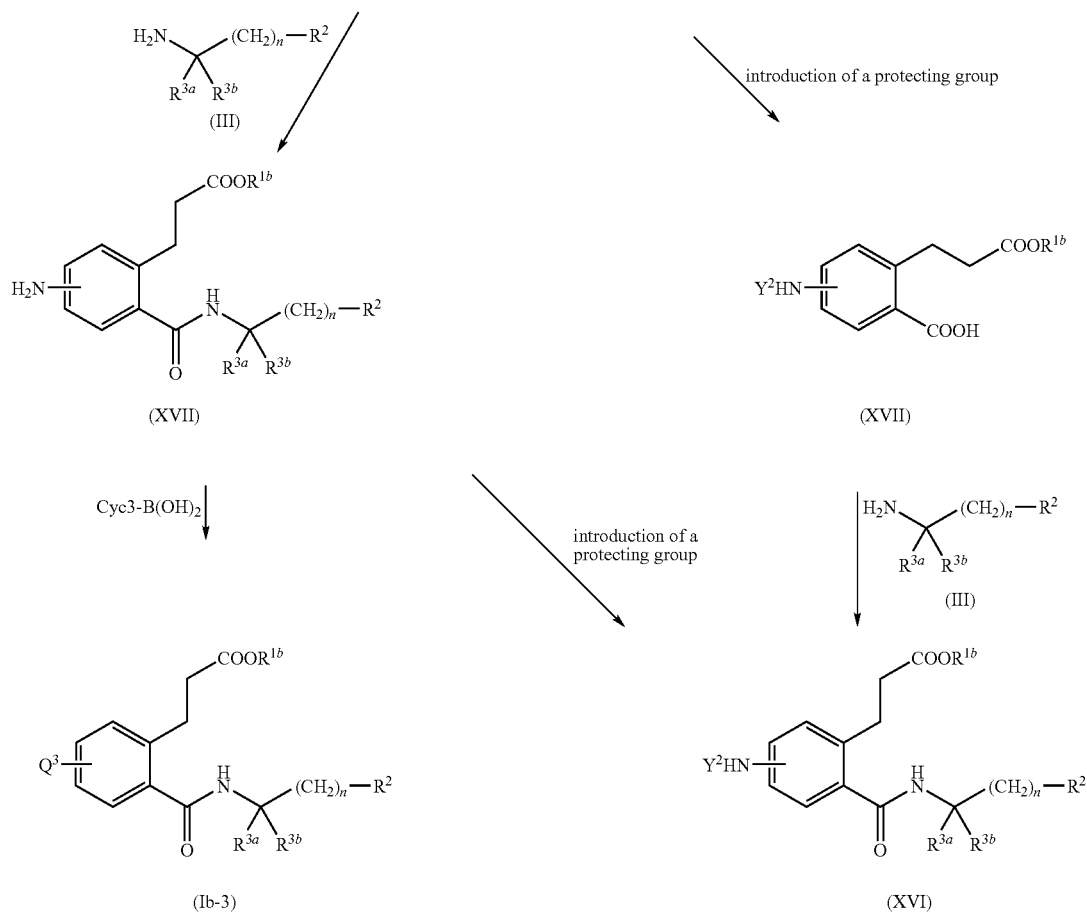
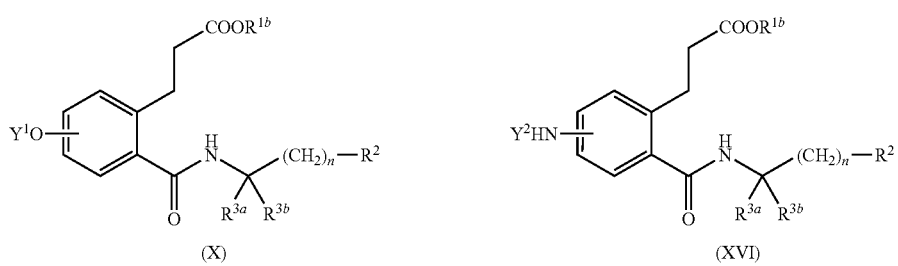

-continued

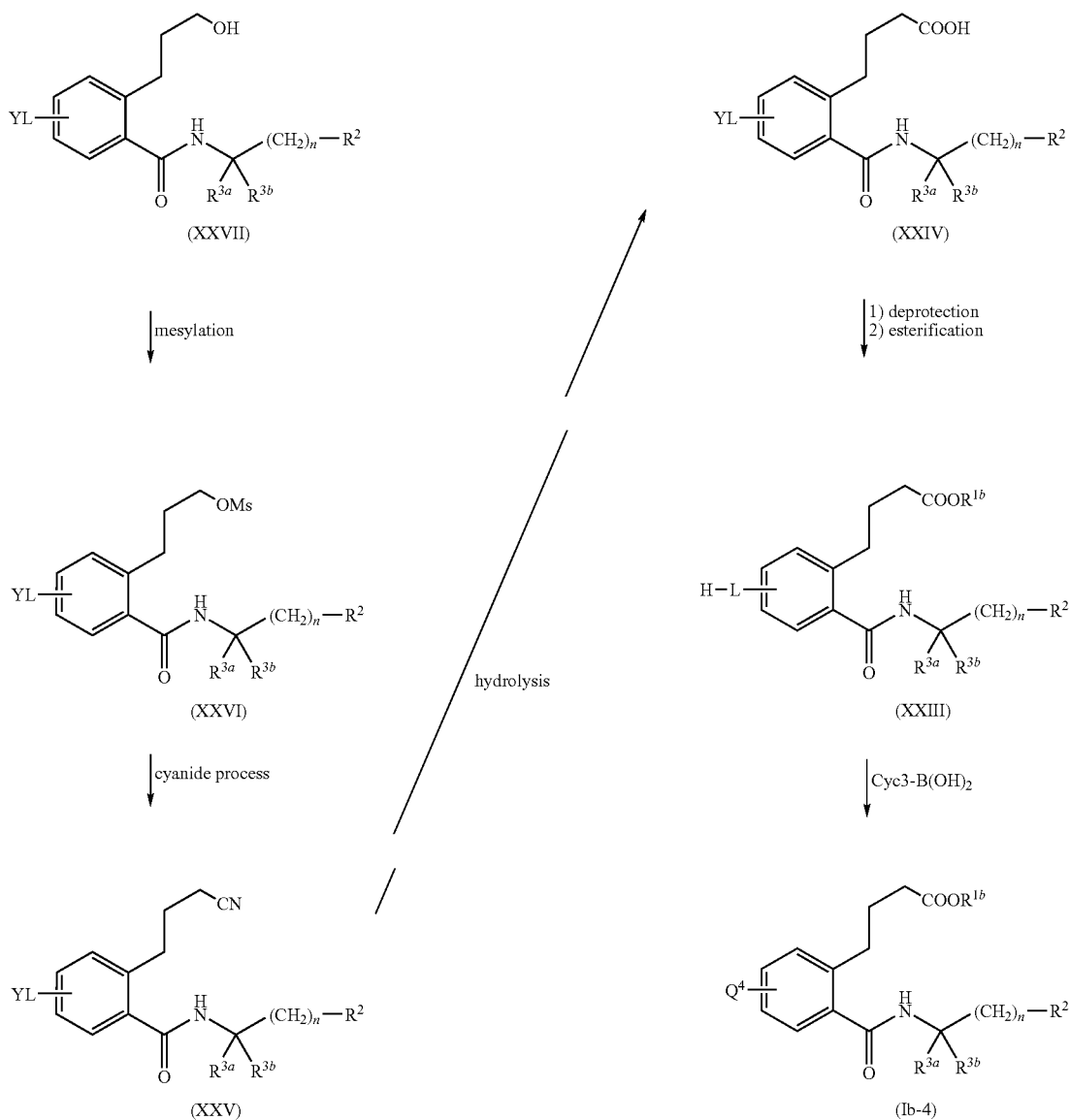

In the schemes,
$Q^1$ is (i) —CH$_2$—O-Cyc1 or (ii) —CH$_2$-Cyc2;
$Q^2$ is (iii-1) —O-Cyc3;
$Q^3$ is (iii-2) —NH-Cyc3;
$Q^4$ is (iii) -L-Cyc3;
$Y^1$ is a protecting group of hydroxyl;
$Y^2$ is a protecting group of amino;
Ms is mesyl;
Tf is trifluoromethylsulfonyl;
X is halogen;
The other symbols have the same meanings as described above.

Toxicity:

It has been confirmed that the compounds of the present invention have sufficiently low toxicity and thus are safe enough in using as drugs.

INDUSTRIAL APPLICABILITY

Application to Drugs:

The compounds of the present invention show an antagonizing activity by binding to an PGE$_2$ receptor, particularly to a subtype EP$_3$, and therefore, they are considered to be useful for prevention and/or treatment of, for example, pain (e.g., arthritic pain, cancerous pain, pain upon bone fracture, pain upon operation, pain after tooth extraction, neuropathic pain, allodynia, hyperalgesia, pain after herpes, etc.), itching, urticaria, atopic dermatitis, contact dermatitis, allergic conjunctivitis, various symptoms upon dialysis, asthma, rhinitis, sneeze, pollakiuria, cystitis, neurogenic bladder, urinary disturbance, ejaculatory disturbance, defervescence, systemic inflammation reaction, learning disability, Alzheimer's disease, generation of cancer, proliferation of cancer, metastasis of cancer to organs, retinopathy, skin erythema, thermal injury, burn, steroidal burn, renal insufficiency, renal disease, acute nephritis, chronic nephritis, blood electrolyte abnormality, threatened early delivery, threatened abortion, hypermenorrhea, dysmenorrhea, endometriosis, premenstrual syndrome, genital disorder, stress disease, anxiety, melancholia, manic-depression, psychosomatic disorder, panic disorder, mental disorder, thrombosis, embolism, transient ischemic attack, cerebral infarction, atheromatosis, organ transplantation, cardiac infarction, cardiac insufficiency, hypertension, arteriosclerosis, circulation disorder and ulcer accompanied thereby, neuropathy, vascular dementia, edema, various arthritis diseases, synovitis, rheumatism, osteoarthritis, diarrhea, constipation, disturbance of bile discharge, ulcerative colitis and Crohn's disease.

Preferably, they are considered to be more effective for prevention and/or treatment of pain (arthritic pain, neuropathic pain), itching, urinary disturbance or stress diseases.

Examples of the arthritic pain include rheumatism, osteoarthritis and pain accompanied by synovitis.

Examples of the neuropathic pain include herpes zoster neuralgia, postherpetic neuralgia, reflexive sympathetic atrophy, causalgia, pain after thoracotomy, phantom limb pain, thalamus pain, cancerous pain, pain after bone fracture, external injury or burn, glossodynia (intraoral burning syndrome) and trigeminal neuralgia.

Examples of the urinary disturbance include pollakiuria, for example, pollakiuria associated with neuropathic bladder, neurogenic bladder, stimulated bladder, instable bladder and prostatism.

Examples of the stress diseases include stress disturbance after psychic trauma, stress gastritis, stress ulcer, irritable bowel syndrome, stress asthma, stress alopecia, stress psychic disorder, melancholia, psychosomatic disorder, panic disorder, stress insomnia, stress hypertension, stress headache, stress amenorrhea, stress constipation, stress overeating disease or food refusal and stress genital function insufficiency.

A combination agent obtained by combining the present compound or a salt thereof with other medicaments may be administered to accomplish the following purposes:
1) to supplement and/or enhance the preventive and/or therapeutic effect of the present compound;
2) to improve the kinetics and/or absorption and reduce the dose of the present compound; and/or
3) to eliminate the side effects of the present compound.

A combination of the present compound and other medicaments may be administered in the form of the formulations having these components incorporated in one preparation, or may be administered in separate preparations. In the case where these medicaments are administered in separate preparations, they may be administered simultaneously or at different times. In the latter case, the present compound may be administered before the other medicaments. Alternatively, the other medicaments may be administered before the present compound. The method for the administration of these medicaments are the same or different.

The diseases on which the preventive and/or therapeutic effect of the above mentioned combination preparations works are not specifically limited but may be those for which the preventive and/or therapeutic effect of the present compound is supplemented and/or enhanced.

Examples of other drugs for supplementing and/or enhancing the preventive and/or therapeutic effect of the present compounds on itching, urticaria, atopic dermatitis, contact dermatitis, allergic conjunctivitis, various symptoms upon dialysis, include steroid drugs, nonsteroidal anti-inflammatory drugs, immunosuppressants, antiallergic drugs, mediator release inhibitors, leukotriene receptor antagonists, antihistamines, forskolin preparations, phosphodiesterase inhibitors, nitric oxide synthase inhibitors, cannabinoid-2 receptor stimulators, and the like.

Examples of other drugs for supplementing and/or enhancing the preventive and/or therapeutic effect of the present compounds on pain, include nonopioid analgesics, such as nonsteroidal anti-inflammatory drugs, cyclooxygenase (COX) inhibitors; opioid analgesics, prostaglandins, N-type calcium channel blockers, nitric oxide synthase inhibitors, cannabinoid-2 receptor stimulators, and the like.

Examples of other drugs for supplementing and/or enhancing the preventive and/or therapeutic effect of the present compounds on neuropathic pain, include, tricyclic antidepressants and tetracyclic antidepressants, and the like.

Examples of other drugs for supplementing and/or enhancing the preventive and/or therapeutic effect of the present compounds on urinary disturbance, include, other therapeutic agents for urinary disturbance, such as α1 adrenaline receptor blockers, progesterone preparations, anticholinergic agents and muscarine receptor antagonists, and the like.

Examples of other drugs for supplementing and/or enhancing the preventive and/or therapeutic effect of the present compounds on stress diseases, include, other therapeutic agents for stress diseases, such as $5\text{-HT}_{1A}$ receptor agonists, σ1 receptor agonists, serotonin nervous system agonists, corticotropin releasing factor (CRF) receptor antagonists, proton pump inhibitors, M1 receptor antagonists and cytoprotective agents, and the like.

Examples of other drugs for supplementing and/or enhancing the preventive and/or therapeutic effect of the present compounds on generation of cancer, proliferation of cancer, metastasis of cancer to organs, include, anticancer agents, analgesic drugs, metalloproteinase inhibitors, and the like.

Examples of the nonsteroidal anti-inflammatory drugs include sasapyrine, sodium salicylate, aspirin, aspirin dialuminate blend, diflunisal, indomethacin, sprofen, ufenamate, dimethylisopropylazulene, bufexamac, felbinac, diclofenac, tolmetin sodium, clinoril, fenbufen, nabumetone, proglumetacin, indometacin farnesil, acemetacin, proglumetacin maleate, amfenac sodium, mofezolac, etodolac, ibuprofen, ibuprofen piconol, naproxen, flurbiprofen, flurbiprofen axetil, ketoprofen, fenoprofen calcium, tiaprofen, oxaprozin, pyranoprofen, loxoprofen sodium, alminoprofen, zaltoprofen, mefenamic acid, aluminum mefenamate, tolfenamic acid, floctafenine, ketophenylbutazone, oxyfenbutazone, piroxicam, tenoxicam, ampiroxicam, napageln ointment, epirizol, tiaramide hydrochloride, tinoridine hydrochloride, emorfazone, sulpirin, migrenin, saridon, sedes G, amipylo N, sorbon, pilin-based cold drugs, acetaminophen, fenacetine, dimethothiazine mesylate, meloxicam, celecoxib, rofecoxib, valdecoxib, simetride-containing agents, non-pilin-based cold drugs, and the like.

Examples of the steroid drugs include, e.g., as drugs for external use, clobetasol propionate, diflorasone acetate, fluocinonide, mometasone furancarboxylate, betamethasone dipropionate, betamethasone butyrate propionate, betamethasone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate acetate, fluocinolone acetonide, beclomethasone propionate, triamcinolone acetonide, flumethasone pivalate, alclomethasone propionate, clobethasone butyrate, prednisolone, beclomethasone propionate, fludroxycortide, and the like.

Examples of drugs for internal use and injections include cortisone acetate, hydrocortisone, hydrocortisone sodium phosphate, hydrocortisone sodium succinate, fludrocortisone acetate, prednisolone, prednisolone acetate, prednisolone sodium succinate, prednisolone butyl acetate, prednisolone sodium phosphate, halopredone acetate, methylprednisolone, methylprednisolone acetate, methylprednisolone sodium succinate, triamcinolone, triamcinolone acetate, triamcinolone acetonide, dexamethasone, dexamethasone acetate, dexamethasone sodium phosphate, dexamethasone palmitate, paramethasone acetate, betamethasone, and the like.

Examples of inhalations include beclomethasone propionate, fluticasone propionate, budesonide, flunisolide, triamcinolone, ST-126P, ciclesonide, dexamethasone palomithionate, mometasone furoate, prasterone sulfonate, deflazacort, methylprednisolone sleptanate, methylprednisolone sodium succinate, and the like.

Examples of the immunosuppressants include protopic (FK-506), methotrexate, cyclosporin, ascomycin, leflunomide, bucillamine, salazosulfapyridine, and the like.

Examples of the mediator release inhibitors include tranilast, sodium cromoglycate, amlexanox, repirinast, ibudilast, tazanolast, pemirolast potassium and the like.

Examples of the leukotriene receptor antagonists include pranlukast hydrate, montelukast, zafirlukast, MCC-847, KCA-757, CS-615, YM-158, L-740515, CP-195494, LM-1484, RS-635, A-93178, S-36496, BIIL-284, ONO-4057, and the like.

Examples of the antihistamines include ketotifen fumarate, mequitazine, azelastine hydrochloride, oxatomide, terfenadine, emedastine fumarate, epinastine hydrochloride, astemizole, ebastine, cetirizine hydrochloride, bepotastine, fexofenadine, loratadine, desloratadine, olopatadine hydrochloride, TAK-427, ZCR-2060, NIP-530, mometasone furoate, mizolastine, BP-294, andolast, auranofin, acrivastine, and the like.

Examples of the anti-cancer agent include alkylating agents (e.g., nitrogen mustard N-oxide hydrochloride, cyclophosphamide, ifosfamide, melphalan, thiotepa, carboquone, busulfan, etc.), nitrosourea derivatives (e.g., nimustine hydrochloride, ranimustine, etc.), antimetabolites (e.g., methotrexate, mercaptopurine, 6-mercaptopurine riboside, fluorouracil, tegafur, UFT, carmofur, doxyfluridine, cytarabine, enocitabine, etc.), anti-cancer antibiotics (actinomycin D, mitomycin C, daunorubicin hydrochloride, doxorubicin hydrochloride, aclarubicin hydrochloride, neocarzinostatin, pirarubicin, epirubicin, idarubicin, chromomycin A3, bleomycin, peplomycin sulfate, etc.), plant alkaloids (e.g., vunblastin sulfate, vincristine sulfate, vindesine sulfate, etc.), hormone agents (e.g., sodium estramustine sulfate, mepitiostane, epitiostanol, tamoxifen citrate, diethylstilbestrol phosphate, medroxyprogesterone acetate, anastrozole, fadrozole, leuprolide, etc.), immunopotentiators (e.g., lentinan, picibanil, Krestin, schizophyllan, ubenimex, interferon, etc.) and others (e.g., L-asparaginase, procarbazine hydrochloride, mitoxantrone hydrochloride, cisplatin, carboplatin, etc.).

Examples of the phosphodiesterase inhibitors include PDE4 inhibitors such as roliplam, cilomilast (trade name: Ariflo), Bay 19-8004, NIK-616, roflumilast (BY-217), cipamfylline (BRL-61063), atizoram (CP-80633), SCH-351591, YM-976, V-11294A, PD-168787, D-4396, IC-485, and the like.

Examples of the non-opioid analgesic agents include nonsteroidal anti-inflammatory analgesic agents (e.g., aspirin, alminoprofen, flurbiprofen axetil, suprofen, disodium lobenzarit, tenoxicam, loxoprofen sodium, perbiprofen, flurbiprofen, piroxicam, indomethacin farnesil, pranoprofen, sulindac, indomethacin, nabumetone, etodolac, phenacetin, naixan, diclofenac sodium, etc.), cyclooxygenase (COX) inhibitors (e.g., zaltoprofen, nimesulide, zaltoprofen, zoliprofen, oxaprozin, miroprofen, ketoprofen, amtolmetin guacil, mofezolac, lornoxicam, meloxicam, ainpiroxicam, aceclofenac, celecoxib, parecoxib, etoricoxib, etc.), steroidal analgesic agents (e.g., rimexolone, prednisolone, etc.), sodium hyaluronate, auranofin, ipriflavone, orgotein, actarit, subreum, salazosulfapyridine and leflunomide, and the like.

Examples of the analgesic agents of an opiold type include codeine phosphate, buprenorphine hydrochloride, pentazocine hydrochloride, morphine (morphine hydrochloride and morphine sulfate), fentanyl, pethidine hydrochloride and levorphanol, and the like.

Examples of the tricyclic antidepressants include imipramine hydrochloride, desipramine hydrochloride, clomipramine hydrochloride, trimipramine maleate, amitriptyline hydrochloride, nortriptyline hydrochloride, lofepramine hydrochloride, amoxapine, dosulepin hydrochloride, gabapentin, mexiletine, clonidine and ketamine, and the like.

Examples of the tetracyclic antidepressants include maprotiline and mianserin, and the like.

Examples of other therapeutic agents for urinary disturbance are terazosin hydrochloride, urapidil, froxiprost, tamsulosin hydrochloride, prazosin hydrochloride, allylestrenol, oxybutynin hydrochloride, terodiline hydrochloride, propiverine hydrochloride, naftopidil, chlormadinone acetate, mesna, alfuzosin, NC-1800, tolterodine, silodosin, fiduxosin, trospium chloride, TF-505, R-701, R-1554, TAK-802 and solifenacin, and the like.

Examples of other therapeutic agents for stress diseases are tandospirone citrate, lesopitron, igmesine, AP-521, PLD-116, ilaprazole, ME-3412, DMP-696, ME-3412, YJA-20379-8, pirenzepine hydrochloride, lansoprazole, dosmalfate and osemozotan, and the like.

The weight ratio of the present compound and the other medicaments is not specifically limited.

Any combination of two or more other medicaments may be administered.

Furthermore, the other medicaments for supplementing and/or enhancing the preventive and/or therapeutic effect of the present compound include not only those found so far but also those which will be found on the basis of the above mentioned mechanism.

For the purpose above described, the present compound, or a combination of the present compound and other medicaments may be normally administered systemically or locally, usually by oral or parenteral administration.

The doses to be administered are determined depending upon, for Example, ages, body weights, symptoms, the desired therapeutic effects, the route of administration and the duration of the treatment. For the human adult, the doses per person are generally from 1 µg to 10 g, by oral administration, up to several times per day, and from 0.1 µg to 1 g, by parenteral administration, up to several times per day, or continuous administration 1 to 24 hours per day from vein.

As mentioned above, the doses to be used depend upon various conditions. Therefore, there are cases in which doses lower than or greater than the ranges specified above may be used:

To administer the present compound, or a combination of the present compound and other medicaments, use is made of solid preparations for internal use and liquid preparations for internal use for oral administration as well as preparations for injections, external preparations, suppositories, eye drops, inhalations and the like for parenteral administration.

Examples of the solid preparations for internal use for oral administration include tablets, pills, capsules, powders, granules and the like. The capsules include hard capsules and soft capsules.

Such a solid preparation for internal use is prepared by a formulation method commonly employed by using one or two or more active substances either as it is or as a mixture with an excipient (lactose, mannitol, glucose, microcrystalline cellulose, starch, etc.), a binder (hydroxypropylcellulose, polyvinylpyrrolidone, magnesium metasilicate aluminate, etc.), a disintegrating agent (calcium cellulose glycolate, etc.), a lubricant (magnesium stearate, etc.), a stabilizer and a dissolution aid (glutamic acid, aspartic acid, etc.). If necessary, it may be coated with a coating agent (sucrose, gelatin, hydroxypropylcellulose, hydroxypropylmethylcellulose phthalate, etc.). It may be coated with two or more layers. Moreover, capsules made of an absorbable material such as gelatin are involved in the scope thereof.

The liquid preparations for internal use for oral administration include pharmaceutically acceptable aqueous solutions, suspensions, emulsions, syrups, elixirs and the like. Such a liquid preparation is prepared by dissolving, suspending or emulsifying one or more active substances in a diluent commonly employed (purified water, ethanol or a mixture thereof, etc.). Such liquid forms may also further comprise some additives such as humectants, suspending agents, emulsifying agents, sweetening agents, flavoring agents, aroma, preservatives, buffers and the like.

The dosage forms of the parenteral administration preparations for external use include ointments, gels, creams, fomentations, patches, liniments, atomized agents, inhalations, sprays, aerosols, nasal drops and the like. Such a preparation contains one or two or more active substances and is prepared by a well known method or a commonly employed formulation.

Ointments are prepared in accordance with a well known formulation or a commonly employed formulation. For example, they are prepared by softening or melting one or two or more active substances in a base. The ointment base is selected from well known ones or those commonly employed. For example, use may be made of one base or a mixture of two or more thereof selected from higher fatty acids or higher fatty acid esters (adipic acid, myristic acid, palmitic acid, stearic acid, oleic acid, adipic acid esters, myristic acid esters, palmitic acid esters, stearic acid esters, oleic acid esters, etc.), waxes (beeswax, whale wax, ceresin, etc.), surfactants (polyoxyethylene alkyl ether phosphoric acid esters, etc.), higher alcohols (cetanol, stearyl alcohol, cetostearyl alcohol, etc.), silicone oils (dimethylpolysiloxane, etc.), hydrocarbons (hydrophilic vaseline, white vaseline, refined lanolin, liquid paraffin, etc.), glycols (ethylene glycol, diethylene glycol, propylene glycol, polyethylene glycol, macrogol, etc.), vegetable oils (castor oil, olive oil, sesame oil, turpentine oil, etc.), animal oils (mink oil, yolk oil, squalane, squalene, etc.), water, absorption promoters and skin irritation inhibitors. The ointments may further contain a humectant, a preservative, a stabilizer, an antioxidant, a flavor, and the like.

Gels are prepared in accordance with a well known formulation or a formulation commonly employed. For example, they are prepared by melting one or more active substances in a base. The gel base is selected from well known ones or those commonly employed. For example, use may be made of one base or a mixture of two or more thereof selected from lower alcohols (ethanol, isopropyl alcohol, etc.), gelling agents (carboxymethylcellulose, hydroxyethylcellulose, hydroxypropylcellulose, ethylcellulose, etc.), neutralizing agents (triethanolamine, diisopropanolamine, etc.), surfactants (polyethylene glycol monostearate, etc.), gums, water, absorption promoters and skin irritation inhibitors. The gels may further contain a preservative, an antioxidant, a flavor, and the like.

Creams are prepared in accordance with a well known formulation or a formulation commonly employed. For example, they are prepared by melting or emulsifying one or more active substances in a base. The cream base is selected from well known ones or those commonly employed. For example, use may be made of one base or a mixture of two or more thereof selected from higher fatty acid esters, lower alcohols, hydrocarbons, polyhydric alcohols (propylene glycol, 1,3-butylene glycol, etc.), higher alcohols (2-hexyldecanol, cetanol, etc.), emulsifiers (polyoxyethylene alkyl ethers, fatty acid esters, etc.), water, absorption promoters and skin irritation inhibitors. The creams may further contain a preservative, an antioxidant, a flavor, and the like.

Fomentations are prepared in accordance with a well known formulation or a formulation commonly employed. For example, they are prepared by melting one or more active substances in a base, kneading and then applying and spreading the kneaded matter on a substrate. The fomentation base is selected from well known ones or those commonly employed. For example, use may be made of one base or a mixture of two or more thereof selected from thickeners (polyacrylic acid, polyvinylpyrrolidone, gum acacia, starch, gelatin, methylcellulose, etc.), moistening agents (urea, glycerin, propylene glycol, etc.), fillers (kaolin, zinc oxide, talc, calcium, magnesium, etc.), water, dissolution aids, tackifiers and skin irritation inhibitors. The fomentations may further contain a preservative, an antioxidant, a flavor, and the like.

Patches are prepared in accordance with a well known formulation or a formulation commonly employed. For example, they are prepared by melting one or more active substances in a base and then applying and spreading on a substrate. The patch base is selected from well known ones or those commonly employed. For example, use may be made of one base or a mixture of two or more thereof selected from polymer bases, fats and oils, higher fatty acids, tackifiers and skin irritation inhibitors. The patches may further contain a preservative, an antioxidant, a flavor, and the like.

Liniments are prepared in accordance with a well known formulation or a formulation commonly employed. For example, they are prepared by dissolving, suspending or emulsifying one or two or more active substances in one or more media selected from water, alcohols (ethanol, polyethylene glycol, etc.), higher fatty acids, glycerin, soap, emulsifiers, suspending agents, and the like. The liniments may further contain a preservative, an antioxidant, a flavor, and the like.

Atomized agents, inhalations and sprays may contain, in addition to a diluent commonly employed, a stabilizer such as sodium hydrogen sulfite, a buffering agent for imparting isotonicity, for Example, an isotonic agent such as sodium chloride, sodium citrate or citric acid. Methods for producing a spray are described in detail in, for example, U.S. Pat. No. 2,868,691 and U.S. Pat. No. 3,095,355.

The injections for parenteral administration include solutions, suspensions, emulsions and solid injections to be dissolved or suspended before use. Such an injection is used by dissolving, suspending or emulsifying one or more active substances in a solvent. The solvent includes, for example, distilled water for injection, physiological saline, vegetable oils, alcohols such as propylene glycol, polyethylene glycol and ethanol, and mixtures thereof. The injection may further contain a stabilizer, a dissolution aid (glutamic acid, aspartic acid, Polysorbate 80 (registered trademark), etc.), a suspending agent, an emulsifier, a soothing agent, a buffer, a preservative, and the like. Such an injection may be produced by sterilizing at the final step or employing an aseptic process. Alternatively, it is also possible that an aseptic solid product such as a freeze-dried product is produced and sterilized or dissolved in aseptic distilled water for injection or another solvent before use.

The inhalations for parenteral administration include aerosols, powders for inhalation and liquids for inhalation. Such inhalations may be dissolved or suspended in water or another adequate medium for use.

The inhalations may be prepared in accordance with a well known method.

For example, liquid preparations for inhalation may be, if necessary, prepared by appropriately selecting a preservative (benzalkonium chloride, paraben, etc.), a colorant, a buffering agent (sodium phosphate, sodium acetate, etc.), an isotonic agent (sodium chloride, concentrated glycerin, etc.), a thickener (carboxyvinyl polymer, etc.), an absorption promoter, and the like.

Powders for inhalation may be prepared, if necessary, by appropriately selecting a lubricant (stearic acid and its salt, etc.), a binder (starch, dextrin, etc.), an excipient (lactose, cellulose, etc.), a colorant, a preservative (benzalkonium chloride, paraben, etc.), an absorption promoter, and the like.

When the liquids for inhalation are administered, a sprayer (atomizer, nebulizer) is usually used. When the powders for inhalation are used, an inhalation administration apparatus for powder agents is usually used.

Other compositions for parenteral administration include suppositories and pessaries for vaginal administration, which contain one or more active substances, and are prepared in accordance with common formulations.

BEST MODE FOR CARRYING OUT THE INVENTION

Now, the present invention is described in greater detail by reference to the following Reference Examples, Examples, Formulation Examples and Test Examples, although the present invention is not construed as being restricted thereto.

The name of the compounds used in the present specification is designated according to IUPAC regulations.

Solvents given in parentheses concerning chromatographic separation and TLC indicate each the elution solvent or the developing solvent employed and the ratio is expressed in ratio by volume.

Solvents given in parentheses concerning NMR indicate each the solvent employed in measurement.

REFERENCE EXAMPLE 1

7-bromomethylcoumarin

To a solution of 7-methylcoumarin (50 g) in acetonitrile (1.2 L), N-bromosuccinimide (56 g) and α,α'-azobisisobutylonitrile (510 mg) were added, and the mixture was stirred for 30 minutes at 78° C. of inside temperature. The reaction mixture was concentrated, and water was added. The crystal was collected by filtration to give the title compound (76 g) having the following physical data.

NMR (300 MHz, CDCl$_3$): δ 7.69 (d, 9.6 Hz, 1H), 7.46 (d, J=8.1 Hz, 1H), 7.34 (d, J=1.8 Hz, 1H), 7.30 (dd, J=8.1, 1.8 Hz, 1H), 6.43 (d, 9.6 Hz, 1H), 4.52 (s, 2H).

REFERENCE EXAMPLE 2

7-(2,5-difluorophenoxymethyl)coumarin

The compound prepared in Reference Example 1 (40 g), 2,5-difluorophenol (21.8 g) and potassium carbonate (46.4 g) were dissolved in dimethylformamide (DMF; 250 mL), and the mixture was heated for 50 minutes at 60° C. After the reaction mixture was cooled at room temperature, water was added to the mixture. Solid was collected by filtration. The solid was dried to give the title compound (43.9 g) having the following physical data.

NMR (300 MHz, DMSO-d$_6$): δ 8.05 (d, J=9.6 Hz, 1H), 7.74 (d, J=7.8 Hz, 1H), 7.46 (brs, 1H), 7.41 (brd, J=7.8 Hz, 1H), 7.32-7.18 (m, 2H), 6.78 (m, 1H), 6.49 (d, J=9.6 Hz, 1H), 5.30 (s, 2H).

REFERENCE EXAMPLE 3

3-(4-(2,5-difluorophenoxymethyl)-2-hydroxyphenyl) propenoic acid methyl ester

Under an atmosphere of argon, to a solution of sodium hydride (18.2 g, 60% oil) in tetrahydrofuran (THF; 150 mL), methanol (24.6 mL) was added at room temperature. The mixture was stirred for 30 minutes at 50° C. The mixture was cooled to room temperature, and a solution of the compound prepared in Reference Example 2 (43.9 g) in DMF (750 mL) was dropped to the mixture. The mixture was stirred for 30 minutes at 50° C. The mixture was cooled to room temperature. 1N hydrochloric acid was added to the mixture in ice-bath. The mixture was extracted with ethyl acetate. The organic layer was washed with water and a saturated aqueous solution of sodium chloride, dried over anhydrous magnesium sulfate and concentrated. An obtained solid was crystallized by a mixture of t-butyl methyl ether/hexane to give the title compound (46.5 g) having the following physical data.

NMR (300 MHz, DMSO-d$_6$): δ 10.4 (s, 1H), 7.84 (d, J=16.2 Hz, 1H), 7.64 (d, J=7.8 Hz, 1H), 7.26 (m, 1H), 7.16 (m, 1H), 6.98 (s, 1H), 6.89 (d, J=7.8 Hz, 1H), 6.77 (m, 1H), 6.61 (d, J=16.2 Hz, 1H), 5.15 (s, 2H), 3.70 (s, 3H).

REFERENCE EXAMPLE 4

3-(4-(2,5-difluorophenoxymethyl)-2-hydroxyphenyl) propanoic acid methyl ester

To a solution of the compound prepared in Reference Example 3 (46.5 g) in THF (400 mL)/methanol (100 mL), dichloro nickel six hydrous (41.3 g) and sodium borohydride (21.9 g) were slowly added. The mixture was stirred for 2.5 hours. The reaction solution was diluted with t-butyl methyl ether and filtered through celite (trade mark). The filtrate was diluted with ethyl acetate, washed with water and a saturated aqueous solution of sodium chloride, dried over magnesium sulfate and concentrated. The residue was purified by column chromatography on silica gel (ethyl acetate hexane=1:1) to give the title compound (23.6 g) having the following physical data.

NMR (300 MHz, CDCl$_3$): δ 7.20 (s, 1H), 7.10 (d, J=7.8 Hz, 1H), 7.01 (ddd, J=10.5, 9.0, 5.4 Hz, 1H), 6.96-6.91 (m, 2H), 6.71 (m, 1H), 6.58 (m, 1H), 5.03 (s, 2H), 3.70 (s, 3H), 2.92-2.88 (m, 2H), 2.74-2.70 (m, 2H).

REFERENCE EXAMPLE 5

3-(2-carboxy-4-(2,5-difluorophenoxymethyl)phenyl) propanoic acid methyl ester

Under an atmosphere of argon, to a solution of the compound prepared in Reference Example 4 (250 mg) in pyridine (1.55 mL), trifluoromethanesulfonate (144 μL) was added at 0° C. The mixture was stirred for 60 minutes at room temperature. The reaction mixture was diluted with ethyl acetate. The dilute solution was washed with water, 1N hydrochloric acid, water and a saturated aqueous solution of sodium chloride, successively, dried over magnesium sulfate and concentrated.

Under an atmosphere of argon, to a solution of the obtained compound in DMF (2.5 mL), potassium acetate (380 mg), bis(diphenylphosphino)ferrocene (41 mg) and palladium acetate (II) (8.7 mg) were added successively. The mixture was stirred overnight at 90° C. under an atmosphere of carbon monoxide gas. The reaction mixture was diluted with t-butyl methyl ether, and filtered through celite (trade mark). The filtrate was washed with a saturated ammonium chloride solution, water and a saturated aqueous solution of sodium chloride, successively, dried over magnesium sulfate and concentrated. The residue was purified by column chromatography on silica gel (ethyl acetate:hexane=1:1) to give the title compound (193 mg) having the following physical data.

NMR (300 MHz, CDCl$_3$): δ 8.11 (d, J=1.8 Hz, 1H), 7.59 (dd, J=8.1, 1.8 Hz, 1H), 7.38 (d, J=8.1 Hz, 1H), 7.04 (m, 1H), 6.74 (m, 1H), 6.62 (m, 1H), 5.11 (s, 2H), 3.67 (s, 3H), 3.38-3.33 (m, 2H), 2.74-2.69 (m, 2H).

REFERENCE EXAMPLE 6

4-hydroxy-4-(3,5-dimethylphenyl)tetrahydro-2H-pyran

Under an atmosphere of argon, to a solution of 5-bromo-m-xylene (5.55 g) in THF (60 mL), n-butyl lithium (17.8 mL) was added at −78° C. The mixture was stirred for 1 hour. Tetrahydropyran-4-on (2.0 g) was added to the reaction mixture, and the mixture was stirred for 3 hours. Water was added to the reaction mixture, and the solution was diluted with ethyl acetate. The organic layer was washed with water and a saturated aqueous solution of sodium chloride, dried over magnesium sulfate and concentrated. The residue was purified by column chromatography on silica gel (ethyl acetate: hexane=1:3) to give the title compound (2.6 g) having the following physical data.

TLC: Rf 0.51 (ethyl acetate:hexane=1:1); NMR (300 MHz, CDCl$_3$): δ 7.10 (s, 2H), 6.93 (s, 1H), 3.99-3.82 (m, 5H), 2.34 (s, 6H), 2.23-2.11 (m, 2H), 1.72-1.63 (m, 2H).

REFERENCE EXAMPLE 7

N-(4-(3,5-dimethylphenyl)tetrahydro-2H-pyran-4-yl) chloroacetamide

To a solution of the compound prepared in Reference Example 6 (1.51 g) in chloroacetonitrile (5 mL) and acetic acid (10 mL), sulfuric acid (3 drops) was slowly dropped with the ice-bath. The mixture was stirred overnight at room temperature. The reaction mixture was poured into ice water, and basified by adding 5N aqueous solution of sodium hydroxide. The mixture was extracted with t-butyl methyl ether. The organic layer was washed with water and a saturated aqueous solution of sodium chloride, dried over magnesium sulfate and concentrated. The residue was purified by column chromatography on silica gel (ethyl acetate:hexane=1:3) to give the title compound (288 mg) having the following physical data.

TLC: Rf 0.54 (ethyl acetate:hexane=1:1); NMR (300 MHz, CDCl$_3$): δ 6.98 (s, 2H), 6.90 (s, 1H), 6.76 (bs, 1H), 4.02 (s, 2H), 3.89 (dt, J=12.0, 3.3 Hz, 2H), 3.72 (dt, J=12.0, 2.1 Hz, 2H), 2.42-2.34 (m, 2H), 2.32 (s, 6H), 2.29-2.13 (m, 2H).

REFERENCE EXAMPLE 8

4-amino-4-(3,5-dimethylphenyl)tetrahydro-2H-pyran

To the compound prepared in Reference Example 7 (250 mg) in ethanol (2 mL) and acetic acid (0.4 mL), thiourea (81.2 mg) was added. The mixture was stirred overnight at 70° C. The reaction mixture was diluted with t-butyl methyl ether, basified by adding 2N aqueous solution of sodium hydroxide, and separated organic layer. The organic layer was washed with water and a saturated aqueous solution of sodium chloride, dried over magnesium sulfate and concentrated to give the title compound (160 mg) having the following physical data.

TLC: Rf 0.54 (methanol:chloroform=1:5); NMR (300 MHz, CDCl$_3$): δ 7.07 (s, 2H), 6.90 (s, 1H), 3.92 (dt, J=11.4, 2.4 Hz, 2H), 3.79 (dt, J=11.4, 4.2 Hz, 2H), 2.34 (s, 6H), 2.24-2.13 (m, 2H), 1.68-1.60 (m, 2H).

REFERENCE EXAMPLE 9

(2R)-3-aza-4-(3,5-dimethylphenyl)-2-phenyl-3-buten-1-ol 3,5-Dimethylbenzaldehyde (30.0 g) and (R)-phenylglycinol (30.7 g) in toluene (200 mL) was refluxed with distilled off an azeotropic mixture with water for 3 hours. The reaction mixture was concentrated to give the title compound (59.7 g) having the following physical data.

TLC: Rf 0.69 (hexane:ethyl acetate=4:1).

REFERENCE EXAMPLE 10

(2R,4R)-3-aza-6-methyl-4-(3,5-dimethylphenyl)-2-phenyl-6-hepten-1-ol hydrochloride Under an atmosphere of argon, to a solution of magnesium (40.8 g) in anhydrous THF (800 mL), a solution of 3-chloro-2-methyl-1-propene (60.8 g) anhydrous THF (450 mL) was dropped in ice-bath with sodium chloride. The mixture was stirred for 1.5 hours in ice-bath, and for 1 hour at room temperature to prepare Grignard agent.

Under an atmosphere of argon, to a solution of the compound prepared in Reference Example 9 in anhydrous toluene (300 mL), the Grignard agent (1120 mL) was dropped over 3 hours and the mixture was stirred for 30 minutes in ice-bath with sodium chloride. A saturated ammonium chloride solution and water was added to the reaction mixture, and the organic layer was separated. The aqueous layer was extracted with ethyl acetate, and combined with the above organic layer. The combined organic layer was washed with a saturated aqueous solution of sodium chloride, dried over anhydrous magnesium sulfate and concentrated. To a solution of the residue in ethyl acetate (500 mL), 4N hydrochloric acid/dioxane (100 mL) was added under the ice-bath. The solution was concentrated and re-crystallized with isopropanol-hexane to give the title compound (60.9 g) having the following physical data.

TLC: Rf 0.80 (hexane:ethyl acetate=1:2); NMR (300 MHz, CDCl$_3$): δ 9.52 (brs, 2H), 7.39-7.20 (m, 5H), 6.94 (s, 2H), 6.81 (s, 1H), 5.44 (brs, 1H), 4.70 (s, 1H), 4.63 (s, 1H), 4.40-4.20 (m, 2H), 4.14 (m, 1H), 3.83 (m, 1H), 3.11 (dd, J=14, 4.4 Hz, 1H), 2.94 (dd, J=14, 11 Hz, 1H), 2.17 (s, 6H), 1.49 (s, 3H).

REFERENCE EXAMPLE 11

(1R)-3-methyl-1-(3,5-dimethylphenyl)butylamine hydrochloride

Under an atmosphere of hydrogen gas, a solution of the compound prepared in Reference Example 10 (33.0 g) and platinum oxide (IV) (4.60 g) in ethanol (330 mL) was stirred for 40 hours at 60° C. The reaction mixture was filtered through celite (trade mark), and the filtrate was concentrated. The residue was re-crystallized with ethanol/ethyl acetate to give the title compound (7.30 g) having the following physical data.

TLC: Rf 0.30 (chloroform:methanol=9:1); NMR (300 MHz, DMSO-d$_6$): δ 8.41 (brs, 3H), 7.11 (s, 2H), 7.01 (s, 1H), 4.10 (m, 1H), 2.27 (s, 6H), 1.82-1.66 (m, 2H), 1.31 (m, 1H), 0.86 (d, J=6.6 Hz, 3H), 0.82 (d, J=6.6 Hz, 3H).

EXAMPLE 1

3-(4-(2,5-difluorophenoxymethyl)-2-((((1R)-1-(naphthalen-2-yl)ethyl)amino)carbonyl)phenyl)propanoic acid methyl ester Under an atmosphere of argon, a solution of the compound prepared in Reference Example 5 (80 mg), (1R)-1-(naphthalene-2-yl)ethylamine (47 mg), 1-ethyl-3-[3-(dimethylamino)propyl]carbodiimide (66 mg) and 1-hydroxybenzotriazole (46 mg) in DMF (1 mL) was stirred overnight at room temperature. The reaction mixture was diluted with ethyl acetate. The diluted solution was washed with 1N hydrochloric acid, an aqueous solution of sodium bicarbonate, washed with water and a saturated aqueous solution of sodium chloride, successively, dried over magnesium sulfate and concentrated to give the title compound having the following physical data.

TLC: Rf 0.35 (hexane:ethyl acetate=1:1); NMR (300 MHz, CDCl$_3$): δ 7.87-7.58 (m, 4H), 7.55-7.39 (m, 5H), 7.27 (m, 1H), 7.02 (m, 1H), 6.80-6.68 (m, 2H), 6.64-6.55 (m, 1H), 5.50 (m, 1H), 5.05 (s, 2H), 3.59 (s, 3H), 3.06 (t, J=7.2 Hz, 2H), 2.70 (m, 2H), 1.70 (d, J=6.6 Hz, 3H).

EXAMPLE 2

3-(4-(2,5-difluorophenoxymethyl)-2-((((1R)-1-(naphthalen-2-yl)ethyl)amino)carbonyl)phenyl)propanoic acid To a solution of the compound prepared in Example 1 in methanol (1 mL)/THF (1 mL), 1N aqueous solution of sodium hydroxide (1 mL) was added, and the mixture was stirred overnight at room temperature. The reaction mixture was acidified by adding 1N hydrochloric acid, and extracted with ethyl acetate. The organic layer was washed with water and a saturated aqueous solution of sodium chloride, dried over magnesium sulfate and concentrated. The residue was re-crystallized with ethyl acetate/hexane to give the title compound (83 mg)) having the following physical data.

TLC: Rf 0.47 (chloroform:methanol=10:1); NMR (300 MHz, CDCl$_3$): δ 1.70 (d, J=6.96 Hz, 3H), 2.76 (t, J=7.51 Hz, 2H), 3.07 (t, J=7.51 Hz, 2H), 5.05 (s, 2H), 5.49 (m, 1H), 6.59 (m, 2H), 6.72 (m, 1H), 7.02 (m, 1H), 7.30 (d, J=7.87 Hz, 1H), 7.49 (m, 5H), 7.83 (m, 4H).

EXAMPLE 2(1) to 2(59)

The following compounds were obtained by the same procedure as a series of reactions of Reference Example 1→Reference Example 2→Reference Example 3→Reference Example 4→Reference Example 5→Example 1→Example 2 using corresponding compounds.

EXAMPLE 2(1)

3-(4-(2,5-dichlorophenoxymethyl)-2-(((4-(3-methylphenyl)tetrahydro-2H-pyran-4-yl)amino)carbonyl) phenyl)propanoic acid TLC: Rf 0.57 (chloroform:methanol=10:1); NMR (300 MHz, DMSO-d$_6$): δ 1.93 (m, 2H), 2.30 (s, 3H), 2.41 (m, 2H), 2.48 (m, 2H), 2.86 (t, J=7.83 Hz, 2H), 3.76 (m, 4H), 5.27 (s, 2H) 7.05 (m, 2H), 7.22 (m, 3H), 7.34 (d, J=7.69 Hz, 11), 7.42 (m, 2H), 7.50 (m, 2H), 8.64 (s, 1H).

EXAMPLE 2(2)

3-(4-(2-chloro-5-methylphenoxymethyl)-2-(((4-(3-methylphenyl)tetrahydro-2H-pyran-4-yl)amino)carbonyl)phenyl)propanoic acid TLC: Rf 0.60 (chloroform:methanol=10:1); NMR (300 MHz, DMSO-d$_6$): δ 1.93 (m, 2H), 2.30 (s, 3H), 2.30 (s, 3H), 2.42 (m, 4H), 2.86 (t, J=7.83 Hz, 2H), 3.76 (m, 4H), 5.21 (s, 2H), 6.79 (dd, J=7.97, 1.10 Hz, 1H), 7.02 (d, J=6.87 Hz, 1H), 7.13 (d, J=1.65 Hz, 1H), 7.21 (m, 3H), 7.32 (m, 2H) 7.44 (m, 1H), 7.53 (d, J=1.65 Hz, 1H), 8.62 (s, 1H), 12.10 (s, 1H).

EXAMPLE 2(3)

3-(4-(2-chloro-5-fluorophenoxymethyl)-2-(((4-(3-methyl phenyl)tetrahydro-2H-pyran-4-yl)amino) carbonyl)phenyl)propanoic acid TLC: Rf 0.59 (chloroform:methanol=10:1); NMR (300 MHz, DMSO-d$_6$): δ 1.92 (m, 2H), 2.30 (s, 3H), 2.44 (m, 4H), 2.86 (t, J=7.83 Hz, 2H), 3.76 (m, 4H), 5.25 (s, 2H), 6.84 (m, 1H), 7.02 (d, J=6.87 Hz, 1H), 7.23 (m, 4H), 7.34 (m, 1H), 7.47 (m, 3H), 8.64 (s, 1H).

EXAMPLE 2(4)

3-(4-(2,5-difluorophenoxymethyl)-2-(((4-phenyltetrahydro-2H-pyran-4-yl)amino)carbonyl)phenyl)propanoic acid TLC: Rf 0.23 (hexane:ethyl acetate:acetic acid=50:50:1); NMR (300 MHz, CDCl$_3$): δ 2.26 (m, 2H), 2.52 (m, 2H), 2.69 (t, J=7.28 Hz, 2H), 3.00 (t, J=7.28 Hz, 2H), 3.82 (m, 2H), 3.93 (m, 2H), 5.08 (s, 2H), 6.63 (m, 2H), 6.75 (m, 1H), 7.05 (m, 1H) 7.27 (m, 2H), 7.39 (m, 3H), 7.50 (m, 3H).

EXAMPLE 2(5)

3-(4-(2,5-dichlorophenoxymethyl)-2-(((4-phenyltetrahydro-2H-pyran-4-yl)amino)carbonyl)phenyl)propanoic acid TLC: Rf 0.35 (hexane:ethyl acetate:acetic acid=50:50:1); NMR (300 MHz, CDCl$_3$): δ 2.26 (m, 2H), 2.51 (m, 2H), 2.69 (t, J=7.28 Hz, 2H), 3.00 (t, J=7.28 Hz, 2H), 3.83 (m, 2H), 3.93 (m, 2H), 5.11 (s, 2H), 6.57 (s, 1H), 6.94 (dd, J=8.52, 2.20 Hz, 1H) 6.99 (d, J=2.20 Hz, 1H), 7.28 (m, 3H), 7.41 (m, 3H), 7.50 (m, 2H), 7.60 (d, J=1.65 Hz, 1H).

EXAMPLE 2(6)

3-(4-(2-chloro-5-fluorophenoxymethyl)-2-(((4-phenyltetrahydro-2H-pyran-4-yl)amino)carbonyl)phenyl)propanoic acid TLC: Rf 0.36 (hexane:ethyl acetate:acetic acid=50:50:1); NMR (300 MHz, CDCl$_3$): δ 2.26 (m, 2H), 2.51 (m, 2H), 2.70 (t, J=7.28 Hz, 2H), 3.01 (t, J=7.28 Hz, 2H), 3.84 (m, 2H), 3.94 (m, 2H), 5.11 (s, 2H), 6.55 (s, 1H), 6.70 (m, 2H), 7.34 (m, 6H) 7.51 (m, 2H), 7.61 (d, J=1.65 Hz, 1H).

EXAMPLE 2(7)

3-(4-(2,5-difluorophenoxymethyl)-2-((((1R)-3-methyl-1-(3-methylphenyl)butyl)amino)carbonyl)phenyl)propanoic acid TLC: Rf 0.52 (hexane:ethyl acetate=1:1); NMR (300 MHz, CDCl$_3$): δ 0.99 (d, J=6.41 Hz, 6H), 1.71 (m, 3H), 2.35 (s, 3H), 2.71 (m, 2H), 3.02 (m, 2H), 5.06 (s, 2H), 5.20 (m, 1H), 6.40 (d, J=8.79 Hz, 1H), 6.62 (m, 1H), 6.73 (m, 1H), 7.05 (m, 2H), 7.14 (m, 2H), 7.23 (d, J=7.69 Hz, 1H), 7.29 (d, J=8.42 Hz, 1H), 7.41 (m, 2H).

EXAMPLE 2(8)

3-(4-(2-chloro-5-methylphenoxymethyl)-2-((((1R)-3-methyl-1-(3-methylphenyl)butyl)amino)carbonyl)phenyl)propanoic acid TLC: Rf 0.31 (hexane:ethyl acetate=1:1); NMR (300 MHz, CDCl$_3$): δ 0.98 (d, J=6.41 Hz, 3H), 0.99 (d, J=6.41 Hz, 3H), 1.75 (m, 3H) 2.31 (s, 3H), 2.35 (s, 3H), 2.72 (m, 2H), 3.04 (m, 2H), 5.09 (s, 2H), 5.20 (m, 1H), 6.37 (d, J=8.79 Hz, 1H), 6.75 (m, 1H), 6.79 (m, 1H), 7.08 (m, 1H), 7.15 (m, 2H), 7.26 (m, 3H), 7.42 (m, 1H), 7.53 (d, J=1.65 Hz, 1H).

EXAMPLE 2(9)

3-(4-(3-cyanophenoxymethyl)-2-((((1R)-3-methyl-1-(3-methyl phenyl)butyl)amino)carbonyl)phenyl)propanoic acid TLC: Rf 0.32 (hexane:ethyl acetate=1:1); NMR (300 MHz, CDCl$_3$): δ 0.99 (d, J=6.59 Hz, 6H), 1.72 (m, 3H), 2.35 (s, 3H), 2.73 (m, 2H), 3.03 (m, 2H), 5.03 (s, 2H), 5.21 (m, 1H), 6.37 (d, J=8.60 Hz, 1H), 7.09 (brd, J=7.87 Hz, 1H) 7.17 (m, 4H), 7.27 (m, 3H), 7.38 (m, 3H).

EXAMPLE 2(10)

3-(4-(2,5-dimethylphenoxymethyl)-2-((((1R)-3-methyl-1-(3-methylphenyl)butyl)amino)carbonyl)phenyl)propanoic acid TLC: Rf 0.39 (hexane:ethyl acetate=1:1); NMR (300 MHz, CDCl$_3$): δ 0.98 (d, J=6.41 Hz, 3H), 0.99 (d, J=6.41 Hz, 3H), 1.72 (m, 3H) 2.22 (s, 3H), 2.32 (s, 3H), 2.35 (s, 3H), 2.73 (m, 2H), 3.04 (m, 2H), 5.02 (s, 2H), 5.21 (m, 1H) 6.28 (d, J=8.79 Hz, 1H), 6.71 (m, 2H), 7.06 (m, 2H) 7.14 (m, 2H), 7.23 (d, J=7.69 Hz, 1H), 7.28 (m, 1H), 7.42 (m, 2H).

EXAMPLE 2(11)

3-(4-(2,5-difluorophenoxymethyl)-2-(((4-(naphthalen-2-yl)tetrahydro-2H-pyran-4-yl)amino)carbonyl)phenyl)propanoic acid TLC: Rf 0.60 (chloroform:methanol=9:1); NMR (300 MHz, CDCl$_3$): δ 2.37 (m, 2H), 2.64 (m, 4H), 3.00 (t, J=7.14 Hz, 2H), 3.87 (m, 2H) 3.97 (m, 2H), 5.07 (s, 2H), 6.62 (m, 1H), 6.75 (m, 2H), 7.05 (m, 1H), 7.28 (d, J=8.06 Hz, 1H) 7.44 (m, 3H), 7.53 (d, J=1.65 Hz, 1H), 7.63 (dd, J=8.70, 1.92 Hz, 1H), 7.83 (m, 3H), 7.93 (d, J=1.83 Hz, 1H).

EXAMPLE 2(12)

3-(4-(2,5-dimethylphenoxymethyl)-2-(((4-(3-methylphenyl)tetrahydro-2H-pyran-4-yl)amino)carbonyl)phenyl)propanoic acid TLC: Rf 0.52 (chloroform:methanol=9:1); NMR (300 MHz, CDCl$_3$): δ 2.24 (m, 5H), 2.32 (s, 3H), 2.36 (s, 3H), 2.48 (m, 2H), 2.70 (t, J=7.32 Hz, 2H), 3.02 (t, J=7.32 Hz, 2H), 3.87 (m, 4H), 5.05 (s, 2H), 6.47 (s, 1H), 6.72 (m, 2H), 7.07 (m, 2H), 7.27 (m, 4H), 7.43 (dd, J=7.87, 1.65 Hz, 1H), 7.54 (s, 1H).

EXAMPLE 2(13)

3-(4-(3-cyanophenoxymethyl)-2-(((4-(naphthalen-2-yl)tetrahydro-2H-pyran-4-yl)amino)carbonyl)phenyl)propanoic acid TLC: Rf 0.13 (hexane:ethyl acetate=1:1, 1% acetic acid); NMR (300 MHz, CDCl$_3$): δ 2.37 (m, 2H), 2.63 (m, 2H), 2.71 (t, J=7.14 Hz, 2H), 3.00 (t, J=7.14 Hz, 2H), 3.92 (m, 4H), 5.04 (s, 2H), 6.83 (s, 1H), 7.19 (m, 2H), 7.29 (m, 2H), 7.43 (m, 5H) 7.63 (dd, J=8.70, 1.74 Hz, 1H), 7.83 (m, 3H), 7.94 (s, 1H).

EXAMPLE 2(14)

3-(4-(2,5-dimethylphenoxymethyl)-2-(((4-(naphthalen-2-yl)tetrahydro-2H-pyran-4-yl)amino)carbonyl)phenyl)propanoic acid TLC: Rf 0.33 (hexane:ethyl acetate=1:1, 1% acetic acid); NMR (300 MHz, CDCl$_3$): δ 2.26 (s, 3H), 2.32 (s, 3H), 2.38 (m, 2H), 2.59 (m, 2H), 2.69 (t, J=7.32 Hz, 2H), 3.01 (t, J=7.32 Hz, 2H), 3.86 (m, 2H) 3.98 (m, 2H), 5.05 (s, 2H), 6.59 (s, 1H) 6.73 (m, 2H), 7.06 (d, J=7.87 Hz, 1H), 7.28 (d, J=8.06 Hz, 1H), 7.45 (m, 3H), 7.56 (d, J=1.46 Hz, 1H), 7.62 (dd, J=8.60, 1.83 Hz, 1H), 7.83 (m, 3H), 7.93 (d, J=1.83 Hz, 1H).

EXAMPLE 2(15)

3-(4-(5-fluoroindol-1-ylmethyl)-2-((((1R)-1-(3,5-dimethylphenyl)-3-methylbutyl)amino)carbonyl)phenyl)propanoic acid TLC: Rf 0.42 (hexane:ethyl acetate=1:1, 1% acetic acid); NMR (300 MHz, CDCl$_3$): δ 0.93 (d, J=6.41 Hz, 6H), 1.60 (m, 3H), 2.28 (s, 6H), 2.65 (m, 2H), 2.95 (m, 2H), 5.09 (m, 1H), 5.25 (s, 2H), 6.15 (d, J=8.60 Hz, 1H), 6.50 (dd, J=3.11, 0.73 Hz, 1H), 6.90 (m, 4H), 7.00 (m, 2H), 7.12 (m, 3H), 7.28 (dd, J=9.52, 2.56 Hz, 1H).

EXAMPLE 2(16)

3-(4-(6-fluoroindol-1-ylmethyl)-2-((((1R)-1-(3,5-dimethylphenyl)-3-methylbutyl)amino)carbonyl)phenyl)propanoic acid TLC: Rf 0.44 (hexane:ethyl acetate=1:1, 1% acetic acid); NMR (300 MHz, CDCl$_3$): δ 0.93 (d, J=6.59 Hz, 6H), 1.60 (m, 3H), 2.28 (s, 6H), 2.65 (m, 2H), 2.95 (m, 2H), 5.08 (m, 1H), 5.22 (s, 2H), 6.14 (d, J=8.42 Hz, 1H), 6.53 (d, J=3.30 Hz, 1H), 6.88 (m, 5H), 7.02 (m, 2H), 7.08 (d, J=3.11 Hz, 1H) 7.16 (d, J=8.42 Hz, 1H), 7.55 (dd, J=8.42, 5.31 Hz, 1H).

EXAMPLE 2(17)

3-(2-(((((1R)-1-(3,5-dimethylphenyl)-3-methylbutyl)amino)carbonyl)-4-(3-pyridyloxymethyl)phenyl)propanoic acid TLC: Rf 0.49 (chloroform:methanol=9:1); NMR (300 MHz, DMSO-d$_6$): δ 0.91 (m, 6H), 1.42 (m, 1H), 1.71 (m, 2H), 2.24 (s, 6H), 2.43 (m, 2H), 2.83 (m, 2H), 4.96 (m, 1H), 5.17 (s, 2H), 6.84 (s, 1H), 6.95 (s, 2H), 7.39 (m, 5H), 8.17 (d, J=4.03 Hz, 1H), 8.35 (s, 1H), 8.76 (d, J=8.42 Hz, 1H), 12.08 (s, 1H).

EXAMPLE 2(18)

3-(4-(2,4-dimethylphenoxymethyl)-2-((((1R)-1-(3,5-dimethylphenyl)-3-methylbutyl)amino)carbonyl)phenyl)propanoic acid TLC: Rf 0.61 (chloroform:methanol=9:1); NMR (300 MHz, CDCl$_3$): δ 0.98 (d, J=6.31 Hz, 3H), 0.99 (d, J=6.31 Hz, 3H), 1.70 (m, 3H), 2.23 (s, 3H), 2.26 (s, 3H), 2.31 (s, 6H), 2.72 (m, 2H), 3.03 (m, 2H), 5.01 (s, 2H), 5.15 (m, 1H), 6.24 (d, J=8.79 Hz, 1H), 6.75 (d, J=8.24 Hz, 1H), 6.94 (m, 5H), 7.27 (m, 1H), 7.41 (m, 2H).

EXAMPLE 2(19)

3-(2-(((4-(naphthalen-2-yl)tetrahydro-2H-pyran-4-yl)amino)carbonyl)-4-phenoxymethylphenyl)propanoic acid TLC: Rf 0.26 (chloroform:methanol=9:1); NMR (300 MHz, CDCl$_3$): δ 2.35 (m, 2H), 2.64 (m, 4H), 2.99 (t, J=7.14 Hz, 2H), 3.91 (m, 4H), 5.04 (s, 2H), 6.70 (s, 1H), 6.96 (m, 3H), 7.30 (m, 3H), 7.45 (m, 4H), 7.61 (dd, J=8.60, 2.01 Hz, 1H), 7.82 (m, 3H), 7.92 (d, J=1.46 Hz, 1H).

EXAMPLE 2(20)

3-(2-(((4-(naphthalen-2-yl)tetrahydro-2H-pyran-4-yl)amino)carbonyl)-4-(3-pyridyloxymethyl)phenyl)propanoic acid TLC: Rf 0.43 (hexane:ethyl acetate=1:1, 1% acetic acid); NMR (300 MHz, DMSO-d$_6$): δ 2.06 (m, 2H), 2.49 (m, 4H), 2.85 (t, J=7.78 Hz, 2H), 3.81 (d, J=7.87 Hz, 4H), 5.21 (s, 2H), 7.34 (m, 2H), 7.48 (m, 5H), 7.65 (dd, J=8.70, 1.74 Hz, 1H), 7.88 (m, 4H), 8.18 (dd, J=4.58, 1.28 Hz, 1H), 8.37 (d, J=2.75 Hz, 1H), 8.81 (brs, 1H).

EXAMPLE 2(21)

3-(4-(3-chlorophenoxymethyl)-2-(((4-(naphthalen-2-yl)tetrahydro-2H-pyran-4-yl)amino)carbonyl)phenyl)propanoic acid TLC: Rf 0.60 (hexane:ethyl acetate=1:1, 1% acetic acid); NMR (300 MHz, CDCl$_3$): δ 2.37 (m, 2H), 2.62 (d, J=12.63 Hz, 2H), 2.70 (t, J=7.14 Hz, 2H), 3.00 (t, J=7.60 Hz, 2H), 3.85 (m, 2H), 3.97 (m, 2H) 5.03 (s, 2H), 6.68 (s, 1H), 6.85 (m, 1H), 6.97 (m, 2H), 7.22 (t, J=7.96 Hz, 1H), 7.29 (d, J=7.87 Hz, 1H), 7.45 (m, 4H), 7.62 (m, 1H), 7.83 (m, 3H), 7.93 (s, 1H).

EXAMPLE 2(22)

3-(4-(2-fluoro-5-methylphenoxymethyl)-2-((((1R)-1-(3,5-dimethylphenyl)-3-methylbutyl)amino)carbonyl)phenyl)propanoic acid TLC: Rf 0.59 (hexane:ethyl acetate=1:1, 1% acetic acid); NMR (300 MHz, CDCl$_3$): δ 0.98 (d, J=6.32 Hz, 3H), 0.99 (d, J=6.32 Hz, 3H), 1.72 (m, 3H) 2.29 (s, 3H), 2.31 (s, 6H), 2.72 (m, 2H), 3.03 (m, 2H), 5.07 (s, 2H), 5.16 (m, 1H), 6.31 (d, J=8.42 Hz, 1H), 6.72 (m, 1H), 6.81 (dd, J=7.87, 1.83 Hz, 1H), 6.91 (s, 1H), 6.97 (m, 3H), 7.28 (d, J=7.69 Hz, 1H), 7.42 (m, 2H).

EXAMPLE 2(23)

3-(4-(3,4-dimethylphenoxymethyl)-2-((((1R)-1-(3,5-dimethylphenyl)-3-methylbutyl)amino)carbonyl)phenyl)propanoic acid TLC: Rf 0.59 (hexane:ethyl acetate=1:1, 1% acetic acid); NMR (300 MHz, CDCl$_3$): δ 0.97 (d, J=6.41 Hz, 3H), 0.98 (d, J=6.41 Hz, 3H), 1.69 (m, 3H) 2.20 (s, 3H), 2.24 (s, 3H), 2.31 (s, 6H), 2.71 (m, 2H), 3.03 (m, 2H), 4.98 (s, 2H), 5.16 (m, 1H) 6.28 (d, J=8.42 Hz, 1H), 6.69 (dd, J=8.15, 2.84 Hz, 1H), 6.78 (d, J=2.56 Hz, 1H), 6.90 (s, 1H), 6.95 (s, 2H), 7.04 (d, J=8.42 Hz, 1H), 7.27 (m, 1H), 7.41 (m, 2H).

EXAMPLE 2(24)

3-(4-(2-chloro-5-fluorophenoxymethyl)-2-((((1R)-1-(3,5-dimethylphenyl)-3-methylbutyl)amino)carbonyl)phenyl)propanoic acid TLC: Rf 0.59 (hexane:ethyl acetate=1:1, 1% acetic acid); NMR (300 MHz, CDCl$_3$): δ 0.98 (d, J=6.32 Hz, 3H), 0.99 (d, J=6.32 Hz, 3H), 1.73 (m, 3H) 2.31 (s, 6H), 2.72 (m, 2H), 3.04 (m, 2H), 5.08 (s, 2H), 5.16 (m, 1H), 6.30 (d, J=8.60 Hz, 1H), 6.67 (m, 2H), 6.91 (s, 1H), 6.96 (s, 2H), 7.32 (m, 2H), 7.42 (m, 1H), 7.49 (d, J=1.65 Hz, 1H).

EXAMPLE 2(25)

3-(2-((((1R)-1-(3,5-dimethylphenyl)-3-methylbutyl)amino)carbonyl)-4-(3-methylindol-1-ylmethyl)phenyl)propanoic acid TLC: Rf 0.45 (hexane:ethyl acetate=1:1, 1% acetic acid); NMR (300 MHz, CDCl$_3$): δ 0.93 (d, J=6.59 Hz, 6H), 1.58 (m, 3H), 2.28 (s, 6H), 2.33 (d, J=0.73 Hz, 3H), 2.66 (t, J=7.32 Hz, 2H), 2.95 (m, 2H), 5.07 (m, 1H), 5.22 (s, 2H), 6.10 (d, J=8.79 Hz, 1H), 6.87 (s, 4H), 7.04 (m, 2H), 7.14 (m, 4H), 7.58 (m, 1H).

EXAMPLE 2(26)

3-(4-(2,5-difluorophenoxymethyl)-2-((((1R)-1-(naphthalen-1-yl)ethyl)amino)carbonyl)phenyl)propanoic acid TLC: Rf 0.47 (chloroform:methanol=10:1); NMR (300 MHz, CDCl$_3$): δ 1.80 (d, J=6.77 Hz, 3H), 2.77 (t, J=7.32 Hz, 2H), 3.09 (t, J=7.32 Hz, 2H), 5.00 (s, 2H), 6.14 (m, 1H), 6.37 (d, J=8.06 Hz, 1H), 6.63 (m, 2H), 7.00 (m, 1H), 7.28 (d, J=7.69 Hz, 1H), 7.50 (m, 6H), 7.82 (d, J=8.24 Hz, 1H), 7.88 (d, J=7.69 Hz, 1H), 8.22 (d, J=8.24 Hz, 1H).

EXAMPLE 2(27)

3-(4-(2-fluoro-5-methylphenoxymethyl)-2-((((1R)-1-(naphthalen-1-yl))amino)carbonyl)phenyl)propanoic acid TLC: Rf 0.41 (chloroform:methanol=10:1); NMR (300 MHz, CDCl$_3$): δ 1.80 (d, J=6.77 Hz, 3H), 2.25 (s, 3H), 2.77 (t, J=7.05 Hz, 2H), 3.09 (t, J=7.05 Hz, 2H), 5.01 (s, 2H), 6.14 (m, 1H), 6.37 (d, J=8.06 Hz, 1H), 6.69 (m, 1H), 6.75 (m, 1H), 6.93 (dd, J=11.26, 8.15 Hz, 1H), 7.27 (m, 1H), 7.51 (m, 6H), 7.82 (d, J=8.42 Hz, 1H) 7.88 (d, J=6.96 Hz, 1H), 8.22 (d, J=8.60 Hz, 1H).

EXAMPLE 2(28)

3-(4-(2-fluoro-5-methylphenoxymethyl)-2-((((1R)-3-methyl-1-(3-methylphenyl)butyl)amino)carbonyl)phenyl)propanoic acid TLC: Rf 0.41 (chloroform:methanol=10:1); NMR (300 MHz, CDCl$_3$): δ 0.99 (d, J=6.41 Hz, 6H), 1.74 (m, 3H), 2.29 (s, 3H), 2.35 (s, 3H), 2.72 (t, J=7.69 Hz, 2H), 3.03 (m, 2H), 5.07 (s, 2H), 5.20 (m, 1H), 6.35 (d, J=8.60 Hz, 1H) 6.74 (m, 1H), 6.81 (dd, J=7.96, 2.11 Hz, 1H), 6.97 (dd, J=11.26, 8.15 Hz, 1H), 7.23 (m, 5H), 7.42 (m, 2H).

EXAMPLE 2(29)

3-(4-(2-fluoro-5-methylphenoxymethyl)-2-(((4-(naphthalen-2-yl)tetrahydro-2H-pyran-4-yl)amino)carbonyl)phenyl)propanoic acid TLC: Rf 0.41 (chloroform:methanol=10:1); NMR (300 MHz, CDCl$_3$): δ 2.30 (s, 3H), 2.38 (m, 2H), 2.61 (m, 2H), 2.68 (t, J=7.20 Hz, 2H) 2.99 (t, J=7.20 Hz, 2H), 3.91 (m, 4H), 5.09 (s, 2H), 6.68 (m, 2H), 6.83 (d, J=8.06 Hz, 1H), 6.98 (dd, J=11.26, 8.15 Hz, 1H), 7.27 (d, J=7.20 Hz, 1H) 7.51 (m, 5H), 7.87 (m, 4H).

EXAMPLE 2(30)

3-(2-(((4-(3,5-dimethylphenyl)tetrahydro-2H-pyran-4-yl)amino)carbonyl)-4-(2-fluoro-5-methylphenoxymethyl)phenyl)propanoic acid TLC: Rf 0.41 (chloroform:methanol=10:1); NMR (300 MHz, CDCl$_3$): δ 2.23 (m, 2H), 2.30 (s, 3H), 2.32 (s, 6H), 2.45 (m, 2H), 2.70 (t, J=7.23 Hz, 2H), 3.03 (t, J=7.23 Hz, 2H), 3.86 (m, 4H) 5.10 (s, 2H), 6.46 (s, 1H), 6.73 (m, 1H) 6.83 (m, 1H), 6.91 (s, 1H), 6.98 (dd, J=11.17, 8.24 Hz, 1H), 7.08 (s, 2H), 7.29 (d, J=8.06 Hz, 1H), 7.43 (dd, J=7.87, 1.83 Hz, 1H), 7.56 (s, 1H).

EXAMPLE 2(31)

3-(4-(2-fluoro-5-methylphenoxymethyl)-2-(((4-(3-methylphenyl)tetrahydro-2H-pyran-4-yl)amino)carbonyl)phenyl)propanoic acid TLC: Rf 0.41 (chloroform:methanol=10:1); NMR (300 MHz, CDCl$_3$): δ 2.23 (m, 2H), 2.30 (s, 3H), 2.36 (s, 3H), 2.49 (m, 2H), 2.69 (t, J=7.32 Hz, 2H), 3.01 (t, J=7.32 Hz, 2H), 3.89 (m, 4H) 5.09 (s, 2H), 6.51 (s, 1H), 6.73 (m, 1H) 6.84 (dd, J=7.96, 1.92 Hz, 1H), 6.98 (dd, J=11.17, 8.24 Hz, 1H), 7.08 (m, 1H), 7.27 (m, 4H), 7.43 (m, 1H), 7.55 (d, J=1.65 Hz, 1H).

EXAMPLE 2(32)

3-(2-(((4-(benzofuran-2-yl)tetrahydro-2H-pyran-4-yl)amino)carbonyl)-4-(2,5-difluorophenoxymethyl)phenyl)propanoic acid TLC: Rf 0.52 (chloroform:methanol=9:1); NMR (300 MHz, CDCl$_3$): δ 2.48 (m, 4H), 2.72 (t, J=7.14 Hz, 2H), 3.03 (t, J=7.14 Hz, 2H), 3.86 (m, 4H), 5.07 (s, 2H), 6.62 (m, 1H), 6.74 (m, 3H), 7.04 (m, 1H), 7.24 (m, 3H), 7.42 (m, 2H), 7.54 (m, 2H).

EXAMPLE 2(33)

3-(4-(2,5-difluorophenoxymethyl)-2-(((4-(2-phenylethyl)tetrahydro-2H-pyran-4-yl)amino)carbonyl)phenyl)propanoic acid TLC: Rf 0.49 (chloroform:methanol=10:1); NMR (300 MHz, DMSO-d$_6$): δ 1.53 (m, 2H), 2.05 (m, 2H), 2.26 (d, J=13.73 Hz, 2H), 2.57 (m, 4H), 2.97 (m, 2H), 3.63 (m, 4H), 5.20 (s, 2H), 6.78 (m, 1H), 7.22 (m, 7H), 7.35 (d, J=8.42 Hz, 1H), 7.43 (m, 1H), 8.06 (s, 1H).

EXAMPLE 2(34)

3-(2-((((1R)-1-(3,5-dimethylphenyl)-3-methylbutyl)amino)carbonyl)-4-(4-fluoro-2-methylphenoxymethyl)phenyl)propanoic acid TLC: Rf 0.57 (chloroform:methanol=9:1); NMR (300 MHz, CDCl$_3$): δ 0.98 (d, J=6.32 Hz, 3H), 0.99 (d, J=6.32 Hz, 3H), 1.69 (m, 3H) 2.24 (s, 3H), 2.31 (s, 6H), 2.75 (t, J=7.51 Hz, 2H), 3.04 (m, 2H), 4.99 (s, 2H), 5.17 (m, 1H), 6.27 (d, J=7.69 Hz, 1H), 6.82 (m, 4H), 6.95 (s, 2H), 7.29 (d, J=8.42 Hz, 1H), 7.41 (s, 2H).

EXAMPLE 2(35)

3-(2-((((1R)-1-(3,5-dimethylphenyl)-3-methylbutyl)amino)carbonyl)-4-((2-methylpyridin-3-yl)oxymethyl)phenyl)propanoic acid TLC: Rf 0.57 (chloroform:methanol=9:1); NMR (300 MHz, DMSO-$d_6$): δ 0.89 (d, J=6.22 Hz, 3H), 0.93 (d, J=6.22 Hz, 3H), 1.40 (m, 1H), 1.72 (m, 2H), 2.25 (m, 6H), 2.39 (s, 3H), 2.44 (d, J=6.96 Hz, 2H), 2.84 (t, J=7.87 Hz, 2H), 4.96 (m, 1H) 5.15 (s, 2H), 6.84 (s, 1H), 6.95 (s, 2H), 7.17 (dd, J=8.06, 4.76 Hz, 1H), 7.38 (m, 4H), 8.01 (m, 1H) 8.79 (d, J=8.79 Hz, 1H).

EXAMPLE 2(36)

3-(2-((((1R)-1-(3,5-dimethylphenyl)-3-methylbutyl)amino)carbonyl)-4-((2-methylpyridin-5-yl)oxymethyl)phenyl)propanoic acid TLC: Rf 0.57 (chloroform:methanol=9:1); NMR (300 MHz, DMSO-$d_6$): δ 0.89 (d, J=6.41 Hz, 3H), 0.93 (d, J=6.41 Hz, 3H), 1.38 (m, 1H), 1.69 (m, 2H), 2.24 (s, 6H), 2.39 (s, 3H), 2.43 (m, 2H), 2.84 (t, J=7.87 Hz, 2H), 4.97 (m, 1H), 5.15 (s, 2H) 6.84 (s, 1H), 6.95 (s, 2H), 7.17 (dd, J=8.42, 4.76 Hz, 1H), 7.31 (d, J=8.06 Hz, 1H), 7.40 (m, 3H) 8.00 (d, J=4.76 Hz, 1H), 8.80 (d, J=8.06 Hz, 1H).

EXAMPLE 2(37)

3-(2-((((1R)-1-(3,5-dimethylphenyl)-3-methylbutyl)amino)carbonyl)-4-(5-fluoro-2-methylphenoxymethyl)phenyl)propanoic acid (hereinafter, the compound (I))

TLC: Rf 0.57 (chloroform:methanol=9:1); NMR (300 MHz, DMSO-$d_6$): δ 0.90 (d, J=6.68 Hz, 3H), 0.92 (d, J=6.68 Hz, 3H), 1.39 (m, 1H), 1.70 (m, 2H), 2.13 (s, 3H), 2.24 (s, 6H), 2.42 (t, J=7.32 Hz, 2H), 2.81 (t, J=7.05 Hz, 2H), 4.97 (m, 1H), 5.09 (s, 2H), 6.66 (m, 1H), 6.83 (s, 1H), 6.92 (dd, J=11.44, 2.47 Hz, 1H), 6.97 (s, 2H), 7.15 (t, J=7.60 Hz, 1H), 7.31 (m, 2H), 7.38 (m, 1H).

EXAMPLE 2(38)

3-(4-(3-fluorophenoxymethyl)-2-(((4-(naphthalen-2-yl)tetrahydro-2H-pyran-4-yl)amino)carbonyl)phenyl)propanoic acid TLC: Rf 0.54 (chloroform:methanol=9:1); NMR (300 MHz, DMSO-$d_6$): δ 2.06 (m, 2H), 2.53 (m, 4H), 2.85 (t, J=7.69 Hz, 2H), 3.81 (d, J=8.79 Hz, 4H), 5.15 (s, 2H), 6.78 (m, 1H), 6.90 (m, 2H), 7.33 (m, 2H), 7.46 (m, 4H), 7.65 (dd, J=8.79, 1.65 Hz, H), 7.88 (m, 4H), 8.79 (s, 1H).

EXAMPLE 2(39)

3-(4-(3-methylphenoxymethyl)-2-(((4-(naphthalen-2-yl)tetrahydro-2H-pyran-4-yl)amino)carbonyl)phenyl)propanoic acid TLC: Rf 0.59 (chloroform:methanol=9:1); NMR (300 MHz, DMSO-$d_6$): δ 2.06 (m, 2H), 2.28 (s, 3H), 2.54 (m, 4H), 2.85 (t, J=7.32 Hz, 2H), 3.81 (d, J=8.97 Hz, 4H), 5.10 (s, 2H), 6.80 (m, 3H), 7.17 (t, J=7.78 Hz, 1H), 7.31 (d, J=7.51 Hz, 1H), 7.46 (m, 4H), 7.65 (dd, J=8.79, 1.83 Hz, 1H), 7.88 (m, 4H), 8.78 (s, 1H).

EXAMPLE 2(40)

3-(4-(2,5-dimethylphenoxymethyl)-2-(((4-(2-phenylethyl)tetrahydro-2H-pyran-4-yl)amino)carbonyl)phenyl)propanoic acid TLC: Rf 0.53 (chloroform:methanol=9:1); NMR (300 MHz, DMSO-$d_6$): δ1.51 (m, 2H), 2.05 (m, 2H), 2.12 (s, 3H), 2.28 (m, 5H), 2.58 (m, 4H), 2.98 (t, J=8.24 Hz, 2H), 3.62 (m, 4H), 5.10 (s, 2H), 6.64 (m, 1H), 6.88 (s, 1H), 7.00 (d, J=7.69 Hz, 1H), 7.17 (m, 3H), 7.26 (m, 2H), 7.34 (d, J=8.06 Hz, 1H), 7.43 (m, 1H), 7.48 (s, 1H), 8.09 (s, 1H).

EXAMPLE 2(41)

3-(2-(((4-(benzofuran-2-yl)tetrahydro-2H-pyran-4-yl)amino)carbonyl)-4-(2,5-dimethylphenoxymethyl)phenyl)propanoic acid TLC: Rf 0.53 (chloroform:methanol=9:1); NMR (300 MHz, DMSO-$d_6$): δ 2.09 (m, 2H), 2.15 (s, 3H), 2.26 (s, 3H), 2.44 (m, 2H), 2.52 (m, 2H), 2.90 (t, J=7.69 Hz, 2H), 3.76 (d, J=6.59 Hz, 4H), 5.10 (s, 2H), 6.66 (d, J=7.32 Hz, 1H), 6.76 (s, 1H), 6.88 (s, 1H), 7.03 (d, J=7.32 Hz, 1H), 7.22 (m, 2H), 7.33 (d, J=7.69 Hz, 1H), 7.47 (m, 3H), 7.57 (m, 1H), 8.82 (s, 1H).

EXAMPLE 2(42)

3-(2-(((4-(benzothiophen-2-yl)tetrahydro-2H-pyran-4-yl)amino)carbonyl)-4-(2,5-difluorophenoxymethyl)phenyl)propanoic acid TLC: Rf 0.48 (chloroform:methanol=10:1); NMR (300 MHz, DMSO-$d_6$): δ 2.06 (m, 2H), 2.58 (m, 4H), 2.91 (t, J=7.96 Hz, 2H), 3.77 (m, 4H), 5.22 (s, 2H), 6.78 (m, 1H), 7.31 (m, 6H), 7.46 (m, 2H), 7.77 (d, J=6.96 Hz, 1H), 7.86 (d, J=7.51 Hz, 1H), 8.90 (s, 1H).

EXAMPLE 2(43)

3-(2-(((4-(benzothiophen-2-yl)tetrahydro-2H-pyran-4-yl)amino)carbonyl)-4-(2,5-dimethylphenoxymethyl)phenyl)propanoic acid TLC: Rf 0.48 (chloroform:methanol=10:1); NMR (300 MHz, DMSO-$d_6$): δ 2.07 (m, 2H), 2.18 (s, 3H), 2.26 (s, 3H), 2.57 (m, 4H), 2.92 (t, J=8.06 Hz, 2H), 3.77 (m, 4H), 5.12 (s, 2H), 6.67 (d, J=7.51 Hz, 1H), 6.89 (s, 1H), 7.04 (d, J=7.32 Hz, 1H), 7.32 (m, 4H), 7.45 (m, 1H), 7.53 (s, 1H), 7.77 (d, J=6.77 Hz, 1H), 7.85 (d, J=7.32 Hz, 1H), 8.91 (s, 1H).

EXAMPLE 2(44)

3-(4-(2,5-difluorophenoxymethyl)-2-(((4-(2-(2-fluorophenyl)ethyl)tetrahydro-2H-pyran-4-yl)amino)carbonyl)phenyl)propanoic acid TLC: Rf 0.35 (hexane:ethyl acetate=1:1, 1% acetic acid); NMR (300 MHz, CDCl$_3$): δ 1.83 (m, 2H), 2.26 (m, 4H), 2.70 (m, 2H), 2.87 (t, J=7.41 Hz, 2H), 3.14 (t, J=7.51 Hz, 2H), 3.70 (m, 2H), 3.85 (m, 2H), 5.10 (s, 2H), 6.07 (s, 1H), 6.62 (m, 1H), 6.76 (m, 1H), 7.02 (m, 3H), 7.17 (m, 2H), 7.34 (d, J=7.69 Hz, 1H), 7.46 (m, 1H), 7.51 (d, J=1.83 Hz, 1H).

EXAMPLE 2(45)

3-(4-(2,5-dimethylphenoxymethyl)-2-(((4-(2-(2-fluorophenyl)ethyl)tetrahydro-2H-pyran-4-yl)amino)carbonyl)phenyl)propanoic acid TLC: Rf 0.40 (hexane:ethyl acetate=1:1, 1% acetic acid); NMR (300 MHz, CDCl$_3$): δ 1.82 (m, 2H), 2.26 (m, 7H), 2.32 (s, 3H), 2.70 (m, 2H), 2.87 (t, J=7.14 Hz, 2H), 3.14 (t, J=7.14 Hz, 2H), 3.69 (m, 2H), 3.85 (m, 2H), 5.06 (s, 2H), 5.98 (s, 1H), 6.71 (d, J=6.22 Hz, 2H), 7.01 (m, 3H), 7.18 (m, 2H), 7.33 (d, J=7.87 Hz, 1H), 7.47 (m, 1H), 7.54 (m, 1H).

EXAMPLE 2(46)

3-(4-(2,5-dimethylphenoxymethyl)-2-(((4-(2-(4-fluorophenyl)ethyl)tetrahydro-2H-pyran-4-yl)amino)carbonyl)phenyl)propanoic acid TLC: Rf 0.50 (chloroform:methanol=9:1); NMR (300 MHz, CDCl$_3$): δ 1.80 (m, 2H), 2.26 (m, 7H), 2.32 (s, 3H), 2.63 (m, 2H), 2.86 (t, J=7.37 Hz, 2H), 3.13 (t, J=7.37 Hz, 2H), 3.68 (m, 2H), 3.84 (m, 2H), 5.06 (s, 2H), 5.95 (s, 1H), 6.72 (m, 2H), 6.95 (m, 2H), 7.04 (d, J=7.87 Hz, 1H), 7.15 (iii, 2H), 7.33 (d, J=7.87 Hz, 1H), 7.46 (dd, J=8.10, 1.50 Hz, 1H), 7.51 (d, J=1.28 Hz, 1H).

EXAMPLE 2(47)

3-(4-(2,5-difluorophenoxymethyl)-2-(((4-(2-(3-fluorophenyl)ethyl)tetrahydro-2H-pyran-4-yl)amino)carbonyl)phenyl)propanoic acid TLC: Rf 0.50 (chloroform:methanol=9:1); NMR (300 MHz, CDCl$_3$): δ 1.80 (m, 2H), 2.27 (m, 4H), 2.67 (m, 2H), 2.85 (t, J=7.23 Hz, 2H), 3.13 (t, J=7.23 Hz, 2H), 3.69 (m, 2H), 3.85 (m, 2H), 5.09 (s, 2H), 6.11 (s, 1H), 6.62 (m, 1H), 6.75 (m, 1H), 6.98 (m, 4H), 7.21 (m, 1H), 7.33 (d, J=8.06 Hz, 1H), 7.46 (m, 2H).

EXAMPLE 2(48)

3-(4-(2,5-dimethylphenoxymethyl)-2-(((4-(2-(3-fluorophenyl)ethyl)tetrahydro-2H-pyran-4-yl)amino)carbonyl)phenyl)propanoic acid TLC: Rf 0.50 (chloroform:methanol=9:1); NMR (300 MHz, CDCl$_3$): δ 1.80 (m, 2H), 2.27 (m, 10H), 2.66 (m, 2H), 2.86 (t, J=7.14 Hz, 2H), 3.14 (t, J=7.14 Hz, 2H), 3.68 (m, 2H), 3.86 (m, 2H), 5.06 (s, 2H), 5.98 (s, 1H), 6.71 (m, 2H), 6.94 (m, 4H), 7.21 (m, 1H), 7.33 (d, J=7.69 Hz, 1H), 7.47 (d, J=8.06 Hz, 1H), 7.51 (s, 1H).

EXAMPLE 2(49)

3-(4-(6-fluoroindol-1-ylmethyl)-2-(((4-(2-phenylethyl)tetrahydro-2H-pyran-4-yl)amino)carbonyl)phenyl)propanoic acid NMR (300 MHz, CDCl$_3$): δ 1.72 (m, 2H), 2.16 (m, 4H), 2.53 (m, 2H), 2.81 (t, J=7.14 Hz, 2H), 3.07 (t, J=7.32 Hz, 2H), 3.43 (m, 2H), 3.76 (m, 2H), 5.28 (s, 2H), 5.75 (s, 1H), 6.54 (dd, J=3.20, 0.82 Hz, 1H), 6.87 (m, 3H), 7.20 (m, 8H), 7.54 (dd, J=8.88, 5.58 Hz, 1H).

EXAMPLE 2(50)

3-(4-(6-fluoroindol-3-ylmethyl)-2-(((4-(2-phenylethyl)tetrahydro-2H-pyran-4-yl)amino)carbonyl)phenyl)propanoic acid NMR (300 MHz, CDCl$_3$): δ1.73 (m, 2H), 2.18 (m, 4H), 2.56 (m, 2H), 2.83 (t, J=7.56 Hz, 2H), 3.08 (t, J=7.56 Hz, 2H), 3.50 (m, 2H), 3.78 (m, 2H), 4.09 (s, 1H), 5.76 (s, 1H), 6.83 (m, 1H), 6.93 (d, J=2.75 Hz, 1H), 7.03 (dd, J=9.61, 2.29 Hz, 1H), 7.26 (m, 10H), 8.03 (s, 1H).

EXAMPLE 2(51)

3-(4-(3-methylindol-1-ylmethyl)-2-(((4-(2-phenylethyl)tetrahydro-2H-pyran-4-yl)amino)carbonyl)phenyl)propanoic acid NMR (300 MHz, CDCl$_3$): δ 1.69 (m, 2H), 2.07 (m, 2H), 2.18 (m, 2H), 2.31 (d, J=1.10 Hz, 3H), 2.50 (m, 2H), 2.80 (t, J=7.23 Hz, 2H), 3.06 (t, J=7.23 Hz, 2H), 3.38 (m, 2H), 3.75 (m, 2H), 5.28 (s, 2H), 5.62 (s, 1H), 6.84 (d, J=1.46 Hz, 1H), 6.90 (d, J=1.10 Hz, 1H), 7.18 (m, 10H), 7.59 (m, 1H).

EXAMPLE 2(52)

3-(4-(3-cyanophenoxymethyl)-2-(((4-(2-phenylethyl)tetrahydro-2H-pyran-4-yl)amino)carbonyl)phenyl)propanoic acid NMR (300 MHz, CDCl$_3$): δ 1.82 (m, 2H), 2.28 (m, 4H), 2.67 (m, 2H), 2.87 (t, J=7.18 Hz, 2H), 3.14 (t, J=7.18 Hz, 2H), 3.68 (m, 2H), 3.85 (m, 2H), 5.06 (s, 2H), 6.16 (s, 1H), 7.30 (m, 12H).

EXAMPLE 2(53)

3-(4-(6-fluoroindol-1-ylmethyl)-2-(((4-(naphthalen-2-yl)tetrahydro-2H-pyran-4-yl)amino)carbonyl)phenyl)propanoic acid NMR (300 MHz, CDCl$_3$): δ 2.28 (m, 2H), 2.47 (m, 2H), 2.64 (t, J=7.18 Hz, 2H), 2.94 (t, J=7.18 Hz, 2H), 3.60 (m, 2H), 3.89 (m, 2H), 5.27 (s, 2H), 6.38 (s, 1H), 6.58 (d, J=3.11 Hz, 1H), 6.90 (m, 3H), 7.10 (m, 2H), 7.19 (m, 1H), 7.47 (m, 3H), 7.59 (dd, J=8.60, 5.31 Hz, 1H), 7.81 (m, 4H).

EXAMPLE 2(54)

3-(4-(6-fluoroindol-3-ylmethyl)-2-(((4-(naphthalen-2-yl)tetrahydro-2H-pyran-4-yl)amino)carbonyl)phenyl)propanoic acid NMR (300 MHz, CDCl$_3$): δ 2.32 (m, 2H), 2.51 (m, 2H), 2.67 (t, J=7.28 Hz, 2H), 2.96 (t, J=7.28 Hz, 2H), 3.69 (m, 2H), 3.91 (m, 2H), 4.10 (s, 2H), 6.40 (s, 1H), 6.85 (m, 1H), 6.92 (d, J=1.83 Hz, 1H), 7.06 (m, 1H), 7.18 (d, J=8.42 Hz, 1H), 7.29 (m, 2H), 7.37 (dd, J=8.88, 5.03 Hz, 1H), 7.47 (m, 2H), 7.53 (dd, J=8.97, 1.83 Hz, 1H), 7.80 (m, 3H), 7.86 (m, 1H), 8.04 (s, 1H).

EXAMPLE 2(55)

3-(4-(3-methylindol-1-ylmethyl)-2-(((4-(naphthalen-2-yl)tetrahydro-2H-pyran-4-yl)amino)carbonyl)phenyl)propanoic acid NMR (300 MHz, CDCl$_3$): δ 2.25 (m, 2H), 2.37 (d, J=1.10 Hz, 3H), 2.42 (m, 2H), 2.62 (t, J=7.23 Hz, 2H), 2.93 (t, J=7.23 Hz, 2H), 3.56 (m, 2H), 3.87 (m, 2H), 5.28 (s, 2H), 6.27 (s, 1H), 6.90 (dd, J=6.68, 1.19 Hz, 2H), 7.17 (m, 5H), 7.44 (m, 3H), 7.63 (m, 1H), 7.80 (m, 4H).

EXAMPLE 2(56)

3-(4-(6-fluoroindol-1-ylmethyl)-2-(((4-(2-(3-fluorophenyl)ethyl)tetrahydro-2H-pyran-4-yl)amino)carbonyl)phenyl)propanoic acid NMR (300 MHz, CDCl$_3$): δ 1.70 (m, 2H), 2.16 (m, 4H), 2.51 (m, 2H), 2.80 (t, J=7.32 Hz, 2H), 3.07 (t, J=7.32 Hz, 2H), 3.42 (m, 2H), 3.76 (m, 2H), 5.29 (s, 2H), 5.76 (s, 1H), 6.54 (d, J=3.30 Hz, 1H), 6.89 (m, 6H), 7.11 (m, 2H), 7.22 (m, 2H), 7.54 (dd, J=8.61, 5.31 Hz, 1H).

EXAMPLE 2(57)

3-(2-(((4-(2-(3-fluorophenyl)ethyl)tetrahydro-2H-pyran-4-yl)amino)carbonyl)-4-(3-methylindol-1-ylmethyl)phenyl)propanoic acid NMR (300 MHz, CDCl$_3$): δ 1.67 (m, 2H), 2.11 (m, 4H), 2.30 (s, 3H), 2.47 (m, 2H), 2.78 (t, J=7.32 Hz, 2H), 3.05 (t, J=7.32 Hz, 2H), 3.37 (m, 2H), 3.74 (m, 2H), 5.28 (s, 2H), 5.62 (s, 1H), 6.88 (m, 5H), 7.15 (m, 6H), 7.58 (d, J=6.96 Hz, 1H).

EXAMPLE 2(58)

3-(4-(3-cyanophenoxymethyl)-2-(((4-(2-(3-fluorophenyl)ethyl)tetrahydro-2H-pyran-4-yl)amino)carbonyl)phenyl)propanoic acid NMR (300 MHz, CDCl$_3$): δ 1.80 (m, 2H), 2.29 (m, 4H), 2.66 (m, 2H), 2.87 (t, J=7.28 Hz, 2H), 3.13 (t, J=7.28 Hz, 2H), 3.68 (m, 2H), 3.83 (s, 2H), 5.07 (s, 2H), 6.21 (s, 1H), 6.92 (m, 3H), 7.30 (m, 8H).

EXAMPLE 2(59)

3-(4-(2,5-difluorophenoxymethyl)-2-(((4-(2-(4-fluorophenyl)ethyl)tetrahydro-2H-pyran-4-yl)amino)carbonyl)phenyl)propanoic acid NMR (300 MHz, CDCl$_3$): δ 1.82 (m, 2H), 2.25 (m, 4H), 2.64 (m, 2H), 2.84 (t, J=7.32 Hz, 2H), 3.13 (t, J=7.32 Hz, 2H), 3.68 (m, 2H), 3.83 (m, 2H), 5.08 (s, 2H), 6.09 (s, 1H), 6.62 (m, 1H), 6.75 (m, 1H), 6.99 (m, 3H), 7.15 (m, 2H), 7.32 (d, J=7.87 Hz, 1H), 7.45 (m, 2H).

REFERENCE EXAMPLE 12

7-methoxymethoxycoumarine

Under an atmosphere of argon, to a solution of 7-hydroxycoumarine (100 g), isopropylethylamine (161 mL) in anhydrous DMF (500 mL), methoxymethyl chloride (70.3 mL) was dropped at 0° C. The mixture was stirred for 4 hours at room temperature. To the reaction mixture, a mixture of hexane/ethyl acetate (2/1), and a saturated aqueous solution of sodium bicarbonate were added, and extracted with ethyl acetate. The organic layer was washed with water and a saturated aqueous solution of sodium chloride, dried over anhydrous magnesium sulfate and concentrated to give the title compound (74.1 g) having the following physical data.

TLC: Rf 0.50 (hexane:ethyl acetate=3:2); NMR (300 MHz, CDCl$_3$): δ 7.64 (d, J=9.6 Hz, 1H), 7.39 (d, J=8.7 Hz, 1H), 7.01 (d, J=2.4 Hz, 1H), 6.96 (dd, J=8.7, 2.4 Hz, 1H), 6.28 (d, J=9.6 Hz, 1H), 5.24 (s, 2H), 3.49 (s, 3H).

REFERENCE EXAMPLE 13

3-(4-methoxymethoxy-2-hydroxyphenyl)propenoic acid methyl ester

The title compound (100 g) having the following physical data was obtained, using the compound prepared in Reference Example 12 (74.1 g), by the same procedure as a series of reactions of Reference Example 3.

TLC: Rf 0.38 (hexane:ethyl acetate=2:1); NMR (300 MHz, CDCl$_3$): δ 7.92 (d, J=16 Hz, 1H), 7.39 (d, J=8.5 Hz, 1H), 6.62 (dd, J=8.5, 2.2 Hz, 1H), 6.54 (d, J=2.2 Hz, 1H), 6.51 (d, J=16 Hz, 1H), 6.01 (s, 1H), 5.17 (s, 2H), 3.81 (s, 3H), 3.47 (s, 3H).

REFERENCE EXAMPLE 14

3-(4-methoxymethoxy-2-hydroxyphenyl)propanoic acid methyl ester

A solution of the compound prepared in Reference Example 13 (90 g) and 10% palladium carbon (8.4 g) in methanol (1000 mL) was stirred for 7 hours at room temperature under an atmosphere of hydrogen gas. The reaction mixture was filtered through celite (trade mark). The filtrate was concentrated to give the title compound (92.1 g) having the following physical data.

TLC: Rf 0.47 (hexane:ethyl acetate=3:2); NMR (300 MHz, CDCl$_3$): δ 7.24 (s, 6H), 0.97 (d, J=8.2 Hz, 1H), 6.61 (d, J=2.5 Hz, 1H), 6.57 (dd, J=8.2, 2.5 Hz, 1H), 5.13 (s, 2H), 3.69 (s, 3H), 3.46 (s, 3H), 2.84 (t, J=6.1 Hz, 2H), 2.69 (t, J=6.1 Hz, 2H).

REFERENCE EXAMPLE 15

3-(4-methoxymethoxy-2-carboxyphenyl)propanoic acid methyl ester

The title compound (51.4 g) having the following physical data was obtained, using the compound prepared in Reference Example 14 (82.8 g), by the same procedure as a series of reactions of Reference Example 5.

TLC: Rf 0.34 (hexane:ethyl acetate=1:1); NMR (300 MHz, CDCl$_3$): δ 7.71 (d, J=2.7 Hz, 1H), 7.24 (d, J=8.7 Hz, 1H), 7.17 (dd, J=8.7, 2.7 Hz, 1H), 5.20 (s, 2H), 3.67 (s, 3H), 3.49 (s, 3H), 3.27 (t, J=7.6 Hz, 2H), 2.68 (t, J=7.6 Hz, 2H).

REFERENCE EXAMPLE 16

3-(2-((((1R)-1-(naphthalen-1-yl)ethyl)amino)carbonyl)-4-methoxymethoxyphenyl)propanoic acid methyl ester The title compound (15.9 g) having the following physical data was obtained, using the compound prepared in Reference Example 15 (10 g), by the same procedure as a series of reactions of Example 1.

TLC: Rf 0.69 (hexane:ethyl acetate=1:1); NMR (300 MHz, CDCl$_3$): δ 8.23 (d, J=8.7 Hz, 1H), 7.92-7.78 (m, 2H), 7.63-7.43 (m, 4H), 7.12 (d, J=8.1 Hz, 1H), 7.03-6.95 (m, 2H), 6.45 (d, J=8.4 Hz, 1H), 6.12 (m, 1H), 5.10 (s, 2H), 3.61 (s, 3H), 3.41 (s, 3H), 3.00 (t, J=7.5 Hz, 2H), 2.74-2.56 (m, 2H), 1.80 (d, J=6.6 Hz, 3H).

REFERENCE EXAMPLE 17

3-(2-((((1R)-1-(naphthalen-1-yl)ethyl)amino)carbonyl)-4-methoxymethoxyphenyl)propanol Under an atmosphere of argon, to a solution of the compound prepared in Reference Example 16 (15.9 g) in anhydrous tetrahydrofuran (100 mL), lithium borohydride (2.03 g) was added in ice-bath. The mixture was stirred for 4 hours at 60° C. To the reaction mixture, water and a saturated ammonium chloride solution were added. The mixture was extracted with ethyl acetate. The organic layer was washed with water and a saturated aqueous solution of sodium chloride, dried over anhydrous magnesium sulfate and concentrated to give the title compound (13.2 g) having the following physical data.

TLC: Rf 0.32 (hexane:ethyl acetate=1:1); NMR (300 MHz, CDCl$_3$): δ 8.21 (d, J=8.4 Hz, 1H), 7.91-7.80 (m, 2H), 7.63-7.43 (m, 4H), 7.15 (d, J=8.5 Hz, 1H), 7.02 (dd, J=8.5, 2.8 Hz, 1H), 6.91 (d, J=2.8 Hz, 1H), 6.23-6.04 (m, 2H), 5.09 (s, 2H), 3.59-3.43 (m, 3H), 3.41 (s, 3H), 2.88-2.71 (m, 2H), 1.92-1.82 (m, 2H), 1.79 (d, J=6.6 Hz, 3H).

REFERENCE EXAMPLE 18

3-(2-((((1R)-1-(naphthalen-1-yl)ethyl)amino)carbonyl)-4-methoxymethoxyphenyl)propyl methanesulfonate Under an atmosphere of argon, to a solution of the compound prepared in Reference Example 17 (13.2 g) and triethylamine (7.80 mL) in anhydrous THF (80 mL), mesylchloride (3.18 mL) was dropped in ice-bath. The mixture was stirred for 10 minutes. The reaction mixture was diluted with ethyl acetate. The diluted solution was washed with water and a saturated aqueous solution of sodium chloride, dried over anhydrous magnesium sulfate and concentrated to give the title compound (22.3 g) having the following physical data.

TLC: Rf 0.50 (hexane:ethyl acetate=1:1).

REFERENCE EXAMPLE 19

4-(2-((((1R)-1-(naphthalen-1-yl)ethyl)amino)carbonyl)-4-methoxymethoxyphenyl)butanonitrile Under an atmosphere of argon, a solution of the compound prepared in Reference Example 18 (22.3 g) and sodium cyanide (2.01 g) in anhydrous dimethylsulfoxide (100 mL) was stirred for 5 hours at 80° C. To the reaction mixture, water was added in ice-bath. The mixture was extracted with ethyl acetate. The organic layer was washed with water and a saturated aqueous solution of sodium chloride, dried over anhydrous magnesium sulfate and concentrated. The residue was crystallized with t-butyl methyl ether/hexane to give the title compound (10.2 g) having the following physical data.

TLC: Rf 0.32 (hexane:ethyl acetate=1:1); NMR (300 MHz, CDCl$_3$): δ 8.22 (d, J=8.7 Hz, 1H), 7.92-7.80 (m, 2H), 7.64-7.44 (m, 4H), 7.12 (d, J=8.1 Hz, 1H), 7.01 (dd, J=8.1, 2.5 Hz, 1H), 6.95 (d, J=2.5 Hz, 1H), 6.18-5.99 (m, 2H), 5.11 (s, 2H), 3.42 (s, 3H), 2.79 (t, J=7.5 Hz, 2H), 2.30-2.12 (m, 2H), 2.00-1.86 (m, 2H), 1.80 (d, J=6.6 Hz, 3H).

REFERENCE EXAMPLE 20

4-(2-((((1R)-1-(naphthalen-1-yl)ethyl)amino)carbonyl)-4-methoxymethoxyphenyl)butanoic acid To a solution of the compound prepared in Reference Example 19 (7.3 g) in ethanol (30 mL), 33% aqueous solution of potassium hydroxide (10 mL) was added. The mixture was stirred overnight at 80° C. To the reaction mixture, 6N hydrochloric acid was added, and the mixture was extracted with ethyl acetate. The organic layer was washed with water and a saturated aqueous solution of sodium chloride, dried over anhydrous magnesium sulfate and concentrated to give the title compound (9.39 g) having the following physical data.

TLC: Rf 0.33 (chloroform:methanol=19:1); NMR (300 MHz, CDCl$_3$): δ 8.23 (d, J=8.4 Hz, 1H), 7.91-7.78 (m, 2H), 7.63-7.42 (m, 4H), 7.11 (d, J=8.1 Hz, 1H), 6.98 (dd, J=8.2, 2.5 Hz, 1H), 6.92 (d, J=2.5 Hz, 1H), 6.19-6.02 (m, 2H), 5.08 (s, 2H), 3.41 (s, 3H), 2.83-2.64 (m, 2H), 2.37-2.17 (m, 2H), 1.97-1.82 (m, 2H), 1.78 (d, J=6.6 Hz, 3H).

REFERENCE EXAMPLE 21

4-(2-((((1R)-1-(naphthalen-1-yl)ethyl)amino)carbonyl)-4-hydroxyphenyl)butanoic acid methyl ester To a solution of the compound prepared in Reference Example 20 (9.39 g) in methanol (40 mL), concentrated sulfuric acid (1 mL) was added. The mixture was stirred overnight at 60° C. To the reaction mixture, water was added in ice-bath, and the mixture was extracted with ethyl acetate. The organic layer was washed with water and a saturated aqueous solution of sodium chloride, dried over anhydrous magnesium sulfate and concentrated. The residue was crystallized with hexane to give the title compound (6.45 g) having the following physical data.

TLC: Rf 0.45 (hexane:ethyl acetate=1:1); NMR (300 MHz, CDCl$_3$): δ 8.20 (d, J=8.4 Hz, 1H), 7.90-7.76 (m, 2H), 7.59-7.40 (m, 4H), 6.96 (m, 1H), 6.74-6.66 (m, 2H), 6.27-6.04 (m, 3H), 3.57 (s, 3H), 2.75-2.54 (m, 2H), 2.28-2.07 (m, 2H), 1.87-1.67 (m, 2H), 1.76 (d, J=6.6 Hz, 3H).

REFERENCE EXAMPLE 22

2-bromo-5-nitrobenzoic acid benzyl ester

Under an atmosphere of argon, to a solution of 2-bromo-5-nitrobenzoic acid (5.14 g) in DMF, benzyl bromide (2.73 mL) and potassium carbonate (4.33 g) were added. The mixture was stirred for 30 minutes at room temperature. To the reaction mixture, water was added, and the mixture was extracted with ethyl acetate. The organic layer was washed with water and a saturated aqueous solution of sodium chloride, dried over magnesium sulfate and concentrated. The residue was washed with hexane/ethyl acetate to give the title compound (6.59 g) having the following physical data.

TLC: Rf 0.62 (hexane:ethyl acetate=4:1); NMR (300 MHz, CDCl$_3$): δ 8.64 (d, J=2.7 Hz, 1H), 8.16 (dd, J=8.7, 2.7 Hz, 1H), 7.86 (d, J=8.7 Hz, 1H), 7.49-7.39 (m, 5H), 5.42 (s, 2H).

REFERENCE EXAMPLE 23

2-(2-ethoxycarbonylethenyl)-5-nitrobenzoic acid benzyl ester

Under an atmosphere of argon, to a solution of the compound prepared in Reference Example 22 (5.57 g) in dimethyl sulfoxide (30 mL), acrylic acid ethyl ester (3.6 mL), palladium acetate (II) (186 mg), 1,1'-bis(diphenylphosphino) ferrocene (460 mg) and triethylamine (11.6 mL) were added. The mixture was stirred for 4 hours at 80° C. To the reaction mixture, ethyl acetate and water were added, and the mixture was filtered through celite (trade mark). The filtrate was extracted with ethyl acetate. The organic layer was washed with water and a saturated aqueous solution of sodium chloride, dried over magnesium sulfate and concentrated. The residue was purified by column chromatography on silica gel to give the title compound (5.33 g) having the following physical data.

TLC: Rf 0.45 (hexane:ethyl acetate=6:1); NMR (300 MHz, CDCl$_3$): δ 8.82 (d, J=2.1 Hz, 1H), 8.45 (d, J=15.9 Hz, 1H), 8.36 (dd, J=8.7, 2.1 Hz, 1H), 7.75 (d, J=8.7 Hz, 1H), 7.49-7.39 (m, 5H), 6.38 (d, J=15.9 Hz, 1H), 5.42 (s, 2H), 4.29 (q, J=7.2 Hz, 2H), 1.35 (t, J=7.2 Hz, 3H).

REFERENCE EXAMPLE 24

2-(2-ethoxycarbonylethyl)-5-aminobenzoic acid

To a solution of the compound prepared in Reference Example 23 (5.33 g) in ethanol (40 mL)/ethyl acetate (10 mL), 10% palladium carbon (500 mg) was added. The mixture was stirred for 4 hours at room temperature under an atmosphere of hydrogen gas. The reaction mixture was filtered through celite (trade mark). The filtrate was concentrated. The residue was washed with hexane/ethyl acetate to give the title compound (2.72 g) having the following physical data.

TLC: Rf 0.70 (ethyl acetate); NMR (300 MHz, CDCl$_3$): δ 7.35 (d, J=2.7 Hz, 1H), 7.10 (d, J=8.1 Hz, 1H), 6.81 (dd, J=8.1, 2.7 Hz, 1H), 4.11 (q, J=7.2 Hz, 2H), 3.20 (t, J=7.5 Hz, 2H), 2.64 (t, J=7.5 Hz, 2H), 1.23 (t, J=7.2 Hz, 3H).

REFERENCE EXAMPLE 25

2-(2-ethoxycarbonylethyl)-5-(t-butoxycarbonylamino)benzoic acid

A solution of the compound prepared in Reference Example 24 (4.00 g) and t-butyl dicarbonate (5.52 g) in THF (8 mL) was stirred for 2 hours at 65° C. The reaction mixture was concentrated. The residue was crystallized with t-butyl methyl ether/hexane to give the title compound (4.86 g) having the following physical data.

TLC: Rf 0.38 (hexane:ethyl acetate=1:2); NMR (300 MHz, CDCl$_3$): δ 7.94 (d, J=2.1 Hz, 1H), 7.58 (d, J=7.4 Hz, 1H), 7.25 (d, J=7.4 Hz, 1H), 6.63 (brs, 1H), 4.12 (q, J=7.2 Hz, 2H), 3.26 (t, J=7.5 Hz, 2H), 2.67 (t, J=7.5 Hz, 2H), 1.53 (s, 9H), 1.23 (t, J=7.2 Hz, 3H).

EXAMPLE 3

4-(4-(1,3-dioxaindan-5-yloxy)-2-((((1R)-1-(naphthalen-1-yl)ethyl)amino)carbonyl)phenyl)butanoic acid methyl ester A solution of the compound prepared in Reference Example 21 (250 mg), 3,4-(methylenedioxy)phenylboronic acid (318 mg), copper acetate (II) (116 mg), triethylamine (445 μL) and 4 Å molecular sieves (63 mg) in anhydrous methylene chloride was stirred for 3 days at room temperature. The reaction mixture was filtered through celite (trade mark), and the filtrate was diluted with ethyl acetate. The diluted solution was washed with a saturated ammonium chloride solution, water and a saturated aqueous solution of sodium chloride, successively, dried over anhydrous magnesium sulfate and concentrated. The residue was purified by column chromatography on silica gel (hexane:ethyl acetate=3:1) to give the title compound (85 mg) having the following physical data.

TLC: Rf 0.44 (hexane:ethyl acetate=2:1); NMR (300 MHz, CDCl$_3$): δ 8.20 (m, 1H), 7.91-7.79 (m, 2H), 7.59-7.42 (m, 4H), 7.12 (m, 1H), 6.90-6.83 (m, 2H), 6.72 (d, J=8.4 Hz, 1H), 6.50 (d, J=2.4 Hz, 1H), 6.41 (dd, J=8.4, 2.4 Hz, 1H), 6.16-6.02 (m, 2H), 5.99-5.95 (m, 2H), 3.62 (s, 3H), 2.84-2.63 (m, 2H), 2.33-2.12 (m, 2H), 1.96-1.83 (m, 2H), 1.78 (d, J=6.6 Hz, 3H).

EXAMPLE 4

4-(4-(1,3-dioxaindan-5-yloxy)-2-((((1R)-1-(naphthalen-1-yl)ethyl)amino)carbonyl)phenyl)butanoic acid The title compound (74 mg) having the following physical data was obtained, using the compound prepared in Example 3 (80 mg), by the same procedure as a series of reactions of Reference Example 2.

TLC: Rf 0.56 (chloroform:methanol=9:1); NMR (300 MHz, CDCl$_3$): δ 1.77 (d, J=6.32 Hz, 3H), 1.89 (m, 2H), 2.28 (m, 2H), 2.75 (m, 2H), 5.96 (d, J=1.37 Hz, 2H), 6.07 (m, 2H), 6.40 (dd, J=8.45, 2.40 Hz, 1H), 6.49 (d, J=2.40 Hz, 1H), 6.71 (d, J=8.45 Hz, 1H), 6.85 (m, 2H), 7.12 (d, J=8.52 Hz, 1H), 7.51 (m, 4H), 7.84 (m, 2H), 8.18 (d, J=7.97 Hz, 1H).

EXAMPLE 4(1) to 4(48)

The following compounds were obtained by the same procedure as a series of reactions of Reference Example 16→Reference Example 21 →Example 3→Example 4, using the compound prepared in Reference Example 15 and a corresponding compound, or by the same procedure as a series of reactions of Reference Example 16→Example 3→Example 4, using the compound prepared in Reference Example 24 and a corresponding compound, or by the same procedure as a series of reactions of Reference Example 16→Reference Example 17→Reference Example 18 →Reference Example 19→Reference Example 20→Reference Example 21→Example 3→Example 4, using the compound prepared in Reference Example 15 or Reference Example 25 and a corresponding compound.

EXAMPLE 4(1)

4-(4-(3-methylphenoxy)-2-((((1R)-1-(naphthalen-1-yl)ethyl)amino)carbonyl)phenyl)butanoic acid TLC: Rf 0.50 (chloroform:methanol=9:1); NMR (300 MHz, CDCl$_3$): δ 1.77 (d, J=6.59 Hz, 3H), 1.90 (m, 2H), 2.30 (s, 3H), 2.29 (m, 2H), 2.77 (m, 2H), 6.08 (m, 2H), 6.73 (m, 2H), 6.91 (m, 3H), 7.16 (m, 2H), 7.50 (m, 4H), 7.81 (m, 1H), 7.86 (m, 1H), 8.19 (m, 1H).

EXAMPLE 4(2)

4-(4-(3-cyanophenoxy)-2-((((1R)-1-(naphthalen-1-yl)ethyl)amino)carbonyl)phenyl)butanoic acid TLC: Rf 0.25 (hexane:ethyl acetate=1:1); NMR (300 MHz, CDCl$_3$): δ 1.79 (d, J=6.59 Hz, 3H), 1.93 (m, 2H), 2.31 (m, 2H), 2.78 (m, 2H), 6.03 (d, J=8.52 Hz, 1H), 6.12 (m, 1H), 6.95 (m, 2H), 7.14 (m, 2H), 7.23 (d, J=8.79 Hz, 1H) 7.45 (m, 6H), 7.82 (d, J=8.24 Hz, 1H), 7.87 (m, 1H) 8.20 (m, 1H).

EXAMPLE 4(3)

4-(4-(3,4-dimethylphenoxy)-2-((((1R)-1-(naphthalen-1-yl)ethyl)amino)carbonyl)phenyl)butanoic acid TLC: Rf 0.44 (hexane:ethyl acetate=1:1); NMR (300 MHz, CDCl$_3$): δ 1.76 (d, J=6.41 Hz, 3H), 1.91 (m, 2H), 2.20 (s, 3H), 2.23 (s, 3H), 2.30 (m, 2H), 2.76 (m, 2H), 6.08 (m, 2H), 6.67 (dd, J=8.24, 2.56 Hz, 1H), 6.74 (d, J=2.56 Hz, 1H), 6.88 (m, 2H), 7.05 (d, J=8.06 Hz, 1H), 7.12 (d, J=8.24 Hz, 1H), 7.50 (m, 4H), 7.80 (d, J=8.06 Hz, 1H), 7.86 (m, 1H), 8.19 (m, 1H).

EXAMPLE 4(4)

4-(4-(indan-5-yloxy)-2-((((1R)-1-(naphthalen-1-yl)ethyl)amino)carbonyl)phenyl)butanoic acid TLC: Rf 0.42 (hexane:ethyl acetate=1:1); NMR (300 MHz, CDCl$_3$): δ 1.77 (d, J=6.41 Hz, 3H), 1.91 (m, 2H), 2.09 (m, 2H), 2.30 (m, 2H), 2.76 (m, 2H), 2.86 (q, J=7.38 Hz, 4H), 6.06 (m, 2H), 6.72 (dd, J=8.06, 2.38 Hz, 1H), 6.79 (m, 1H), 6.89 (m, 2H), 7.13 (d, J=8.24 Hz, 2H), 7.51 (m, 4H), 7.80 (d, J=8.24 Hz, 1H), 7.87 (m, 1H), 8.19 (m, 1H).

EXAMPLE 4(5)

4-(4-(3,5-dimethylphenoxy)-2-((((1R)-1-(naphthalen-1-yl)ethyl)amino)carbonyl)phenyl)butanoic acid TLC: Rf 0.39 (hexane:ethyl acetate=1:1, 1% acetic acid); NMR (300 MHz, CDCl$_3$): δ 1.77 (d, J=6.59 Hz, 3H), 1.92 (m, 2H), 2.25 (s, 6H), 2.31 (m, 2H), 2.78 (m, 2H), 6.00 (d, J=8.42 Hz, 1H), 6.10 (m, 1H), 6.55 (s, 2H), 6.73 (s, 1H), 6.90 (m, 2H), 7.15 (m, 1H), 7.51 (m, 4H), 7.81 (d, J=8.06 Hz, 1H), 7.87 (m, 1H), 8.20 (m, 1H).

EXAMPLE 4(6)

4-(4-(3-methylthiophenoxy)-2-((((1R)-1-(naphthalen-1-yl)ethyl)amino)carbonyl)phenyl)butanoic acid TLC: Rf 0.35 (hexane:ethyl acetate=1:1, 1% acetic acid); NMR (300 MHz, CDCl$_3$): δ 1.78 (d, J=6.59 Hz, 3H), 1.92 (m, 2H), 2.31 (m, 2H), 2.43 (s, 3H), 2.77 (m, 2H), 6.01 (m, 1H), 6.11 (m, 1H), 6.67 (dd, J=8.42, 2.20 Hz, 1H), 6.83 (t, J=1.83 Hz, 1H), 6.94 (m, 3H), 7.19 (m, 2H), 7.50 (m, 4H), 7.81 (d, J=8.06 Hz, 1H), 7.87 (m, 1H), 8.20 (d, J=8.06 Hz, 1H).

EXAMPLE 4(7)

3-(2-((((1R)-1-(3,5-dimethyl phenyl)-3-methylbutyl)amino)carbonyl)-4-(3-fluorophenylamino)phenyl)propanoic acid TLC: Rf 0.53 (chloroform:methanol=9:1); NMR (300 MHz, DMSO-d$_6$): δ 0.89 (d, J=6.41 Hz, 3H), 0.92 (d, J=6.41 Hz, 3H), 1.38 (m, 1H), 1.72 (m, 2H), 2.23 (s, 6H), 2.42 (m, 2H), 2.77 (t, J=7.78 Hz, 2H), 4.96 (m, 1H), 6.58 (m, 1H), 6.86 (m, 3H), 6.93 (s, 2H), 7.04 (m, 2H), 7.20 (m, 2H), 8.48 (s, 1H), 8.73 (d, J=7.51 Hz, 1H), 12.04 (s, 1H).

EXAMPLE 4(8)

3-(4-(3,5-dimethylphenylamino)-2-((((1R)-1-(3,5-dimethylphenyl)-3-methylbutyl)amino)carbonyl)phenyl)propanoic acid TLC: Rf 0.37 (chloroform:methanol=19:1); NMR (300 MHz, CDCl$_3$): δ 0.96 (d, J=6.22 Hz, 3H), 0.97 (d, J=6.22 Hz, 3H), 1.68 (m, 3H), 2.26 (s, 6H), 2.29 (s, 6H), 2.70 (t, J=7.14 Hz, 2H), 2.95 (m, 2H), 5.14 (m, 1H), 6.23 (d, J=8.79 Hz, 1H), 6.61 (s, 1H), 6.67 (s, 2H), 6.89 (s, 1H), 6.93 (s, 2H), 7.02 (m, 2H), 7.12 (m, 1H).

EXAMPLE 4(9)

3-(2-((((1R)-1-(3,5-dimethylphenyl)-3-methylbutyl)amino)carbonyl)-4-(3-methylphenylamino)phenyl)propanoic acid TLC: Rf 0.33 (chloroform:methanol=19:1); NMR (300 MHz, CDCl$_3$): δ 0.96 (d, J=6.41 Hz, 3H), 0.97 (d, J=6.41 Hz, 3H), 1.67 (m, 3H), 2.29 (s, 6H), 2.30 (s, 3H), 2.70 (t, J=7.69 Hz, 2H), 2.95 (m, 2H), 5.14 (m, 1H), 6.24 (d, J=8.42 Hz, 1H), 6.85 (m, 6H), 7.02 (m, 2H), 7.15 (m, 2H).

EXAMPLE 4(10)

3-(4-(3-cyanophenylamino)-2-((((1R)-1-(3,5-dimethylphenyl)-3-methylbutyl)amino)carbonyl)phenyl)propanoic acid TLC: Rf 0.61 (hexane:ethyl acetate=1:1, 1% acetic acid); NMR (300 MHz, DMSO-d$_6$): δ 0.91 (m, 6H), 1.38 (m, 1H), 1.69 (m, 2H), 2.23 (s, 6H), 2.42 (t, J=7.78 Hz, 2H), 2.78 (t, J=8.06 Hz, 2H), 4.95 (m, 1H), 6.83 (s, 1H), 6.93 (s, 2H), 7.00 (d, J=2.38 Hz, 1H), 7.08 (m, 1H), 7.20 (d, J=8.24 Hz, 2H), 7.37 (m, 3H), 8.62 (s, 1H), 8.77 (d, J=8.79 Hz, 1H).

EXAMPLE 4(11)

3-(4-(3,5-difluorophenylamino)-2-((((1R)-1 (3,5-dimethylphenyl)-3-methylbutyl)amino)carbonyl)phenyl)propanoic acid TLC: Rf 0.76 (hexane:ethyl acetate=1:1, 1% acetic acid); NMR (300 MHz, DMSO-d$_6$): δ 0.90 (d, J=6.41 Hz, 3H), 0.92 (d, J=6.41 Hz, 3H), 1.37 (m, 1H), 1.69 (m, 2H), 2.23 (s, 6H), 2.43 (m, 2H), 2.78 (t, J=7.87 Hz, 2H), 4.95 (m, 1H), 6.53 (m, 1H), 6.67 (dd, J=10.25, 2.20 Hz, 2H), 6.83 (s, 1H), 6.94 (s, 2H), 7.02 (d, J=2.20 Hz, 1H), 7.08 (m, 1H), 7.21 (d, J=8.24 Hz, 1H), 8.72 (s, 1H), 8.80 (m, 1H).

EXAMPLE 4(12)

3-(2-((((1R)-1-(3,5-dimethylphenyl)-3-methylbutyl)amino)carbonyl)-4-(1,3-dioxaindan-5-ylamino)phenyl)propanoic acid TLC: Rf 0.52 (chloroform:methanol=9:1); NMR (300 MHz, CDCl$_3$): δ 0.96 (d, J=6.31 Hz, 3H), 0.97 (d, J=6.31 Hz, 3H), 1.68 (m, 3H), 2.29 (s, 6H), 2.68 (m, 2H), 2.92 (m, 2H), 5.12 (m, 1H), 5.94 (s, 2H), 6.27 (d, J=8.42 Hz, 1H), 6.53 (dd, J=8.24, 2.20 Hz, 1H), 6.64 (d, J=2.20 Hz, 1H), 6.73 (d, J=8.24 Hz, 1H), 6.89 (m, 5H), 7.08 (d, J=8.24 Hz, 1H).

EXAMPLE 4(13)

3-(4-(3,5-dimethylphenoxy)-2-((((1R)-1-(3,5-dimethylphenyl)-3-methylbutyl)amino)carbonyl)phenyl)propanoic acid TLC: Rf 0.47 (hexane:ethyl acetate=1:1, 1% acetic acid); NMR (300 MHz, CDCl$_3$): δ 0.95 (d, J=6.32 Hz, 3H), 0.96 (d, J=6.32 Hz, 3H), 1.67 (m, 3H) 2.28 (s, 6H), 2.29 (s, 6H), 2.72 (m, 2H), 3.00 (m, 2H), 5.13 (m, 1H), 6.19 (d, J=8.60 Hz, 1H), 6.61 (s, 2H), 6.77 (s, 1H), 6.93 (m, 4H), 7.00 (d, J=2.56 Hz, 1H), 7.20 (d, J=8.42 Hz, 1H).

EXAMPLE 4(14)

3-(4-(3,5-difluorophenoxy)-2-((((1R)-1-(3,5-dimethylphenyl)-3-methylbutyl)amino)carbonyl)phenyl)propanoic acid TLC: Rf 0.47 (hexane:ethyl acetate=1:1, 1% acetic acid); NMR (300 MHz, CDCl$_3$): δ 0.97 (d, J=6.41 Hz, 6H), 1.67 (m, 3H), 2.30 (s, 6H), 2.72 (m, 2H), 3.01 (m, 2H), 5.15 (m, 1H), 6.28 (d, J=8.97 Hz, 1H), 6.52 (m, 3H), 6.90 (s, 1H), 6.94 (s, 2H), 7.02 (m, 2H), 7.27 (m, 1H).

EXAMPLE 4(15)

3-(4-(3-cyanophenoxy)-2-((((1R)-1-(3,5-dimethylphenyl)-3-methylbutyl)amino)carbonyl)phenyl)propanoic acid TLC: Rf 0.44 (hexane:ethyl acetate=1:1, 1% acetic acid); NMR (300 MHz, CDCl$_3$): δ 0.97 (d, J=6.59 Hz, 6H), 1.69 (m, 3H), 2.29 (s, 6H), 2.73 (m, 2H), 3.01 (m, 2H), 5.15 (m, 1H), 6.32 (d, J=8.79 Hz, 1H), 6.90 (s, 1H), 6.94 (s, 2H), 7.00 (m, 2H), 7.21 (m, 2H), 7.27 (m, 1H), 7.41 (m, 2H).

EXAMPLE 4(16)

4-(4-(3,5-dimethylphenoxy)-2-((((1R)-1-(naphthalen-2-yl)ethyl)amino)carbonyl)phenyl)butanoic acid TLC: Rf 0.47 (chloroform:methanol=10:1); NMR (300 MHz, CDCl$_3$): δ 1.67 (d, J=6.77 Hz, 3H), 1.92 (m, 2H), 2.27 (s, 6H), 2.31 (t, J=7.20 Hz, 2H), 2.77 (t, J=8.10 Hz, 2H), 5.45 (m, 1H), 6.11 (d, J=7.69 Hz, 1H), 6.59 (s, 2H), 6.75 (s, 1H), 6.94 (dd, J=8.42, 2.56 Hz, 1H), 7.02 (d, J=2.56 Hz, 1H), 7.17 (d, J=8.42 Hz, 1H), 7.48 (m, 3H), 7.82 (m, 4H).

EXAMPLE 4(17)

3-(4-(3,5-dimethylphenoxy)-2-((((1R)-1-(naphthalen-1-yl)ethyl)amino)carbonyl)phenyl)propanoic acid TLC: Rf 0.47 (chloroform:methanol=10:1); NMR (300 MHz, CDCl$_3$): δ 1.78 (d, J=6.77 Hz, 3H), 2.26 (s, 6H), 2.77 (t, J=7.78 Hz, 2H) 3.06 (t, J=7.78 Hz, 2H), 6.12 (m, 1H), 6.27 (d, J=8.06 Hz, 1H), 6.55 (s, 2H), 6.74 (s, 1H), 6.93 (m, 2H), 7.19 (d, J=8.24 Hz, 1H), 7.51 (m, 4H), 7.81 (d, J=8.06 Hz, 1H), 7.87 (m, 1H), 8.17 (d, J=8.60 Hz, 1H).

EXAMPLE 4(18)

3-(4-(3,5-dimethylphenoxy)-2-(((4-(naphthalen-2-yl)tetrahydro-2H-pyran-4-yl)amino)carbonyl)phenyl)propanoic acid TLC: Rf 0.45 (chloroform:methanol=10:1); NMR (300 MHz, CDCl$_3$): δ 2.29 (s, 6H), 2.38 (m, 2H), 2.58 (m, 2H), 2.67 (t, J=7.23 Hz, 2H) 2.96 (t, J=7.23 Hz, 2H), 3.83 (m, 2H), 3.95 (m, 2H), 6.55 (s, 1H), 6.63 (s, 2H), 6.79 (s, 1H) 6.95 (dd, J=8.42, 2.56 Hz, 1H), 7.11 (d, J=2.56 Hz, 1H), 7.19 (d, J=8.42 Hz, 1H), 7.46 (m, 2H), 7.59 (dd, J=8.60, 1.83 Hz, 1H), 7.82 (m, 3H), 7.91 (d, J=1.65 Hz, 1H).

EXAMPLE 4(19)

3-(4-(3,5-dimethylphenoxy)-2-((((1R)-1-(naphthalen-2-yl)ethyl)amino)carbonyl)phenyl)propanoic acid TLC: Rf 0.47 (chloroform:methanol=10:1); NMR (300 MHz, CDCl$_3$): δ 1.68 (d, J=6.96 Hz, 3H), 2.27 (s, 6H), 2.75 (m, J=7.41, 7.41 Hz, 2H), 3.03 (t, J=7.41 Hz, 2H), 5.45 (m, 1H), 6.43 (d, J=7.87 Hz, 1H), 6.60 (s, 2H), 6.76 (s, 1H), 6.95 (dd, J=8.60, 2.75 Hz, 1H), 7.06 (d, J=2.75 Hz, 1H), 7.21 (d, J=8.60 Hz, 1H), 7.48 (m, 3H), 7.83 (m, 4H).

EXAMPLE 4(20)

3-(4-(3,5-dimethylphenoxy)-2-((((1R)-1-(3-methylphenyl)-3-methylbutyl)amino)carbonyl)phenyl)propanoic acid TLC: Rf 0.47 (chloroform:methanol=10:1); NMR (300 MHz, CDCl$_3$): δ 0.96 (d, J=6.30 Hz, 6H), 1.68 (m, 3H), 2.28 (s, 6H), 2.34 (s, 3H), 2.72 (t, J=7.60 Hz, 2H), 2.98 (m, 2H), 5.17 (m, 1H), 6.23 (d, J=8.60 Hz, 1H), 6.61 (s, 2H) 6.77 (s, 1H), 6.94 (dd, J=8.42, 2.56 Hz, 1H), 7.00 (d, J=2.56 Hz, 1H), 7.17 (m, 5H).

EXAMPLE 4(21)

3-(4-(3-methyl phenylamino)-2-(((4-(naphthalen-2-yl)tetrahydro-2H-pyran-4-yl)amino)carbonyl)phenyl)propanoic acid TLC: Rf 0.48 (chloroform:methanol=10:1); NMR (300 MHz, DMSO-d$_6$): δ 2.05 (m, 2H), 2.25 (s, 3H), 2.44 (m, 4H), 2.77 (t, J=7.69 Hz, 2H), 3.79 (m, 4H), 6.67 (d, J=7.32 Hz, 1H), 6.90 (d, J=8.06 Hz, 1H), 7.02 (m, 2H), 7.14 (m, 3H), 7.49 (m, 2H), 7.64 (dd, J=8.60, 1.65 Hz, 1H), 7.87 (m, 4H) 8.21 (s, 1H), 8.71 (s, 1H), 12.06 (s, 1H).

EXAMPLE 4(22)

3-(4-(3,5-dimethylphenylamino)-2-(((4-(naphthalen-2-yl)tetrahydro-2H-pyran-4-yl)amino)carbonyl)phenyl)propanoic acid TLC: Rf 0.49 (chloroform:methanol=10:1); NMR (300 MHz, DMSO-d$_6$): δ 2.05 (m, 2H), 2.21 (s, 6H), 2.47 (m, 4H), 2.76 (t, J=7.87 Hz, 2H), 3.80 (m, 4H), 6.50 (s, 1H), 6.77 (s, 2H), 6.99 (dd, J=8.42, 2.20 Hz, 1H), 7.13 (d, J=8.42 Hz, 1H), 7.18 (d, J=2.20 Hz, 1H), 7.48 (m, 2H), 7.64 (dd, J=8.79, 1.83 Hz, 1H), 7.87 (m, 4H), 8.13 (s, 1H), 8.71 (s, 1H), 12.06 (s, 1H).

EXAMPLE 4(23)

4-(4-(3,5-dimethylphenylamino)-2-((((1R)-1-(naphthalen-1-yl)ethyl)amino)carbonyl)phenyl)butanoic acid TLC: Rf 0.52 (methylene chloride:methanol=9:1); NMR (300 MHz, CDCl$_3$): δ 1.76 (d, J=6.59 Hz, 3H), 1.90 (m, 2H), 2.22 (s, 6H), 2.29 (m, 2H), 2.72 (m, 2H), 6.07 (m, 2H), 6.57 (s, 1H), 6.60 (s, 2H), 6.91 (d, J=2.40 Hz, 1H), 6.99 (dd, J=8.40, 2.40 Hz, 1H), 7.07 (d, J=8.40 Hz, 1H), 7.51 (m, 4H), 7.84 (m, 2H), 8.22 (d, J=8.42 Hz, 1H).

EXAMPLE 4(24)

4-(4-(3-fluorophenylamino)-2-((((1R)-1-(naphthalen 1-yl)ethyl)amino)carbonyl)phenyl)butanoic acid TLC: Rf 0.48 (methylene chloride:methanol=9:1); NMR (300 MHz, CDCl$_3$): δ 1.77 (d, J=6.59 Hz, 3H), 1.90 (m, 2H), 2.28 (m, 2H), 2.73 (m, 2H), 5.70 (s, 1H), 6.09 (m, 2H), 6.61 (m, 3H), 6.94 (d, J=2.20 Hz, 1H), 7.10 (m, 3H), 7.53 (m, 4H), 7.84 (m, 2H), 8.21 (d, J=8.42 Hz, 1H).

EXAMPLE 4(25)

4-(4-(3-methylphenylamino)-2-((((1R)-1-(naphthalen-1-yl)ethyl)amino)carbonyl)phenyl)butanoic acid TLC: Rf 0.44 (methylene chloride:methanol=9:1); NMR (300 MHz, CDCl$_3$): δ 1.76 (d, J=6.59 Hz, 3H), 1.90 (m, 2H), 2.26 (s, 3H), 2.29 (m, 2H), 2.72 (m, 2H), 6.08 (m, 2H), 6.75 (m, 3H), 6.91 (d, J=2.20 Hz, 1H), 7.06 (m, 3H), 7.51 (m, 4H), 7.84 (m, 2H), 8.22 (d, J=8.42 Hz, 1H).

EXAMPLE 4(26)

4-(4-(3,5-difluorophenylamino)-2-((((1R)-1-(naphthalen-1-yl)ethyl)amino)carbonyl)phenyl)butanoic acid TLC: Rf 0.44 (methylene chloride:methanol=9:1); NMR (300 MHz, CDCl$_3$): δ 1.77 (d, J=6.22 Hz, 3H), 1.89 (m, 2H), 2.26 (m, 2H), 2.73 (m, 2H), 5.87 (s, 1H), 6.10 (m, 2H), 6.34 (m, 3H), 6.94 (d, J=2.40 Hz, 1H), 7.06 (dd, J=8.40, 2.40 Hz, 1H), 7.13 (d, J=8.10 Hz, 1H), 7.51 (m, 4H), 7.83 (m, 2H), 8.21 (d, J=8.42 Hz, 1H).

EXAMPLE 4(27)

4-(4-(1,3-dioxaindan-5-ylamino)-2-((((1R)-1-(naphthalen-1-yl)ethyl)amino)carbonyl)phenyl)butanoic acid TLC: Rf 0.52 (methylene chloride:methanol=9:1); NMR (300 MHz, CDCl$_3$): δ 1.76 (d, J=6.59 Hz, 3H), 1.89 (m, 2H), 2.27 (m, 2H), 2.69 (m, 2H), 5.92 (s, 2H), 6.06 (m, 2H), 6.45 (dd, J=8.06, 2.20 Hz, 1H), 6.57 (d, J=1.83 Hz, 1H), 6.68 (d, J=8.40 Hz, 1H), 6.77 (d, J=2.56 Hz, 1H), 6.86 (dd, J=8.40, 2.10 Hz, 1H), 7.02 (d, J=8.06 Hz, 1H), 7.50 (m, 4H), 7.84 (m, 2H), 8.20 (d, J=8.42 Hz, 1H).

EXAMPLE 4(28)

4-(4-(3-cyanophenyl amino)-2-((((1R)-1-(naphthalen-1-yl)ethyl)amino)carbonyl)phenyl)butanoic acid TLC: Rf 0.54 (methylene chloride:methanol=9:1); NMR (300 MHz, CDCl$_3$): δ 1.77 (d, J=6.22 Hz, 3H), 1.89 (m, 2H), 2.27 (m, 2H), 2.73 (m, 2H), 5.94 (s, 1H), 6.12 (m, 2H), 6.93 (d, J=2.20 Hz, 1H), 7.16 (m, 6H), 7.49 (m, 4H), 7.84 (m, 2H), 8.21 (d, J=8.42 Hz, 1H).

EXAMPLE 4(29)

3-(4-(3,5-dimethylphenylamino)-2-((((1R)-1-(3-methylphenyl)-3-methylbutyl)amino)carbonyl)phenyl) propanoic acid TLC: Rf 0.56 (chloroform:methanol=9:1); NMR (300 MHz, DMSO-d$_6$): δ 0.91 (dd, J=10.25, 6.41 Hz, 6H), 1.38 (m, 1H), 1.70 (m, 2H), 2.19 (s, 6H), 2.27 (s, 3H), 2.41 (dd, J=8.97, 6.77 Hz, 2H), 2.74 (t, J=7.78 Hz, 2H), 4.98 (m, 1H), 6.46 (s, 1H) 6.71 (s, 2H), 6.98 (m, 3H), 7.13 (m, 4H), 8.07 (s, 1H), 8.74 (d, J=8.97 Hz, 1H).

EXAMPLE 4(30)

3-(4-(3,5-dimethylphenylamino)-2-((((1R)-1-(naphthalen-1-yl)ethyl)amino)carbonyl)phenyl)propanoic acid TLC: Rf 0.51 (chloroform:methanol=9:1); NMR (300 MHz, DMSO-d$_6$): δ 1.54 (d, J=6.96 Hz, 3H), 2.17 (s, 6H), 2.45 (m, 2H), 2.79 (t, J=7.69 Hz, 2H), 5.91 (m, 1H), 6.46 (s, 1H), 6.68 (s, 2H), 7.00 (m, 2H), 7.11 (m, 1H), 7.54 (m, 4H), 7.82 (d, J=8.06 Hz, 1H), 7.94 (dd, J=7.87, 1.28 Hz, 1H) 8.05 (s, 1H), 8.22 (d, J=8.06 Hz, 1H), 8.99 (m, 1H).

EXAMPLE 4(31)

3-(4-(3,5-dimethylphenylamino)-2-((((1R)-1-(naphthalen-2-yl)ethyl)amino)carbonyl)phenyl)propanoic acid TLC: Rf 0.53 (chloroform:methanol=9:1); NMR (300 MHz, DMSO-d$_6$): δ 1.50 (d, J=6.96 Hz, 3H), 2.18 (s, 6H), 2.44 (m, 2H), 2.79 (t, J=7.69 Hz, 2H), 5.28 (m, 1H), 6.47 (s, 1H), 6.70 (s, 2H), 7.01 (m, 2H), 7.12 (m, 1H), 7.47 (m, 2H), 7.57 (dd, J=8.42, 1.65 Hz, 1H), 7.86 (m, 4H), 8.06 (s, 1H), 8.91 (d, J=8.06 Hz, 1H).

EXAMPLE 4(32)

3-(4-(3,5-dimethylphenylamino)-2-(((4-(3,5-dimethylphenyl)tetrahydro-2H-pyran-4-yl)amino)carbonyl) phenyl)propanoic acid TLC: Rf 0.53 (chloroform:methanol=9:1); NMR (300 MHz, DMSO-d$_6$): δ 1.89 (m, 2H), 2.20 (s, 6H), 2.24 (s, 6H), 2.40 (m, 4H), 2.75 (m, 2H), 3.73 (m, 4H), 6.48 (s, 1H), 6.77 (s, 2H), 6.83 (s, 1H), 6.98 (dd, J=8.33, 2.29 Hz, 1H), 7.03 (s, 2H), 7.12 (d, J=8.24 Hz, 1H), 7.19 (d, J=2.20 Hz, 1H), 8.12 (s, 1H), 8.54 (s, 1H).

EXAMPLE 4(33)

3-(4-(3,5-dimethylphenylamino)-2-(((4-(3-methylphenyl)tetrahydro-2H-pyran-4-yl)amino)carbonyl) phenyl)propanoic acid TLC: Rf 0.44 (chloroform:methanol=9:1); NMR (300 MHz, DMSO-d$_6$): δ 1.92 (m, 2H), 2.20 (s, 6H), 2.28 (s, 3H), 2.41 (m, 4H), 2.76 (m, 2H), 3.75 (m, 4H), 6.48 (s, 1H), 6.76 (s, 2H), 6.99 (m, 2H), 7.12 (d, J=8.42 Hz, 1H), 7.21 (m, 5H), 8.12 (s, 1H).

EXAMPLE 4(34)

3-(4-(3,5-dimethylphenoxy)-2-(((4-(3-methylphenyl)tetrahydro-2H-pyran-4-yl)amino)carbonyl)phenyl)propanoic acid TLC: Rf 0.49 (chloroform:methanol=9:1); NMR (300 MHz, CDCl$_3$): δ 2.22 (m, 2H), 2.30 (s, 6H), 2.35 (s, 3H), 2.47 (m, 2H), 2.69 (t, J=7.14 Hz, 2H), 2.97 (t, J=7.23 Hz, 2H), 3.77 (m, 2H) 3.91 (m, 2H), 6.40 (s, 1H), 6.63 (m, 2H) 6.78 (m, 1H), 6.95 (dd, J=8.51, 2.65 Hz, 1H), 7.08 (m, 2H) 7.20 (d, J=8.42 Hz, 1H), 7.26 (m, 3H).

EXAMPLE 4(35)

3-(2-(((4-(benzofuran-2-yl)tetrahydro-2H-pyran-4-yl)amino)carbonyl)-4-(3,5-dimethylphenoxy)phenyl)propanoic acid TLC: Rf 0.52 (chloroform:methanol=9:1); NMR (300 MHz, CDCl$_3$): δ 2.28 (s, 6H), 2.48 (m, 4H), 2.69 (t, J=7.14 Hz, 2H), 2.98 (t, J=7.14 Hz, 2H), 3.83 (m, 4H), 6.61 (m, 3H), 6.76 (m, 2H), 6.95 (dd, J=8.42, 2.56 Hz, 1H), 7.09 (d, J=2.56 Hz, 1H), 7.22 (m, 3H), 7.38 (m, 1H), 7.55 (m, 1H).

EXAMPLE 4(36)

3-(2-(((4-(benzofuran-2-yl)tetrahydro-2H-pyran-4-yl)amino)carbonyl)-4-(3,5-dimethylphenylamino)phenyl)propanoic acid TLC: Rf 0.50 (chloroform:methanol=9:1); NMR (300 MHz, CDCl$_3$): δ 2.27 (s, 6H), 2.48 (m, 4H), 2.69 (t, J=7.10 Hz, 2H), 2.94 (t, J=7.10 Hz, 2H), 3.84 (m, 4H), 6.63 (m, 2H), 6.69 (s, 2H), 6.74 (d, J=0.73 Hz, 1H), 7.07 (m, 3H), 7.21 (m, 2H), 7.39 (m, 1H), 7.55 (m, 1H).

EXAMPLE 4(37)

3-(4-(3,5-dimethylphenoxy)-2-(((4-(2-phenylethyl)tetrahydro-2H-pyran-4-yl)amino)carbonyl)phenyl)propanoic acid TLC: Rf 0.50 (chloroform:methanol=10:1); NMR (300 MHz, DMSO-d$_6$): δ 1.50 (m, 2H), 2.00 (m, 2H), 2.22 (s, 6H), 2.26 (m, 2H), 2.48 (m, 2H), 2.58 (m, 2H), 2.93 (m, 2H), 3.52 (m, 2H), 3.65 (m, 2H), 6.68 (s, 2H), 6.78 (s, 1H), 6.92 (d, J=2.56 Hz, 1H), 6.97 (dd, J=8.40, 2.56 Hz, 1H), 7.14 (m, 3H), 7.26 (m, 3H), 8.01 (s, 1H).

EXAMPLE 4(38)

3-(4-(3,5-dimethylphenoxy)-2-(((4-(3,5-dimethylphenyl)tetrahydro-2H-pyran-4-yl)amino)carbonyl)phenyl)propanoic acid TLC: Rf 0.50 (chloroform:methanol=10:1); NMR (300 MHz, DMSO-d$_6$): δ 1.89 (m, 2H), 2.21 (s, 6H), 2.25 (s, 6H), 2.35 (d, J=12.63 Hz, 2H), 2.44 (m, 2H), 2.84 (t, J=7.96 Hz, 2H), 3.69 (m, 4H) 6.69 (s, 2H), 6.81 (m, 2H), 6.89 (d, J=2.75 Hz, 1H), 6.98 (m, 3H), 7.29 (d, J=8.42 Hz, 1H), 8.54 (s, 1H).

EXAMPLE 4(39)

3-(4-(3,5-dimethylphenylamino)-2-(((4-(2-phenylethyl)tetrahydro-2H-pyran-4-yl)amino)carbonyl)phenyl)propanoic acid TLC: Rf 0.48 (chloroform:methanol=10:1); NMR (300 MHz, DMSO-d$_6$): δ 1.49 (m, 2H), 2.01 (m, 2H), 2.16 (s, 6H), 2.27 (d, J=14.10 Hz, 2H), 2.57 (m, 4H), 2.88 (t, J=7.87 Hz, 2H), 3.62 (m, 4H), 6.44 (s, 1H), 6.75 (s, 2H), 6.98 (dd, J=8.42, 2.38 Hz, 1H), 7.15 (m, 5H), 7.24 (m, 2H) 7.99 (s, 1H), 8.11 (s, 1H).

EXAMPLE 4(40)

3-(2-(((4-(3,5-dimethylphenyl)tetrahydro-2H-pyran-4-yl)amino)carbonyl)-4-(3-methylphenylamino)phenyl)propanoic acid TLC: Rf 0.49 (chloroform:methanol=9:1); NMR (300 MHz, DMSO-d$_6$): δ 1.90 (m, 2H), 2.24 (s, 9H), 2.41 (m, 4H), 2.78 (t, J=8.06 Hz, 2H), 3.74 (m, 4H), 6.65 (d, J=6.96 Hz, 1H), 6.83 (s, 1H), 6.90 (d, J=9.15 Hz, 1H), 7.01 (m, 4H), 7.12 (m, 3H), 8.20 (s, 1H), 8.53 (s, 1H).

EXAMPLE 4(41)

3-(2-(((4-(benzothiophen-2-yl)tetrahydro-2H-pyran-4-yl)amino)carbonyl)-4-(3,5-dimethylphenoxy)phenyl)propanoic acid TLC: Rf 0.49 (chloroform:methanol=10:1); NMR (300 MHz, DMSO-d$_6$): δ 2.05 (m, 2H), 2.25 (s, 6H), 2.54 (m, 4H), 2.87 (t, J=7.87 Hz, 2H), 3.73 (m, 4H), 6.68 (s, 2H), 6.82 (s, 1H), 6.97 (m, 2H), 7.32 (m, 4H), 7.75 (m, 1H), 7.84 (dd, J=8.06, 0.92 Hz, 1H), 8.85 (s, 1H).

EXAMPLE 4(42)

3-(2-(((4-(benzothiophen-2-yl)tetrahydro-2H-pyran-4-yl)amino)carbonyl)-4-(3,5-dimethylphenylamino)phenyl)propanoic acid TLC: Rf 0.47 (chloroform:methanol=10:1); NMR (300 MHz, DMSO-d$_6$): δ 2.04 (m, 2H), 2.20 (s, 6H), 2.59 (m, 4H), 2.81 (m, 2H), 3.75 (m, 4H), 6.49 (s, 1H), 6.76 (s, 2H), 7.00 (dd, J=8.33, 2.29 Hz, 1H), 7.13 (d, J=8.42 Hz, 1H), 7.19 (d, J=2.38 Hz, 1H), 7.32 (m, 3H), 7.76 (dd, J=6.96, 1.65 Hz, 1H), 7.82 (d, J=8.42 Hz, 1H), 8.14 (s, 1H), 8.82 (s, 1H).

EXAMPLE 4(43)

3-(4-(3,5-dimethylphenoxy)-2-(((4-(2-(4-fluorophenyl)ethyl)tetrahydro-2H-pyran-4-yl)amino)carbonyl)phenyl)propanoic acid TLC: Rf 0.52 (chloroform:methanol=9:1); NMR (300 MHz, CDCl$_3$): δ 1.79 (m, 2H), 2.23 (m, 4H), 2.28 (s, 6H), 2.60 (m, 2H), 2.83 (t, J=7.40 Hz, 2H), 3.08 (t, J=7.40 Hz, 2H), 3.65 (m, 2H), 3.82 (m, 2H), 5.96 (s, 1H), 6.64 (s, 2H), 6.78 (s, 1H), 6.95 (m, 3H), 7.06 (d, J=2.56 Hz, 1H), 7.12 (m, 2H), 7.22 (d, J=8.60 Hz, 1H).

EXAMPLE 4(44)

3-(4-(3,5-dimethylphenylamino)-2-(((4-(2-(4-fluo-rophenyl)ethyl)tetrahydro-2H-pyran-4-yl)amino)carbonyl)phenyl)propanoic acid TLC: Rf 0.50 (chloroform:methanol=9:1); NMR (300 MHz, CDCl$_3$): δ 1.78 (m, 2H), 2.24 (m, 10H), 2.60 (m, 2H), 2.81 (t, J=7.32 Hz, 2H), 3.04 (t, J=7.32 Hz, 2H), 3.63 (m, 2H), 3.81 (m, 2H), 5.98 (s, 1H), 6.62 (s, 1H), 6.70 (s, 2H), 6.94 (m, 2H), 7.10 (m, 5H).

EXAMPLE 4(45)

3-(4-(3,5-dimethylphenylamino)-2-(((4-(2-(2-fluo-rophenyl)ethyl)tetrahydro-2H-pyran-4-yl)amino)carbonyl)phenyl)propanoic acid TLC: Rf 0.36 (hexane:ethyl acetate=1:1, 1% acetic acid); NMR (300 MHz, CDCl$_3$): δ 1.80 (m, 2H), 2.24 (m, 10H), 2.68 (m, 2H), 2.83 (t, J=7.28 Hz, 2H), 3.05 (t, J=7.28 Hz, 2H), 3.66 (m, 2H), 3.84 (m, 2H), 5.96 (s, 1H), 6.63 (s, 1H), 6.71 (s, 2H), 7.09 (m, 7H).

EXAMPLE 4(46)

3-(4-(3,5-dimethylphenoxy)-2-(((4-(2-(2-fluorophe-nyl)ethyl)tetrahydro-2H-pyran-4-yl)amino)carbonyl)phenyl)propanoic acid TLC: Rf 0.39 (hexane:ethyl acetate=1:1, 1% acetic acid); NMR (300 MHz, DMSO-d$_6$): δ 1.50 (m, 2H), 1.98 (m, 2H), 2.25 (m, 8H), 2.56 (m, 4H), 2.92 (t, J=7.78 Hz, 2H), 3.52 (m, 2H), 3.66 (m, 2H), 6.67 (d, J=0.73 Hz, 2H), 6.77 (s, 1H), 6.95 (m, 2H), 7.09 (m, 2H), 7.20 (m, 2H), 7.30 (d, J=8.42 Hz, 1H), 8.03 (s, 1H).

EXAMPLE 4(47)

3-(4-(3,5-dimethylphenoxy)-2-(((4-(2-(3-fluorophe-nyl)ethyl)tetrahydro-2H-pyran-4-yl)amino)carbonyl)phenyl)propanoic acid TLC: Rf 0.52 (chloroform:methanol=9:1); NMR (300 MHz, CDCl$_3$): δ 1.78 (m, 2H), 2.24 (m, 4H), 2.28 (s, 6H), 2.63 (m, 2H), 2.83 (t, J=6.99 Hz, 2H), 3.08 (t, J=6.99 Hz, 2H), 3.64 (m, 2H), 3.82 (m, 2H), 5.96 (s, 1H), 6.64 (s, 2H), 6.78 (s, 1H), 6.91 (m, 4H), 7.05 (d, J=2.56 Hz, 1H), 7.22 (m, 2H).

EXAMPLE 4(48)

3-(4-(3,5-dimethylphenylamino)-2-(((4-(2-(3-fluo-rophenyl)ethyl)tetrahydro-2H-pyran-4-yl)amino)carbonyl)phenyl)propanoic acid TLC: Rf 0.52 (chloroform:methanol=9:1); NMR (300 MHz, CDCl$_3$): δ 1.77 (m, 2H), 2.24 (m, 10H), 2.61 (m, 2H), 2.82 (t, J=7.36 Hz, 2H), 3.04 (t, J=7.36 Hz, 2H), 3.65 (m, 2H), 3.81 (m, 2H), 5.99 (s, 1H), 6.62 (s, 1H), 6.70 (s, 2H), 7.05 (m, 7H).

FORMULATION EXAMPLE 1

The following components were admixed in conventional method and punched out to obtain 100 tablets each containing 5 mg of active ingredient.

| | |
|---|---|
| The compound of the present invention | 500 mg |
| Carboxymethylcellulose calcium (disintegrating agent) | 200 mg |
| Magnesium stearate (lubricating agent) | 100 mg |
| Microcrystalline cellulose | 9.2 g |

FORMULATION EXAMPLE 2

The following components were admixed in conventional method. The solution was sterilized in conventional manner, placed 5 ml portions into ampoules and freeze-dried to obtain 100 ampoules each containing 20 mg of the active ingredient.

| | |
|---|---|
| The compound of the present invention | 2.0 g |
| Mannitol | 20 g |
| Distilled water | 500 ml |

TEST EXAMPLE 1

It was confirmed that the present compounds bind strongly and show an antagonizing activity on the PGE$_2$ receptor, especially, EP$_3$ receptor, for example, by following experiments.

(i) Binding Assay Using Cell Expressing the Prostanoid Receptor Subtypes

The preparation of membrane fraction was carried out according to the method of Sugimoto et al. [*J. Biol. Chem.*, 267, 6463-6466 (1992)], using CHO cell expressing prostanoid receptor subtypes (mouse EP$_1$, EP$_2$, EP$_{3\alpha}$, and EP$_4$).

The standard assay mixture containing membrane fraction (50 μL), [$^3$H]-PGE$_2$ in a final volume of 150 μL was incubated for 1 hour at room temperature. The reaction was terminated by addition of 3 mL of ice-cold buffer. The mixture was rapidly filtered through a glass filter (GF/B) under reduced pressure. The radioactivities associated with the filters were measured by liquid scintillation counter.

Kd and Bmax values were determined from Scatchard plots [*Ann. N.Y. Acad. Sci.*, 51, 660(1949)]. Non-specific binding was determined as the amount bound in the presence of an excess (10 μM) of unlabeled PGE$_2$. In the experiment for competition of specific [$^3$H]-PGE$_2$ binding assay, [$^3$H]-PGE$_2$ was added at a concentration of 2.5 nM and a test compound of the present invention was added at various concentrations. The following buffer was used in all reactions.

Buffer: 10 mM potassium phosphate (pH 6.0), 1 mM EDTA, 10 mM MgCl$_2$, 0.1 M NaCl. [C] is the concentrated of [$^3$H]-PGE$_2$.

The inhibition constant (Ki) of each compound was calculated by the following equation.

$$Ki=IC_{50}/(1+([C]/Kd))$$

As a result, it was noted that Ki of the present compound was below 100 nM and bind strongly on EP$_3$ receptor.

(ii) EP$_3$ Antagonizing Activity Assay Using the Cell Expressing the Prostanoid Receptor Subtypes The preparation of CHO cell expressing mouse EP$_3$ receptor subtype was carried out according to the method of Sugimoto et al. [*J. Biol. Chem.*, 267, 6463-6466 (1992)]. The cells were cultured in 96-well microplates (10$^4$ cells/well) for two days before experiments. After washing each well with 100

µL of PBS, Fura-2AM was added to taken in the cell for 60 minutes. After washing each well with HEPES, then a test compound and $PGE_2$ (10 nM) were added at 37° C. A variation of intracellular calcium concentration was measured. Namely, excitation with a wavelength of 340/380 nm carried out, and fluorescence of 510 nm was measured, then a ratio of fluorescence intensity was calculated. By the way, an antagonizing activity of a test compound was calculated as inhibitory rate on the condition using $PGE_2$ (10 nM) as an agonist, and then $IC_{50}$ value was calculated.

As a result, it was noted that $IC_{50}$ of the present compound was below 100 nM and the present compound has a strong activity on $EP_3$ receptor.

TEST EXAMPLE 2

A suppressive effect of the compound of the present invention to pain reaction of an adjuvant-induced arthritis model which is a pain model for chronic arthritis was investigated as follows using a squeaking reaction as an index.

Lewis male rats of seven weeks age were used. After volume of the left hind leg of each rat was measured, 600 µg/100 µL of dried cells of *Mycobacterium butyricum* (Difco) suspended in liquid paraffin was injected as an adjuvant into paw skin of a right hind leg to prepare an adjuvant-arthritis rat. After 22 days from injection of the adjuvant, bending and stretching of a knee joint of the left hind leg were conducted for five times before oral administration of a test substance and the rats which squeaked for all of the five times were subjected to the experiment. Depending upon the volume of edema of left hind leg on the previous day, grouping was conducted where one group comprised ten rats. Each of the compound of the present invention (1, 3, 10 and 30 mg/kg) and a 0.5% aqueous solution of methyl cellulose (5 mL/kg) as a control was orally administered. An analgesic action was observed after 1, 2, 3 and 4 hour(s) from the administration. Judgment of the analgesic effect where the analgesic action was used as an index was conducted in the following manner that, at each stage of the observation, bending and stretching of the knee joint of left hind leg were conducted for five times and the case where no analgesic action was noted for all of five times was defined as negative for the analgesic action while the individual where the analgesic reaction was noted at an evaluating point of one point or more was defined as positive for the analgesic action.

As a result, no individual which was positive for the analgesic action was noted in the control group while, in a group administered with the compound (I) for example, individual which was positive for the analgesic action was noted as from 10 mg/kg or lower whereupon an analgesic action of an EP3 receptor antagonist to pain of the adjuvant-induced arthritis model was noted.

TEST EXAMPLE 3

An analgesic effect of the compound of the present invention to carrageenin-induced hyperalgesia model which was an acute inflammation pain model was investigated as follows using escape latency as an index.

Male rats of an SD strain of seven weeks age were used. Thermal stimulation was irradiated to right hind leg of each rat using a measuring device for a plantar test and the time until escape raising the leg was measured and used as the escape latency. Depending upon the escape latency, grouping was conducted where each group comprised 7 to 8 rats and each of the compound of the present invention (3, 10 and 30 mg/kg) and a 0.5% aqueous solution of methyl cellulose (5 mL/kg) as a control was orally administered. After 1 hour from the oral administration of a test substance, carrageenin (2 mg/100 µL) dissolved in a physiological saline was subcutaneously injected to the sole of right hind leg of the rat. The escape latency during 3 hours after injection of carrageenin was measured.

As a result, a decrease in the escape latency was noted in the control group by injection of carrageenin and hyperalgesia was induced while, in the group administered with the compound (I) for example, its escape latency was significantly high as compared with the control group as from not more than 10 mg/kg whereupon an improving action of an $EP_3$ receptor antagonist to the carrageenin-induced hyperalgesia was noted.

TEST EXAMPLE 4

A suppressive action of the compound of the present invention to a pollakiuria model induced by sulprostone was investigated as follows.

Male Crj: CD (SD) IGS rats of body weight of about 300 g were used. Each of the compound of the present invention (3, 10, 30 and 100 mg/kg) and a 0.5% aqueous solution of methyl cellulose (5 mL/kg) as a control was orally administered. After 0.5 hour from oral administration of a test substance, sulprostone (0.2 mg/4 mL/kg) was subcutaneously administered. As a non-induced group, a 0.5% aqueous solution of methyl cellulose was orally administered and, after y hour(s), a physiological saline was subcutaneously administered. Measurement of urination was conducted from immediately after administration of sulprostone until 3 hours thereafter. Measurement of urination was done in such a manner that, under the condition of giving neither feed nor water, the animals were placed in a metabolic cage equipped with a urine measuring device and weight of the collected urine with a lapse of time was recorded using a data-collecting system. Incidentally, case numbers for each group were made 3 to 4 cases.

The result was that an increase in urination frequency was noted by a subcutaneous administration of sulprostone in the control group while, in the group administered with the compound (I) for example, urination frequency showed low values as from not more than 30 mg/kg. As a result thereof, a suppressive action of an $EP_3$ receptor antagonist to pollakiuria induced by sulprostone was noted.

TEST EXAMPLE 5

A suppressive action of the compound of the present invention to increases in ACTH and corticosterone induced by sulprostone is able to be investigated.

Male Crj: CD (SD) IGS rats are used. A compound of the present invention or aqueous solution of NaOH as a control is orally administered and, after 1 hour, sulprostone is subcutaneously administered. As a non-induced group, aqueous solution of NaOH is orally administered and, after 1 hour, a physiological saline is subcutaneously administered. After 1 hour from administration of sulprostone, the rats are decapitated and blood is collected. After EDTA and aprotinin are added to the blood followed by centrifuging and concentration of ACTH or corticosterone in the supernatant liquid thereof is measured.

TEST EXAMPLE 6

A suppressive action of the compound of the present invention to a spontaneous scratching behavior of NC mice where dermatitis is spontaneously appeared is able to be investigated.

Male NC mice where dermatitis is spontaneously appeared are used. The mice are placed in an observation cage and acclimated to the environment for 30 minutes and a scratching behavior during 1 hour is recorded by videotape under an unattended circumstance. As a result of playback of the videotape, a series of behavior of a mouse which scratches face, ear, back of neck and surrounding areas thereof by its hind leg is judged as a scratching behavior and its frequency is counted. Every 30 minutes, the compound of the present invention or a 0.5% aqueous solution of methyl cellulose as a control is orally administered for 3 to 5 times as a whole. Video recording is conducted for 1 to 3 hour(s) as from immediately after the second administration and scratching times by the mouse are counted.

TEST EXAMPLE 7

When 0.3% dinitrofluorobenzene (DNFB) is repeatedly applied on the head skin of Brown Norway (BN) rats to induce dermatitis, an increase in spontaneous scratching behavior is noted within 24 to 27 hours after the application. A suppressive effect of the compound of the present invention to the scratching behavior is able to be investigated.

To the cut head skin of the male BN rats, a 0.3% DNFB dissolved in a mixture of acetone with olive oil is applied as a hapten. As a non-induced group, a mixture of acetone with olive oil is applied. After one week, it is applied again on the head skin and, after that, three applications are repeated every other day. Within 24 to 27 hours after the fourth application, the rats were taken by video under an unattended circumstance. As a result of playback of the videotape, a series of behavior of a rat which scratches the area around the site to which the hapten is applied by its hind leg is judged as a scratching behavior and its frequency is counted. After 12 to 48 hours from the third to the sixth applications, the compound of the present invention or a 0.5% aqueous solution of methyl cellulose as a control is orally administered. To a non-induced group, a 0.5% aqueous solution of methyl cellulose is orally administered. Video recording is conducted for 30 minutes to 3 hours after the administration and scratching times by the rat are counted.

The invention claimed is:

1. A carboxylic acid compound of formula (I):

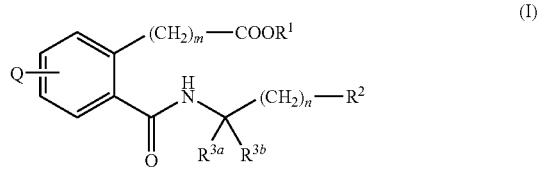

(I)

wherein $R^1$ is hydrogen or C1-4 alkyl;
$R^2$ is phenyl, naphthyl, benzofuranyl or benzothionyl, which is unsubstituted or substituted with 1-2 of C1-4 alkyl and/or halogen;
Q is (i) —$CH_2$—O-Cyc1, (ii) —$CH_2$-Cyc2 or (iii) -L-Cyc3;
Cyc1 is phenyl or pyridyl, which is unsubstituted or substituted with 1-2 of $R^4$;
Cyc2 is indolyl which is unsubstituted or substituted with 1-2 of $R^4$;
Cyc3 is phenyl substituted with 1-2 of $R^4$;
L is —O— or —NH—;
$R^{3a}$ and $R^{3b}$ each independently is hydrogen or C1-4 alkyl or
$R^{3a}$ and $R^{3b}$, taken together with the carbon atom to which they are attached, form tetrahydro-2H-pyran;
m is 2 or 3;
n is 0, 1 or 2;
$R^4$ is C1-4 alkyl, C1-4 alkylthio, halogen or cyano, or when Cyc3 is phenyl substituted with two $R^4$, two $R^4$ taken together with phenyl may form

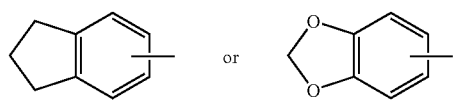

or a salt thereof.

2. The carboxylic acid compound according to claim 1, which is
(1) 3-(4-(2,5-difluorophenoxymethyl)-2-((((1R)-1-(naphthalen-2-yl)ethyl)amino)carbonyl)phenyl)propanoic acid,
(2) 3-(4-(2,5-dichlorophenoxymethyl)-2-(((4-(3-methylphenyl)tetrahydro-2H-pyran-4-yl)amino)carbonyl) phenyl)propanoic acid,
(3) 3-(4-(2-chloro-5-methylphenoxymethyl)-2-(((4-(3-methylphenyl)tetrahydro-2H-pyran-4-yl)amino)carbonyl)phenyl)propanoic acid,
(4) 3-(4-(2-chloro-5-fluorophenoxymethyl)-2-(((4-(3-methylphenyl)tetrahydro-2H-pyran-4-yl)amino)carbonyl) phenyl)propanoic acid,
(5) 3-(4-(2,5-difluorophenoxymethyl)-2-(((4-phenyltetrahydro-2H-pyran-4-yl)amino)carbonyl)phenyl)propanoic acid,
(6) 3-(4-(2,5-dichlorophenoxymethyl)-2-(((4-phenyltetrahydro-2H-pyran-4-yl)amino)carbonyl)phenyl)propanoic acid,
(7) 3-(4-(2-chloro-5-fluorophenoxymethyl)-2-(((4-phenyltetrahydro-2H-pyran-4-yl)amino)carbonyl)phenyl) propanoic acid,
(8) 3-(4-(2,5-difluorophenoxymethyl)-2-((((1R) -3-methyl-1(3-mehtyphenyl)butyl)amino)carbonyl)phenyl) propanoic acid,
(9) 3-(4-(3-cyanophenoxymethyl)-2-(((((1R)-3-methyl-1-(3-methylphenyl)butyl)amino)carbonyl)phenyl)propanoic acid,
(10) 3-(4-(2,5-dimethylphenoxymethyl)-2-((((1R)-3-methyl-1-(3-methylphenyl)butyl)amino)carbonyl)phenyl) propanoic acid,
(11) 3-(4-(2,5-difluorophenoxymethyl)-2-(((4-(naphthalen-2-yl)tetrahydro-2H-pyran-4-yl)amino)carbonyl) phenyl)propanoic acid,
(12) 3-(4-(2,5-dimethylphenoxymethyl)-2-(((4-(3-methylphenyl)tetrahydro-2H-pyran-4-yl)amino)carbonyl) phenyl)propanoic acid,
(13) 3-(4-(3-cyanophenoxymethyl)-2-(((4-(naphthalen-2-yl)tetrahydro-2H-pyran-4-yl)amino)carbonyl)phenyl) propanoic acid,
(14) 3-(4-(2,5-dimethylphenoxymethyl)-2-(((4-(naphthalen-2-yl)tetrahydro-2H-pyran-4-yl)amino)carbonyl) phenyl)propanoic acid,

(15) 3-(4-(5-fluoroindol-1-ylmethyl)-2-(((((1R)-1-(3,5-dimethylphenyl)-3-methylbutyl)amino)carbonyl)phenyl)propanoic acid,
(16) 3-(4-(2,4-dimethylphenoxymethyl)-2-(((((1R)-1-(3,5-dimethylphenyl)-3-methylbutyl)amino)carbonyl)phenyl)propanoic acid,
(17) 3-(2-(((4-(naphthalen-2-yl)tetrahydro-2H-pyran-4-yl)amino)carbonyl)-4-phenoxymethylphenyl)propanoic acid,
(18) 3-(2-(((4-(naphthalen-2-yl)tetrahydro-2H-pyran-4-yl)amino)carbonyl)-4-(3-pyridyloxymethyl)phenyl)propanoic acid,
(19) 3-(4-(3-chlorophenoxymethyl)-2-(((4-(naphthalen-2-yl)tetrahydro-2H-pyran-4-yl)amino)carbonyl)phenyl)propanoic acid,
(20) 3-(4-(3,4-dimethylphenoxymethyl)-2-(((((1R)-1-(3,5-dimethylphenyl)-3-methylbutyl)amino)carbonyl)phenyl)propanoic acid,
(21) 3-(4-(2-chloro-5-fluorophenoxymethyl)-2-(((((1R)-1-(3,5-dimethylphenyl)-3-methylbutyl)amino)carbonyl)phenyl)propanoic acid,
(22) 3-(2-(((((1R)-1-(3,5-dimethylphenyl)-3-methylbutyl)amino)carbonyl)-4-(3-methylindol-1-ylmethyl)phenyl)propanoic acid,
(23) 3-(4-(2,5-difluorophenoxymethyl)-2-(((((1R)-1-(naphthalen-1-yl)ethyl)amino)carbonyl)phenyl)propanoic acid,
(24) 3-(4-(2-fluoro-5-methylphenoxymethyl)-2-(((((1R)-1-(naphthalen-1-yl)ethyl)amino)carbonyl)phenyl)propanoic acid,
(25) 3-(2-(((4-(3,5-dimethylphenyl)tetrahydro-2H-pyran-4-yl)amino) carbonyl)-4-(2-fluoro-5-methylphenoxymethyl)phenyl)propanoic acid,
(26) 3-(4-(2-fluoro-5-methylphenoxymethyl)-2-(((4-(3-methylphenyl)tetrahydro-2H-pyran-4-yl)amino)carbonyl)phenyl)propanoic acid,
(27) 3-(2-(((4-(benzofuran-2-yl)tetrahydro-2H-pyran-4-yl)amino)carbonyl)-4-(2,5-difluorophenoxymethyl)phenyl)propanoic acid,
(28) 3-(2-(((((1R)-1-(3,5-dimethylphenyl)-3-methylbutyl)amino)carbonyl)-4-(4-fluoro-2-methylphenoxymethyl)phenyl)propanoic acid,
(29) 3-(2-(((((1R)-1-(3,5-dimethylphenyl)-3-methylbutyl)amino)carbonyl)-4-((2-methylpyridin-3-yl)oxymethyl)phenyl)propanoic acid,
(30) 3-(2-(((((1R)-1-(3,5-dimethylphenyl)-3-methylbutyl)amino)carbonyl)-4-((2-methylpyridin-5-yl)oxymethyl)phenyl)propanoic acid,
(31) 3-(4-(3-fluorophenoxymethyl)-2-(((4-(naphthalen-2-yl)tetrahydro-2H-pyran-4-yl)amino)carbonyl)phenyl)propanoic acid,
(32) 3-(4-(3-methylphenoxymethyl)-2-(((4-(naphthalen-2-yl)tetrahydro-2H-pyran-4-yl)amino)carbonyl)phenyl)propanoic acid,
(33) 3-(4-(2,5-dimethylphenoxymethyl)-2-(((4-(2-phenylethyl)tetrahydro-2H-pyran-4-yl)amino)carbonyl)phenyl)propanoic acid,
(34) 3-(2-(((4-(benzofuran-2-yl)tetrahydro-2H-pyran-4-yl)amino)carbonyl)-4-(2,5-dimethylphenoxymethyl)phenyl)propanoic acid,
(35) 3-(2-(((4-(benzothiophen-2-yl)tetrahydro-2H-pyran-4-yl)amino)carbonyl)-4-(2,5-dimethylphenoxymethyl)phenyl)propanoic acid,
(36) 3-(4-(2,5-difluorophenoxymethyl)-2-(((4-(2-(2-fluorophenyl)ethyl)tetrahydro-2H-pyran-4-yl)amino)carbonyl)phenyl)propanoic acid,
(37) 3-(4-(2,5-dimethylphenoxymethyl)-2-(((4-(2-(2-fluorophenyl)ethyl)tetrahydro-2H-pyran-4-yl)amino)carbonyl)phenyl)propanoic acid,
(38) 3-(4-(2,5-dimethylphenoxymethyl)-2-(((4-(2-(4-fluorophenyl)ethyl)tetrahydro-2H-pyran-4-yl)amino)carbonyl)phenyl)propanoic acid,
(39) 3-(4-(2,5-dimethylphenoxymethyl)-2-(((4-(2-(3-fluorophenyl)ethyl)tetrahydro-2H-pyran-4-yl)amino)carbonyl)phenyl)propanoic acid,
(40) 3-(4-(6-fluoroindol-1-ylmethyl)-2-(((4-(2-phenylethyl)tetrahydro-2H-pyran-4-yl)amino)carbonyl)phenyl)propanoic acid,
(41) 3-(4-(6-fluoroindol-3-ylmethyl)-2-(((4-(2-phenylethyl)tetrahydro-2H-pyran-4-yl)amino)carbonyl)phenyl)propanoic acid,
(42) 3-(4-(3-methylindol-1-ylmethyl)-2-(((4-(2-phenylethyl)tetrahydro-2H-pyran-4-yl)amino)carbonyl)phenyl)propanoic acid,
(43) 3-(4-(3-cyanophenoxymethyl)-2-(((4-(2-phenylethyl)tetrahydro-2H-pyran-4-yl)amino)carbonyl)phenyl)propanoic acid,
(44) 3-(4-(6-fluoroindol-1-ylmethyl)-2-(((4-(naphthalen-2-yl)tetrahydro-2H-pyran-4-yl)amino)carbonyl)phenyl)propanoic acid,
(45) 3-(4-(6-fluoroindol-3-ylmethyl)-2-(((4-(naphthalen-2-yl)tetrahydro-2H-pyran-4-yl)amino)carbonyl)phenyl)propanoic acid,
(46) 3-(4-(3-methylindol-1-ylmethyl)-2-(((4-(naphthalen-2-yl)tetrahydro-2H-pyran-4-yl)amino)carbonyl)phenyl)propanoic acid,
(47) 3-(4-(6-fluoroindol-1-ylmethyl)-2-(((4-(2-(3-fluorophenyl)ethyl)tetrahydro-2H-pyran-4-yl)amino)carbonyl)phenyl)propanoic acid,
(48) 3-(2-(((4-(2-(3-fluorophenyl)ethyl)tetrahydro-2H-pyran-4-yl)amino)carbonyl)-4-(3-methylindol-1-ylmethyl)phenyl)propanoic acid,
(49) 3-(4-(3-cyanophenoxymethyl)-2-(((4-(2-(3-fluorophenyl)ethyl)tetrahydro-2H-pyran-4-yl)amino)carbonyl)phenyl)propanoic acid,
(50) 4-(4-(1,3-dioxaindan-5-yloxy)-2-(((((1R)-1-(naphthalen-1-yl)ethyl)amino)carbonyl)phenyl)butanoic acid,
(51) 4-(4-(3-methylphenoxy)-2-(((((1R)-1-(naphthalen-1-yl)ethyl)amino)carbonyl)phenyl)butanoic acid,
(52) 4-(4-(3-cyanophenoxy)-2-(((((1R)-1-(naphthalen-1-yl)ethyl)amino)carbonyl)phenyl)butanoic acid,
(53) 4-(4-(3,4-dimethylphenoxy)-2-(((((1R)-1-(naphthalen-1-yl)ethyl)amino)carbonyl)phenyl)butanoic acid,
(54) 4-(4-(indan-5-yloxy)-2-(((((1R)-1-(naphthalen-1-yl)ethyl)amino)carbonyl)phenyl)butanoic acid,
(55) 4-(4-(3,5-dimethylphenoxy)-2-(((((1R)-1-(naphthalen-1-yl)ethyl)amino)carbonyl)phenyl)butanoic acid,
(56) 4-(4-(3-methylthiophenoxy)-2-(((((1R)-1-(naphthalen-1-yl)ethyl)amino)carbonyl)phenyl)butanoic acid,
(57) 3-(2-(((((1R)-1-(3,5-dimethylphenyl)-3-methylbutyl)amino)carbonyl)-4-(3-fluorophenylamino)phenyl)propanoic acid,
(58) 3-(2-(((((1R)-1-(3,5-dimethylphenyl)-3-methylbutyl)amino)carbonyl)-4-(3-methylphenylamino)phenyl)propanoic acid,
(59) 3-(4-(3-cyanophenylamino)-2-(((((1R)-1-(3,5-dimethylphenyl)-3-methylbutyl)amino)carbonyl)phenyl)propanoic acid,
(60) 3-(4-(3,5-difluorophenylamino)-2-(((((1R)-1-(3,5-dimethylphenyl)-3-methylbutyl)amino)carbonyl)phenyl)propanoic acid,

(61) 3-(2-((((1R)-1-(3,5-dimethylphenyl)-3-methylbutyl)amino)carbonyl)-4-(1,3-dioxaindan-5-ylamino)phenyl)propanoic acid,
(62) 3-(4-(3,5-difluorophenoxy)-2-((((1R)-1-(3,5-dimethylphenyl)-3-methylbutyl)amino)carbonyl)phenyl)propanoic acid,
(63) 3-(4-(3-cyanophenoxy)-2-((((1R)-1-(3,5-dimethylphenyl)-3-methylbutyl)amino)carbonyl)phenyl)propanoic acid,
(64) 4-(4-(3,5-dimethylphenoxy)-2-((((1R)-1-(naphthalen-2-yl)ethyl)amino)carbonyl)phenyl)butanoic acid,
(65) 3-(4-(3,5-dimethylphenoxy)-2-((((1R)-1-(naphthalen-1-yl)ethyl)amino)carbonyl)phenyl)propanoic acid,
(66) 3-(4-(3,5-dimethylphenoxy)-2-((((1R)-1-(naphthalen-2-yl)ethyl)amino)carbonyl)phenyl)propanoic acid,
(67) 3-(4-(3,5-dimethylphenoxy)-2-((((1R)-1-(3-methylphenyl)-3-methylbutyl)amino)carbonyl)phenyl)propanoic acid,
(68) 3-(4-(3-methylphenylamino)-2-(((4-(naphthalen-2-yl)tetrahydro-2H-pyran-4-yl)amino)carbonyl)phenyl)propanoic acid,
(69) 4-(4-(3-fluorophenylamino)-2-((((1R)-1-(naphthalen-1-yl)ethyl)amino)carbonyl)phenyl)butanoic acid,
(70) 4-(4-(3-methylphenylamino)-2-((((1R)-1-(naphthalen-1-yl)ethyl)amino)carbonyl)phenyl)butanoic acid,
(71) 4-(4-(3,5-difluorophenylamino)-2-((((1R)-1-(naphthalen-1-yl)ethyl)amino)carbonyl)phenyl)butanoic acid,
(72) 4-(4-(1,3-dioxaindan-5-ylamino)-2-((((1R)-1-(naphthalen-1-yl)ethyl)amino)carbonyl)phenyl)butanoic acid,
(73) 4-(4-(3-cyanophenylamino)-2-((((1R)-1-(naphthalen-1-yl)ethyl)amino)carbonyl)phenyl)butanoic acid,
(74) 3-(4-(3,5-dimethylphenylamino)-2-((((1R)-1-(naphthalen-1-yl)ethyl)amino)carbonyl)phenyl)propanoic acid,
(75) 3-(4-(3,5-dimethylphenylamino)-2-((((1R)-1-(naphthalen-2-yl)ethyl)amino)carbonyl)phenyl)propanoic acid,
(76) 3-(4-(3,5-dimethylphenylamino)-2-(((4-(3,5-dimethylphenyl)tetrahydro-2H-pyran-4-yl)amino)carbonyl)phenyl)propanoic acid,
(77) 3-(4-(3,5-dimethylphenylamino)-2-(((4-(3-methylphenyl)tetrahydro-2H-pyran-4-yl)amino)carbonyl)phenyl)propanoic acid,
(78) 3-(4-(3,5-dimethylphenoxy)-2-(((4-(3-methylphenyl)tetrahydro-2H-pyran-4-yl)amino)carbonyl)phenyl)propanoic acid,
(79) 3-(2-(((4-(benzofuran-2-yl)tetrahydro-2H-pyran-4-yl)amino)carbonyl)-4-(3,5-dimethylphenoxy)phenyl)propanoic acid,
(80) 3-(2-(((4-(benzofuran-2-yl)tetrahydro-2H-pyran-4-yl)amino)carbonyl)-4-(3,5-dimethylphenylamino)phenyl)propanoic acid,
(81) 3-(4-(3,5-dimethylphenoxy)-2-(((4-(2-phenylethyl)tetrahydro-2H-pyran-4-yl)amino)carbonyl)phenyl)propanoic acid,
(82) 3-(4-(3,5-dimethylphenoxy)-2-(((4-(3,5-dimethylphenyl)tetrahydro-2H-pyran-4-yl)amino)carbonyl)phenyl)propanoic acid,
(83) 3-(4-(3,5-dimethylphenylamino)-2-(((4-(2-phenylethyl)tetrahydro-2H-pyran-4-yl)amino)carbonyl)phenyl)propanoic acid,
(84) 3-(2-(((4-(3,5-dimethylphenyl)tetrahydro-2H-pyran-4-yl)amino)carbonyl)-4-(3-methylphenylamino)phenyl)propanoic acid,
(85) 3-(2-(((4-(benzothiophen-2-yl)tetrahydro-2H-pyran-4-yl)amino)carbonyl)-4-(3,5-dimethylphenylamino)phenyl)propanoic acid,
(86) 3-(4-(3,5-dimethylphenoxy)-2-(((4-(2-(4-fluorophenyl)ethyl)tetrahydro-2H-pyran-4-yl)amino)carbonyl)phenyl)propanoic acid,
(87) 3-(4-(3,5-dimethylphenylamino)-2-(((4-(2-(4-fluorophenyl)ethyl)tetrahydro-2H-pyran-4-yl)amino)carbonyl)phenyl)propanoic acid,
(88) 3-(4-(3,5-dimethylphenylamino)-2-(((4-(2-(2-fluorophenyl)ethyl)tetrahydro-2H-pyran-4-yl)amino)carbonyl)phenyl)propanoic acid,
(89) 3-(4-(3,5-dimethylphenoxy)-2-(((4-(2-(2-fluorophenyl)ethyl)tetrahydro-2H-pyran-4-yl)amino)carbonyl)phenyl)propanoic acid or
(90) 3-(4-(3,5-dimethylphenoxy)-2-(((4-(2-(3-fluorophenyl)ethyl)tetrahydro-2H-pyran-4-yl)amino)carbonyl)phenyl)propanoic acid,
or a salt thereof.

3. The carboxylic acid compound according to claim 1, which is (1) 3-(2-((((1R)-1-(3,5-dimethylphenyl)-3-methylbutyl)amino)carbonyl)-4-(5-fluoro-2-methylphenoxymethyl)phenyl)propanoic acid,
(2) 3-(2-(((4-(benzothiophen-2-yl)tetrahydro-2H-pyran-4-yl)amino)carbonyl)-4-(2,5-difluorophenoxymethyl)phenyl)propanoic acid,
(3) 3-(4-(2-fluoro-5-methylphenoxymethyl)-2-((((1R)-3-methyl-1-(3-methylphenyl)butyl)amino)carbonyl)phenyl)propanoic acid,
(4) 3-(4-(2,5-difluorophenoxymethyl)-2-(((4-(2-(3-fluorophenyl)ethyl)tetrahydro-2H-pyran-4-yl)amino)carbonyl)phenyl)propanoic acid,
(5) 3-(4-(3,5-dimethylphenylamino)-2-(((4-(naphthalen-2-yl)tetrahydro-2H-pyran-4-yl)amino)carbonyl)phenyl)propanoic acid,
(6) 3-(2-(((4-(benzothiophen-2-yl)tetrahydro-2H-pyran-4-yl)amino)carbonyl)-4-(3,5-dimethylphenoxy)phenyl)propanoic acid,
(7) 3-(4-(2,5-difluorophenoxymethyl)-2-(((4-(2-phenylethyl)tetrahydro-2H-pyran-4-yl)amino)carbonyl)phenyl)propanoic acid,
(8) 3-(2-((((1R)-1-(3,5-dimethylphenyl)-3-methylbutyl)amino)carbonyl)-4-(3-pyridyloxymethyl)phenyl)propanoic acid,
(9) 3-(4-(2-fluoro-5-methylphenoxymethyl)-2-((((1R)-1-(3,5-dimethylphenyl)-3-methylbutyl)amino)carbonyl)phenyl)propanoic acid,
(10) 3-(4-(3,5-dimethylphenylamino)-2-((((1R)-1-(3,5-dimethylphenyl)-3-methylbutyl)amino)carbonyl)phenyl)propanoic acid,
(11) 3-(4-(6-fluoroindol-1-ylmethyl)-2-((((1R)-1-(3,5-dimethylphenyl)-3-methylbutyl)amino)carbonyl)phenyl)propanoic acid,
(12) 3-(4-(3,5-dimethylphenoxy)-2-(((4-(naphthalen-2-yl)tetrahydro-2H-pyran-4-yl)amino)carbonyl)phenyl)propanoic acid,
(13) 4-(4-(3,5-dimethylphenylamino)-2-((((1R)-1-(naphthalen-1-yl)ethyl)amino)carbonyl)phenyl)butanoic acid,
(14) 3-(4-(2-chloro-5-methylphenoxymethyl)-2-((((1R)-3-methyl-1-(3-methylphenyl)butyl)amino)carbonyl)phenyl)propanoic acid,
(15) 3-(4-(2,5-difluorophenoxymethyl)-2-(((4-(2-(4-fluorophenyl)ethyl)tetrahydro-2H-pyran-4-yl)amino)carbonyl)phenyl)propanoic acid,

(16) 3-(4-(3,5-dimethylphenylamino)-2-((((1R)-1-(3-methylphenyl)-3-methylbutyl)amino)carbonyl)phenyl)propanoic acid,

(17) 3-(4-(2-fluoro-5-methylphenoxymethyl)-2-(((4-(naphthalen-2-yl)tetrahydro-2H-pyran-4-yl)amino)carbonyl)phenyl)propanoic acid,

(18) 3-(4-(3,5-dimethylphenoxy)-2-((((1R)-1-(3,5-dimethylphenyl)-3-methylbutyl)amino)carbonyl)phenyl)propanoic acid or

(19) 3-(4-(3,5-dimethylphenylamino)-2-(((4-(2-(3-fluorophenyl)ethyl)tetrahydro-2H-pyran-4-yl)amino)carbonyl)phenyl)propanoic acid, or a salt thereof.

4. A pharmaceutical composition, which comprises the carboxylic acid compound according to claim 1, or a salt thereof, and a pharmaceutically acceptable carrier.

5. The pharmaceutical composition according to claim 4, which is $EP_3$ receptor antagonist.

6. The pharmaceutical composition according to claim 5, which is a therapeutic agent for diseases induced by excess activation of $EP_3$ receptor, wherein the diseases are one or more selected from pruritis, arthritis pain or neuropathic pain, urinary disturbance.

7. The pharmaceutical composition according to claim 6, wherein the urinary disturbance is urinary frequency.

8. A pharmaceutical composition which comprises the carboxylic acid compound according to claim 1, or a salt thereof, and one or more medicaments selected from steroid drugs, non-steroidal antiinflammatory drugs, immunosuppressants, anti-allergic drugs, mediator-release inhibitors, leukotriene receptor antagonists, antihistamine drugs, forskolin preparations, phosphodiesterase inhibitors, nitric oxide synthase inhibitors, cannabinoid-2 receptor stimulators, nonopioid analgesics, nonsteroidal anti-inflammatory drugs, cyclooxygenase inhibitors, opioid analgesics, Prostaglandins, N-type calcium channel blockers, α1 adrenaline receptor blockers, progesterone preparations, anticholinergic agents, muscarine receptor antagonists, $5\text{-}HT_{1A}$ receptor agonists, σ1 receptor agonists, serotonin nervous system agonists, corticotropin releasing factor receptor antagonists, proton pump inhibitors, M1 receptor antagonists, cytoprotective agents, tricyclic antidepressants, and tetracyclic antidepressants.

9. A method for treating diseases induced by excess activation of $EP_3$ receptor in a mammal, which comprises administering to the mammal an effective amount of the carboxylic acid compound according to claim 1, or a salt thereof, wherein the diseases are one or more selected from pruritis, arthritis pain or neuropathic pain, urinary disturbance.

10. A carboxylic acid compound which is 3-(2-((((1R)-1-(3,5-dimethylphenyl)-3-methylbutyl)amino)carbonyl)-4-(5-fluoro-2-methylphenoxymethyl)phenyl)propanoic acid or a pharmaceutically acceptable salt thereof.

* * * * *